US012788521B1

(12) United States Patent
Schecter

(10) Patent No.: US 12,788,521 B1
(45) Date of Patent: Nov. 10, 2026

(54) WEARABLE HAPTIC SENSORY FEEDBACK SYSTEM FOR INTERVENTIONAL CARDIOLOGY PROCEDURES

(71) Applicant: Cardia Tact Control LLC, Great Neck, NY (US)

(72) Inventor: Stuart Schecter, Great Neck, NY (US)

(73) Assignee: HapticHeart Solutions, Newport Coast, CA (US)

( * ) Notice: Subject to any disclaimer, the term of this patent is extended or adjusted under 35 U.S.C. 154(b) by 556 days.

(21) Appl. No.: 18/310,977

(22) Filed: May 2, 2023

Related U.S. Application Data

(63) Continuation-in-part of application No. 17/888,746, filed on Aug. 16, 2022.

(60) Provisional application No. 63/576,899, filed on Mar. 13, 2023, provisional application No. 63/475,698, filed on Dec. 5, 2022, provisional application No. 63/473,452, filed on May 28, 2022, provisional application No. 63/473,303, filed on May 17, 2022, provisional application No. 63/473,117, filed on May 2, 2022, provisional application No. 63/473,116, filed on May 2, 2022, provisional application No. 63/233,665, filed on Aug. 16, 2021.

(51) Int. Cl.
*A61B 34/00* (2016.01)
*A61B 17/00* (2006.01)

(52) U.S. Cl.
CPC .... *A61B 34/76* (2016.02); *A61B 2017/00243* (2013.01); *A61B 2034/741* (2016.02)

(58) Field of Classification Search
CPC .......................... A61B 2034/741; A61B 34/76
See application file for complete search history.

(56) References Cited

U.S. PATENT DOCUMENTS

| | | | | |
|---|---|---|---|---|
| 2008/0167662 A1* | 7/2008 | Kurtz | A61B 34/70 606/130 |
| 2013/0321262 A1* | 12/2013 | Schecter | A61B 34/76 345/156 |
| 2021/0282804 A1* | 9/2021 | Worrell | A61B 34/37 |
| 2022/0096187 A1* | 3/2022 | Xu | A61B 34/76 |
| 2023/0067021 A1* | 3/2023 | Baltrunas | A61B 34/37 |

* cited by examiner

*Primary Examiner* — Carl H Layno
*Assistant Examiner* — Jennifer Ghand
(74) *Attorney, Agent, or Firm* — Barnes & Thornburg LLP

(57) ABSTRACT

A wearable haptic sensory feedback system for interventional cardiology procedures includes at least two wearable surface elements, each configured to interface with a different region of a limb of the operator and a processor. The wearable surface elements include at least three haptic actuators positioned along a first section of the limb and at least one haptic actuator positioned along a separate, second section of the limb. The processor receives a set of physiological signals representing parameters sensed by an interventional cardiology device and a set of event signals representing procedural events associated with the interventional cardiology procedure and provides somatosensory tactile and force feedback along the first section as a set of real time spatial haptic sensations related to the set of physiological signals and along the second section as a set of event haptic sensations related to the set of event signals.

7 Claims, 57 Drawing Sheets

FIG. 23C
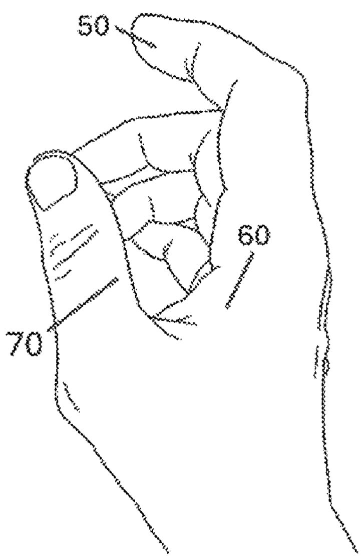
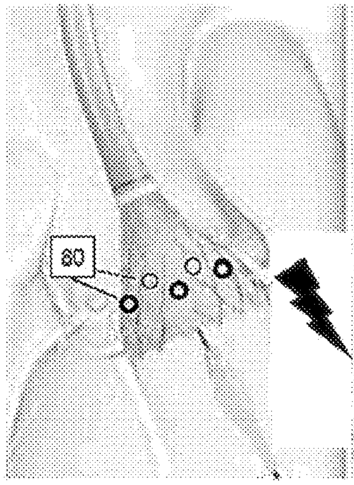
FIG. 23A
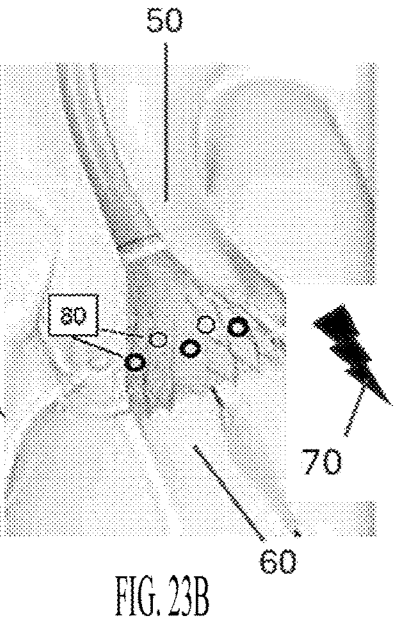
FIG. 23B

WEARABLE HAPTIC SENSORY FEEDBACK SYSTEM FOR INTERVENTIONAL CARDIOLOGY PROCEDURES

RELATED APPLICATIONS

The present application claims the benefit of the following U.S. provisional applications, each of which is incorporated herein in its entirety by reference:

- U.S. Provisional Application No. 63/576,899 entitled DEVICE AGNOSTIC GEOMETRIC CARDIOVASCULAR HAPTIC SYSTEM and filed Mar. 13, 2023;
- U.S. Provisional Application No. 63/475,698 entitled DEVICE AGNOSTIC INTERVENTIONAL HAPTIC SYSTEM 2 and filed Dec. 5, 2022;
- U.S. Provisional Application No. 63/473,452 entitled HAPTIC HEART HAND and filed May 28, 2022;
- U.S. Provisional Application No. 63/473,303 entitled HAPTIC CARDIOVASCULAR BRAIN INTERFACE and filed May 17, 2022;
- U.S. Provisional Application No. 63/473,117 entitled HAPTIC HOLOGRAPHIC HOMONCULUS and filed May 2, 2022; and,
- U.S. Provisional Application No. 63/473,116 entitled HAPTIC CARDIOVASCULAR TACTICAL SYSTEM and filed May 2, 2022.

The present application is also a continuation-in-part of U.S. Nonprovisional application Ser. No. 17/888,746 entitled DEVICE AGNOSTIC INTERVENTIONAL HAPTIC SYSTEM and filed on Aug. 16, 2022, which is unpublished, and which claims the benefit of U.S. Provisional Application No. 63/233,665 filed Aug. 16, 2021, each of which is incorporated herein in its entirety by reference.

TECHNICAL FIELD

The present disclosure relates generally to means for providing haptic feedback and to cardiovascular instruments having means for providing feel, force, or tactile feedback. More particularly, the present disclosure relates to wearable haptic sensory feedback systems for use with methods and apparatuses for interventional cardiology procedures that provide a less intrusive and more effective operator haptic feel and feedback to an operator in a haptic format of multiple physiological parameters sensed by an interventional cardiology device and transduced salient procedural events.

BACKGROUND

Various haptic-enabled solutions for cardiology have been developed and patented by the inventor of this application as represented by U.S. Pat. Nos. 8,663,122 and 8,956,304 directed to cardiac haptic handle inventions, and U.S. Pat. Nos. 8,942,848 and 10,013,082 directed to inventions for haptic interfaces and operating systems for those interfaces. These inventions have significant advantages over other types of haptic arrangements configured primarily for providing operator control over surgical devices, such as described, for example, in U.S. Pat. Nos. 9,445,876, 9,750,577, and 10,932,876.

Although haptic sensory feedback systems for interventional cardiology have been developed, it would be desirable to improve on such systems to provide a less intrusive and more effective operator haptic feel and feedback of physiological and physical parameters sensed by an interventional cardiology device.

SUMMARY OF THE DISCLOSURE

Embodiments of the present disclosure provide a wearable haptic sensory feedback system for interventional cardiology procedures is adapted to receive a first set of physiological signals representing a plurality of physiological parameters sensed by an interventional cardiology device and a second set of event signals representing at least one transduced procedural event associated with an interventional cardiology procedure performed by an operator. In embodiments, the haptic system includes at least two wearable surface elements, each wearable surface element configured to interface with a different region of an upper limb of the operator and a processor system operably coupled to the at least two wearable surface elements and to an electrical power source. At least one surface element includes a first configuration of at least three haptic actuators positioned in a spaced apart relation to each other along a first section that corresponds to a linear portion of the upper limb of the operator having afferent nerves. At least another of the surface elements includes a second configuration of at least one haptic actuator positioned to correspond to a second section of the upper limb of the operator physically separated from first section. In embodiments, the processor system is adapted to receive the first set of signals and the second set of signals and configured to provide the operator with somatosensory tactile and force feedback along the first section as a set of real time spatial haptic sensations related to the first set of physiological signals and to provide the operator with somatosensory tactile and force feedback along the second section as a set of event haptic sensations related to the second set of event signals.

In various embodiments, the haptic system reduces the potential for central and peripheral neurological desensitization while providing operators with mechanical, physiological, physical, and anatomical information in a haptic format complementing and/or replacing visual and/or audio displays with special attention to ensuring that haptic somatosensory signals innervate specific parts of the operator's sensory cortex. In embodiments, the haptic system delivers tactile and force signals along an operator's upper limb (finger, hand, wrist, arm) in a contiguous fashion as to recreate, in real time, signals from anatomically contiguous structures along the course of an inserted catheter during electrophysiologic procedures or structural heart interventions including but not limited to catheter based or minimally invasive valve replacement/repair. In embodiments, the anatomic representations are of key structures and include the ascending aorta, sinus of Valsalva, aortic valve, left ventricular outflow tract, left ventricle, left and right atria, mitral valve, tricuspid valve, interatrial septum, left atrium, pulmonary vein, left atrial appendage and implanted devices (e.g., left atrial occlusion system, valve replacements).

In various embodiments, the haptic system can recognize dissimilar signal formats near instantaneously, perform A/D conversion and digital signal processing, identify which signals are most accurate and specific for the data set of interest, and generate haptic output with minimal latency. Various embodiments are constructed to input differing signals sensed by varying types of mechanical and/or physiologic sensors and process diverse signals with a unified computing system capable of recognizing static, quasistatic, and dynamic data (e.g., time varying waveforms of pressure or force, quasistatic electrical indices of measured impedance, differentials in tissue voltage or current, time varying measurements of temperature, static indices of tissue damage), correcting for inaccuracies due to alterations in signal quality or changes in the sensing environment (e.g., from changes in temperature due to infusion of saline from an ablation catheter) and performing minimal latency transduction of such data as output in a haptic format to a user. In other embodiments, down-sized actuators are geometrically arranged and strategically activated to simulate amplitude and frequency characteristics of sensed physiological signals.

Haptic output is processed and designed to activate varying peripheral and central neuroanatomical sites to prevent fatigue of tactile and force sensing attentional resources. These sites including kinesthetic, proprioceptive, temperature, tactile, and pressure receptors are preferably located in the fingers, hand, wrist, forearm, and arm. Haptic feedback is generated by one or combinations of haptic actuator(s) including but not limited to piezo actuators, linear or rotary motors, smart materials, haptic speakers and the like and are configured as a wearable interface.

In some embodiments, the haptic system monitors an operator's handling of inserted instrumentation and calculates haptic to motor response times for quality assurance, educational purposes, and to detect potentially deleterious actions as to alert an operator to modify his or her procedural approach or autonomously terminate the actual procedure or specific actions. In this context, the haptic system is reciprocating and can both sense an operator's actions and provide haptic feedback.

In some embodiments, the wearable surface elements are formed of a portion of a fabric sleeve with at least one haptic actuator having one or more piezoelectric elements formed of at least one of: piezo yarn, piezoelectric fibers, or flexible piezoelectric membranes.

In some embodiments, the interventional cardiology device is a catheter, and the first set of physiological signals is generated in response to a set of sensors configured to detect physiological phenomena that vary as a distal portion of the catheter is inserted into a patient. In various of these embodiments, the processor is configured to process and generate the set of real time spatial haptic sensations as a distal to proximal sequence of activations of the first configuration of at least three haptic actuators that the operator can correlate to different depths as the distal portion as the catheter is inserted into the patient.

In some embodiments, the processor system is configured to store the first set of physiological signals, the second set of event signals, the set of real time spatial haptic sensations related to the first set of physiological signals, and the set of event haptic sensations related to the second set of event signals for the interventional cardiology procedure for use in future training or assessment of the wearable haptic sensory feedback system or the operator. In various of these embodiments, the processor system is configured to store a set of time stamps related to at least some of the first set of physiological signals and the second set of event signals for use in assessment of time periods between changes in physiological data or between events during the interventional cardiology procedure. In various of these embodiments, the first set of physiological signals are representative of changes in distance over time between anatomic structures associated with previously stored biophysical events, and the set of real time spatial haptic sensations are generated using real-time haptic pulsations at a ratio relative to a sensed cardiac cycle of the patient during the cardiology interventional procedure.

In some embodiments, the haptic system further includes an operator sensor system configured to sense information related to peripheral nerve recruitment and relevant motor responses of the operator during the interventional cardiology procedure. In these embodiments, the sense information from the operator sensor system is utilized by a processor system to evaluate attention and reaction of the operator during the procedure and to generate indications of changes in either attention or reaction of the operator during the interventional cardiology procedure.

In some embodiments, the processor system is configured to provide the operator with somatosensory tactile and force feedback with the set of real time spatial haptic sensations related to the first set of physiological signals stimulating afferent neurologic impulses to a first region of the brain of the operator, and the set of event haptic sensations related to the second set of event signals stimulating afferent neurologic impulses to a different second region of the brain of the operator, whereby an increased ability of the operator to form a real time haptic representational map of a heart of the patient during the cardiology interventional procedure is increased. In various of these embodiments, the first region and the second region of the brain are contiguous, and each is assigned to receive different haptic stimulations from different contiguous anatomic portions of the limb of the operator.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which:

FIG. 1A shows a static signal indicative of tissue necrosis;

FIG. 1B shows a quasistatic signal indicative of tissue impedance demonstrating tissue damage (steam pop) during ablation;

FIG. 1C shows a quasistatic signal of contact sensing magnitude derived from differentials in current, impedance, or voltage between one or more electrodes;

FIG. 1D shows a quasistatic signal indicative of tissue temperature; and

FIG. 1E shows a quasistatic and dynamic signal of tissue impedance demonstrating pulsatile impedance along the mitral annulus and tissue damage (steam pop) during ablation of the posterior wall (P), respectively.

FIG. 2A shows a dynamic signal representative of time varying intracardiac pressure (P);

FIG. 2B shows a dynamic signal representative of time varying tissue; catheter contact force (CF); and FIG. 2C shows a dynamic signal representative of time varying cardiac tissue motion or blood flow (Q) with sensed signals from a left atrial appendage during atrial fibrillation juxtaposed to left upper pulmonary vein.

FIG. 3A shows a graph of a set of time varying signals of epicardial pressure;

FIG. 3B shows input of the set of time varying signals into a device agnostic computing system; and FIG. 3C shows output of haptic signals to a haptic interface.

FIG. 4A shows a schematic representation of a deformable haptic surface/shell for communication of tissue deformation and biophysical signals;

FIG. 4B shows a graph of tissue deformation (transeptal puncture=Pu) of FIG. 4A; and FIG. 4C shows a graph of pressure data (left atrial pressure=LAP) of FIG. 4A.

FIGS. 23A and 23B show anatomical representations of the heart used to transduce signals from a structural heart procedure (e.g., TAVR).

FIG. 23C a schematic representation of an embodiment of a haptic sleeve system with a a haptic hand (right oriented) relative to the anatomical representation of FIGS. 23A and 23B.

FIG. 28C shows haptic timing of FIG. 28B and depicts time of transeptal puncture;

FIG. 28D shows haptic timing of FIG. 28B and depicts event Ev1 related to palpation of left atrial pressure, LAP prior to mitral valve replacement;

FIG. 28E shows haptic timing of FIG. 28B and depicts time deployment of the guide for the valve dock prior to mitral valve replacement;

FIG. 28F shows haptic timing of FIG. 28B and depicts time of deployment of actual dock prior to mitral valve replacement;

FIG. 28G shows haptic timing of FIG. 28B and depicts time of rapid ventricular pacing prior to and during mitral valve deployment;

FIG. 28H shows haptic timing of FIG. 28B and depicts time of successful positioning and implantation of mitral valve deployment; and FIG. 28I shows haptic timing of FIG. 28B and depicts post mitral valve implant measurements of LA pressure.

Figure 1A:
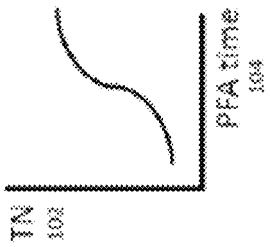
FIGS. 1A-1E are graphs showing examples of acquired input signals utilized by a haptic system in accordance with various embodiments, including.
Figure 1B:
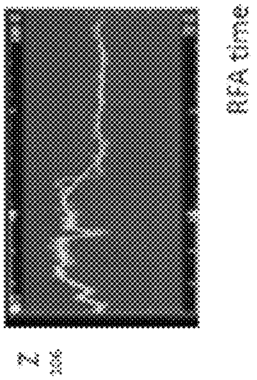
Figure 1C:
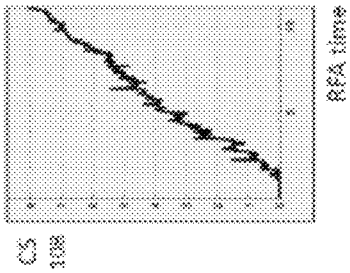
Figure 1D:
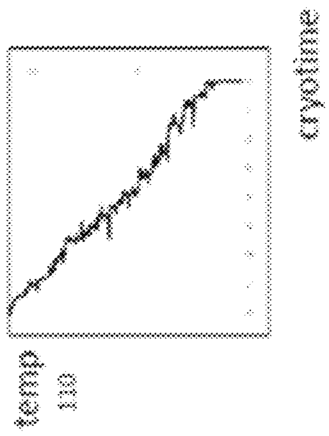
Figure 1E:
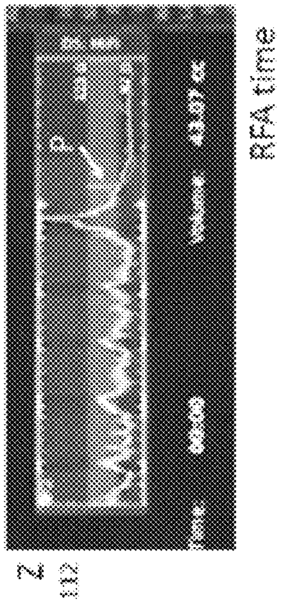

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Various embodiments of the present disclosure relate generally to a tactile/force (haptic) feedback system that is capable of acquiring static, quasistatic, and dynamic physiological/biophysical data from various sensors and generating real time simulations of signals produced by the heart and surrounding structures. More particularly, embodiments of the haptic system employ signals detected by varying contact and non-contact sensors as to provide the operator with holographic somatosensory information (e.g., along an extremity and/or other body part) that innervates/conducts neurologic impulses to various regions of brain, including the parietal lobe in the cerebral cortex, forming a real time haptic representational map of the heart or a haptic homunculus in real time. This is accomplished by transducing sensed signals from various sensors (e.g., at the distal end of an inserted catheter, via externally located imaging equipment, 3D electroanatomic navigational systems) into tactile and/or force sensations that are palpable, ideally in a holographic format preserving the depth, parallax and other properties of the actual tissue generating physiologic signals. This methodology serves to innervate separate yet contiguous anatomical divisions of an operator's sensory cortex in the postcentral gyrus for detection of sensed physiologic and biophysical signals that are likewise acquired from anatomically contiguous structures from within a given patient's cardiovascular system during an interventional procedure. Specific anatomic locations are represented as larger regions in the sensory homunculus and in embodiments of the disclosure special consideration is taken to display specific haptic signals to the user's body parts that have more numerous sensory innervation/connections (e.g., fingertips) and other haptic signals (kinesthetic, proprioceptive) to anatomic sites with less complex/numerous sensory connections.

In some embodiments, a wearable haptic interface (e.g., to be fitted on the hand and/r arm) provides tactile and force feedback to a user and is an anatomic and physiologic representation of the human heart constructed to provide an immersive augmented real time and virtual reality experience for procedural quality assurance purposes during cardiac interventions, and as an educational tool. In one mode of the present disclosure, the system uses a skeuomorphic design for purposes of creating a virtual haptic experience simulating the real-world experience of palpating the heart and surrounding structures through an open chest (a palpable cardiac digital twin) with associated visual displays during interventional cardiovascular procedures. Non-invasive monitoring of central and/or peripheral nervous system impulses is used to evaluate a user's haptic motor reaction time, system functionality, and identify delays in both system signal processing and a user's neurologic and procedural performance, cognitive status, and attention deficits. Machine learning and artificial intelligence (AI) are implemented to identify optimal means for sensing, signal processing, and haptic transduction for both novice and experienced operators by aggregating data from a multitude of haptic systems being used for training and medical interventional applications.

It is known that visual and auditory attentional resources of an operator, such as a surgeon, quickly saturate during repetitive tasks including prolonged medical procedures or cardiovascular interventions such as ablation of complex cardiac arrhythmia (ventricular tachycardia, ectopic atrial tachycardia, atrial fibrillation) and catheter-based valve repair/replacement. The same holds true for sense of touch, attentional resources fatigue when repetitive afferent signals lead to saturation of post-synaptic receptors in both the peripheral and central nervous systems. Medical catheters, instruments, and sheaths are generally tubular shaped and of a sufficiently small diameter to be inserted into a patient's body through a small incision, puncture, or a natural opening. Such catheters can be used to deploy inner catheters, cardiac leads, and electrodes, deliver contrast (e.g., radiopaque dye) or ablative energy and perform diagnostic or therapeutic procedures. Examples include a cardiovascular interventional system for ablation of tissue/cardiac arrhythmia, valve repair/replacement, pacemaker lead extraction, colonoscopy, laparoscopic, orthopedic or thoracoscopic procedures. Unfortunately, as conventionally designed catheters and tools course through a patient's tissues the operator loses his or her ability to appreciate the forces restricting motion secondary to attenuation and frictional effects and due to the intervening tissue and compliant nature of the inserted catheters. There remains an unmet need for a haptic system that can input, process, and output tactile and force feedback to an operator from dissimilar sensors that may be used during the time course of a single procedure.

Ablation of cardiac tissue for treatment of arrhythmias such as atrial fibrillation requires different procedures for the same intervention all of which may be performed with equipment supplied by multiple vendors; transeptal puncture to access the left atrium, catheters for ablation of cardiac arrhythmia, deployment of prosthetic valves or left atrial appendage occlusion devices. These interventions require the appropriate degree of tissue: catheter contact to ensure procedural success without risk of damaging or perforating neighboring tissues or perforation of the heart.

While current state of the art technology can display localization data (e.g., fluoroscopy, electroanatomic mapping), values of force and pressure, changes in tissue impedance and measured tissue voltage (electrogram amplitude/signal), there is an unmet need for how to convey a sense of touch/feel effectively and efficiently to the operator/surgeon. For haptic feedback to be present during specific phases of the same procedure sensed signals will need to communicate static, quasistatic, and time varying events. This may include time of transeptal puncture (a static single impulse biophysical signal), time varying changes in atrial pressure, tissue: catheter contact force during ablation (e.g., quasistatic measurements of tissue impedance); differentials in measured voltage/electric current; contact force sensing from one or more fiberoptic sensors, contact force sensing from strain gauges or other mechanical sensors of force; tissue temperature; reflected light.

Unfortunately, no currently available technology is capable of haptic feedback with a unified, device agnostic system capable of functioning seamlessly with dissimilar technologies and, of significant importance, nor are they able to prevent saturation of peripheral and central nervous system attentional resources. Various embodiments as disclosed teach methodologies to innervate separate yet contiguous anatomical divisions of the sensory cortex, monitor motor reaction times and procedural efficacy, and provide novel haptic feedback mechanisms that limit saturation of attentional resources of the operator/surgeon.

In various embodiments, it is important for sensed physiological and biophysical information to be accurately represented and processed in a timely fashion as to minimize latency between time of signal origin and haptic presentation. A multitude of sensed signals can be analyzed and cross correlated to confirm acquisition and proper interpretation of biophysical, physical, anatomical, physiologic data sets in real time. Those experienced in the art understand that variations in impedance, localized cardiac electrogram properties (amplitude, morphology, etc.), and assessments of tissue temperature may be erroneous.

In various embodiments, the haptic system utilizes algorithms to detect and correct inaccurate data sets prior to transduction of tactile and/or force information to an operator/surgeon. By way of example, whether it be analyses of voltage or current magnitude, frequency, phase, signals in the time or frequency domain, direct or calculated impedance; impedance slope, phase, magnitude; admittance, phase differences in measured voltage and current, the haptic system is capable of inputting data, processing, deriving, and conveying such data in both a visual and haptic format. Such data may include salient information about the magnitude of applied catheter force, the amplitude of energy being delivered, tissue temperature, and markers of acute or chronic tissue injury. Such algorithms can, for example, utilize reference electrodes and compare real time acquired data to those sensed by contact electrodes to confirm accuracy. Predictor algorithms can analyze the acquired signals and compare them to historical controls/data sets. If erroneous data is identified by any means (e.g., a catheter has stable contact with tissue; whereas saline irrigation used to cool tissue during ablation modifies impedance data) the system can pause haptic feedback or make modifications and corrections to the haptic feedback utilizing the appropriate signal for haptic processing and transduction.

By way of example, electroanatomic information about catheter electrode location relative to tissue of interest (i.e., in three dimensions) may demonstrate no change in location and comparable motion patterns of the catheter relative to contractile cardiac tissue and serve to confirm that tissue contact has not changed. Likewise, the magnitude, slope, phase, and other properties of intracardiac electrogram signals, impedance, etc. remain stable and confirm stable tissue contact force and thus prevent a change in the quantity or quality of haptic feedback that would occur should the system depend on only one erroneous variable that may otherwise indicate, for example, instability of contact sensing electrodes. In various embodiments, one or more signals can be analyzed to cross-correlate and confirm the accuracy of sensed signals that are to be processed for transduction of haptic feedback. Any correction to how the acquired signals is analyzed prior to haptic transduction are completed with minimal latency and, if possible, adjustments made continuously rather than at discrete time frames (e.g., every 50 milliseconds).

In various embodiments, temperature-based techniques may be used in place of or in addition to non-temperature-based methods (e.g., nature and intensity of voltage signals, differential voltage properties/amplitudes between differing electrode combinations) for determining physical and physiologic properties such as tissue necrosis and tissue catheter contact (force). For example, analysis of thermocouple trends from different catheter locations can provide information representative of tissue contact, thermal injury, and the like at different time frames of a given procedure (e.g., during catheter manipulation vs during delivery of ablation energy, when a catheter is in one specific position/orientation). A precipitous drop in measured tissue temperature may occur due to loss of tissue contact rather than tissue cooling naturally or from delivery of cryoablation energy. Change in temperature over time (dT/dt), can be used to differentiate between different physical conditions. If multiple indices are analyzed to determine the accuracy of any acquired data, certain indices may be weighted higher as being more specific and sensitive than others.

In various embodiments, a default correction system is programmed, or an operator can modify the algorithms (e.g., how different signals are weighted) based on personal preferences or expected physiologic/anatomic conditions (e.g., patient with prior ablation may have more regions of tissue necrosis that affect baseline impedance and an alternate sensing index may be selected). If the operator is using an ablation catheter that has high resolution electrograms from tip electrodes separated by material with high thermal diffusivity or other particular properties he or she may rely more heavily on the impedance or electrogram data acquired to determine, for example, when an ablation is completed rather than tissue temperature.

In various embodiments, the delivery of a haptic signal specific for communicating that the target degree of tissue necrosis has occurred is based on sensing of the most reliable signal(s). The system has a correction algorithm that quantifies a variety of relevant signals in real time including catheter tissue contact force, tissue temperature or analysis of tissue necrosis and cross correlates data as to confirm accurate representation of biophysical and physiologic information (e.g., based on the nature or relative amplitude of measured electrogram signals in different locations about an inserted catheter). The correction algorithm can analyze differing signals as described above as well as features of the same signal (e.g., voltage waveform) for confirmation that acquired data is accurate before transduction of sense signals as haptic feedback. As a simple example, impedance trends may not be accurate during application of radiofrequency energy for determination of tissue contact and one or more of contact force sensing, tissue temperature trends, and/or electrogram voltage characteristics are input for data processing and delivery of haptic feedback rather than impedance data. In some embodiments, artificial intelligence (AI) and/or machine learning (ML) techniques may be implemented to optimize signal analyses and transduction of sensed signals into haptic feedback.

Figure 7:
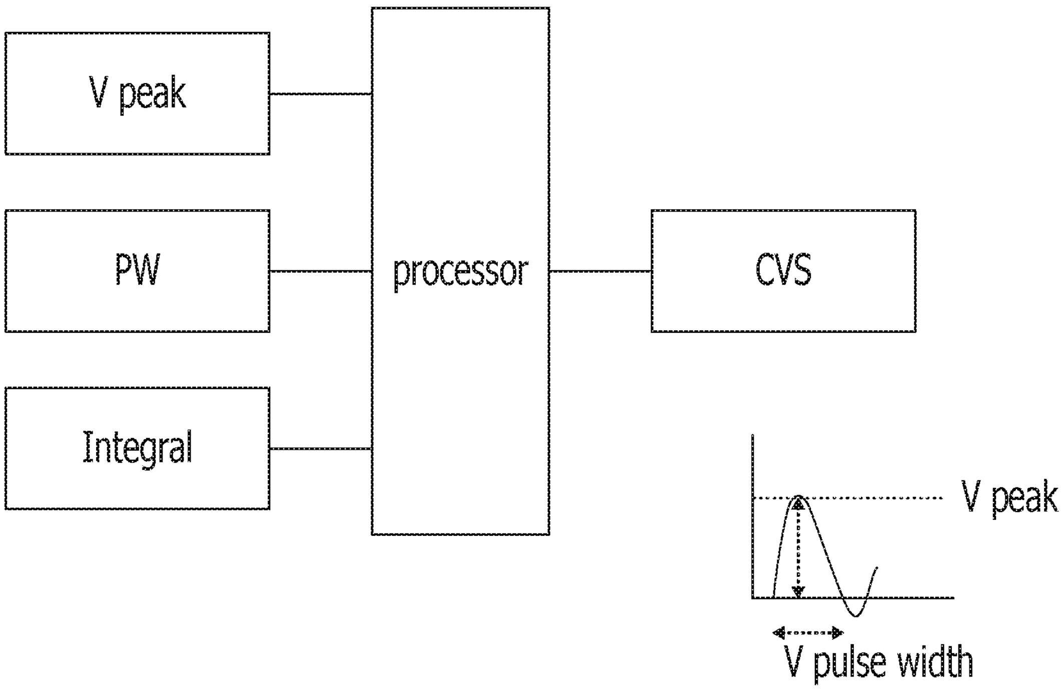
FIG. 7 shows a schematic diagram of a voltage variable input data system in accordance with various embodiments.

In various embodiments, differing characteristics of a single variable can also be analyzed as to determine accuracy of the variable as input for processing and delivery of haptic feedback. Electrogram voltage amplitude, pulse width, as well as frequency characteristics can be analyzed and processed in processor 708 as depicted in FIG. 7. By way of example, the same voltage waveform is analyzed, and the pulse width of the signal is used to derive part or whole of the contact voltage sensing index at 712 rather than peak voltage amplitude as a single variable. A combination of pulse width and amplitude may be used, and in an embodiment, the integral of the voltage waveform between two or more electrodes (example) over one or more discrete time frames is the input variable. High amplitude voltage (e.g., 3 mV) with a brief pulse width (e.g., 0.5 mV) suggests inadequate tissue contact, while both high amplitude voltage (2 mV) and longer pulse width (e.g., 0.5 mV) is an indicator of adequate tissue contact and specificity may be greater than measurements of tissue impedance, temperature, or other variables. Frequency spectra or other features of the voltage signal (e.g., electrogram morphology) can be analyzed as well.

In various embodiments, the same signal can also be used to determine tissue contact as well as degree of tissue necrosis. By way of example, after delivery of ablation energy, relative voltage amplitude between two or more electrogram signals can be analyzed to determine if adequate tissue necrosis has occurred. This relative voltage amplitude can be used as a single variable or in another embodiment weighted amongst multiple variables such as tissue impedance, temperature trends/characteristics at one or more locations, reflected light characteristics and the like. The system can evaluate relative changes in one or more variables from reference values rather than absolute values to determine if tissue is viable, diseased (e.g., infarcted, or partially ablated), or necrotic tissue. In one embodiment, both the degree of tissue contact, and determination of adequate tissue necrosis are transduced as different haptic signals that can be readily differentiated by the operator (e.g., tactile and force feedback, respectively). By way of example, a tactile signal is palpable and proportionate to the degree of tissue contact and a force signal is proportionate to the degree of tissue necrosis.

In various embodiments, this layered haptic display will prevent saturation of haptic attentional resources. The haptic display in one embodiment is a non-rigid haptic interface such as a piezo actuator having a thickness of less than 5 mm and surface area under 2 cm that can conform and wrap about a catheter handle or be worn on the hand, wrist, arm, forearm, finger(s) or other body part of the operator.

In some embodiments, for effective ablation of tissue to be accomplished catheter tip orientation should be optimal. In an alternate embodiment of the present disclosure, there is haptic representation of catheter tip orientation based on one or more variables (e.g., electroanatomic mapping data, relative temperature/impedance/voltage amplitude of proximal and distal electrode pairs). This haptic data may be presented as a distinct haptic signal that can be differentiated from other haptic signals. By way of example, circumferential deformation of a piezo actuator or other haptic signal is uniform when catheter tip orientation is optimal (perpendicular to the tissue plane) or has a proportionate gradient in degree of deformation (e.g., 0-90 degrees) when orientation is oblique so the operator can modify the position in real time based on sense of touch.

Referring to FIGS. 1A-1E, one or more sensed signals are acquired and input into the haptic computing system. Static signal as shown in FIG. 1A for a tissue necrosis indicator level can be derived by one or more sensed signals including tissue temperature, reflected light, reflected ultrasound, electrical impedance, voltage, current, changes in measurements from devices capable of electroporation of tissue (e.g., pulsed field ablation). Once a threshold value is reached the system delivers a haptic signal that is proportionate to the degree of tissue necrosis. The haptic signal may be a single or series of tactile and/or force feedback indicators including but not limited to; actuator vibration that implements psychophysical haptic rendering techniques to simulate tissue temperature, deformation of a haptic actuator on the hand, finger or other anatomic site, generation of force feedback (e.g., linear actuator), tactile feedback. In some embodiments, the haptic system processes static signals and generates a haptic signal at a pre-specified cycle length independent or dependent and proportionate to the cardiac or respiratory cycle or other time varying haptic output as described in more detail below and seen in FIG. 10 (e.g., can implement amplitude or frequency modulation to convey certain features of the sensed signal such as the degree of decrease or increase in temperature, indicator of tissue injury).

Figure 10:
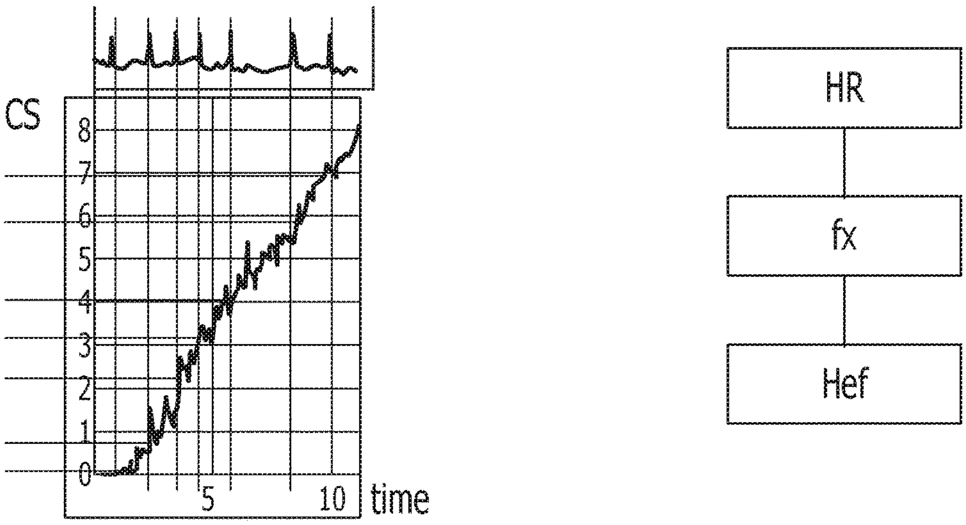
FIG. 10 shows a schematic representation of an embodiment of gating of static and quasistatic signals proportionate to cardiac cycle in patient with atrial fibrillation.

Similarly, quasistatic signals as shown in FIGS. 1B-1E are acquired and input into the haptic computing system that outputs one or more haptic signals to a user. By way of example, the haptic system can process the quasistatic signal and generate a haptic signal at a pre-specified cycle length independent or dependent and proportionate to the cardiac or respiratory cycle (FIG. 10). This enables a signal that is not time varying to be processed and generate a time varying haptic signal that has both biophysical (e.g., impedance) and physiologic properties (e.g., simulates cardiac cycle) and is generated by a single haptic actuator (e.g., a linear or rotary motor that generates force feedback with periodicity). For force feedback to be rendered palpable as force or pressure, the haptic system operates in an optimal fashion with a cycle dependent haptic feedback mechanism (e.g., linear actuator) that may be gated and proportionate to heart rate. In an alternate embodiment, the haptic actuator provides non-cyclical feedback to the operator including deformation at a proportionate amount of displacement (e.g., piezo actuator). Some sensed signals may be both quasistatic and dynamic as is demonstrated inf FIG. 1E where a dynamic, time-varying signal of tissue impedance is noted while the catheter is in contact with contractile tissue (e.g., mitral annulus, left ventricle, left atrial appendage) and then static when in contact with another anatomic sites (e.g., atrial tissue, pulmonary vein).

In various embodiments, the haptic system can employ both a time varying force feedback to the operator and static haptic feedback such as displacement or utilize a time varying force feedback that is gated 1:1 or other ratio (e.g., 2:1, 3:1) relative to the cardiac cycle (or other cycle lengths) as depicted in FIG. 10. In this embodiment, the ECG tracing is input into the haptic system and triggers the haptic force feedback coincident with each electrical depolarization (e.g., surface R wave, IEGM signal) which will be described in more detail below.

Figure 2A:
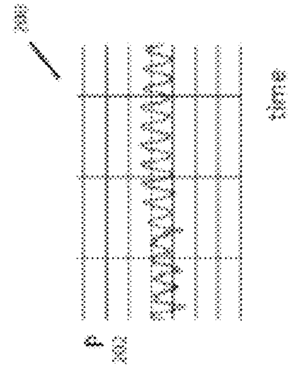
FIGS. 2A-2C show examples of dynamic input signals utilized by a haptic system in accordance with various embodiments, including.
Figure 2B:
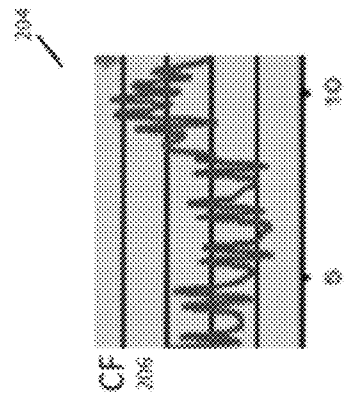
Figure 2C:
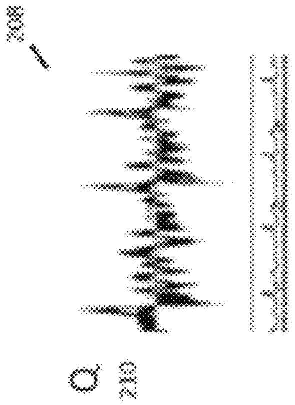

Referring to FIGS. 2A-2C, in various embodiments three different physiologic signals are acquired during a complex intervention for ablation of the pulmonary veins and obliteration of the left atrial appendage (e.g., Watchman). These procedures are performed in order to protect a patient from cardioembolic stroke and requires multiple independent steps each of which enable acquisition of time varying signals from different anatomic sites, transeptal puncture, radiofrequency ablation about the pulmonary veins, deployment of a Watchman device in the left atrial appendage. Transeptal puncture (required for gaining access to the left atrium) utilizes a catheter with end hole manometry that measures left atrial pressure (time varying). The left atrial pressure signal shown in FIG. 2A is input into the computing system which processes and outputs the haptic signal driving the actuator which generates force feedback to the operator with a 1:1 ratio to the cardiac cycle. Next, ablation about the pulmonary veins is performed using radiofrequency energy and the computing system inputs contact force shown in FIG. 2B as the time varying signal and again processes and outputs the haptic signal driving the actuator generating force feedback to the operator with a 1:1 ratio to the cardiac cycle. Finally, the operator deploys the Watchman device in the left atrial appendage (LAA) and blood flow sensors (e.g., Doppler flow wires) or tissue motion sensors detect that the device is opposed to the LAA confirming accurate placement; the haptic system inputs blood flow/tissue motion (Q) as the time varying signal shown in FIG. 2C, and again processes and outputs the haptic signal driving the actuator generating force feedback to the operator with a 1:1 ratio, but at a higher frequency as the sensed signal is over 200 cycles per second due to a fibrillating LAA. This signal has a time varying periodicity, variable amplitude signals and is palpably distinct from other time varying signals.

Figure 3A:
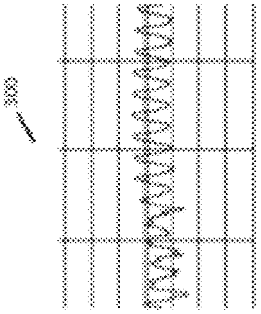
FIGS. 3A-3C show examples of an input, processing, and output of time varying signals utilized by a haptic system in accordance with various embodiments, including.
Figure 3B:
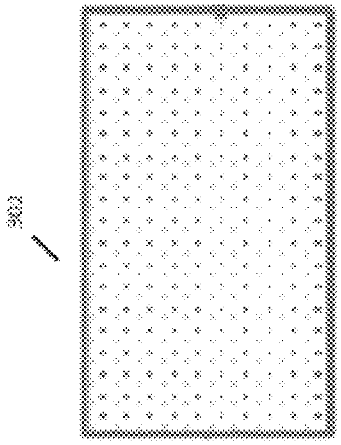
Figure 3C:
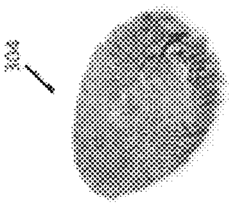

In various embodiments, the same computing system can receive varying input signals, process them accordingly, and output the haptic response as shown in FIGS. 3A-3C. In this example, epicardial pressure is the input signal during access to the epicardial space for ablation of ventricular tachycardia.

Figure 4A:
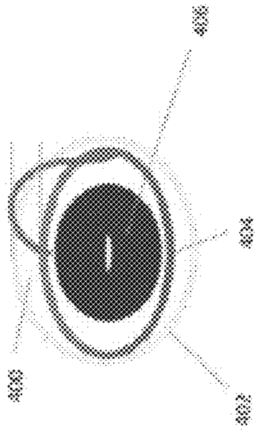
FIGS. 4A-4C show examples of a device agnostic multimodal haptic interface in accordance with various embodiments, including.
Figure 4B:
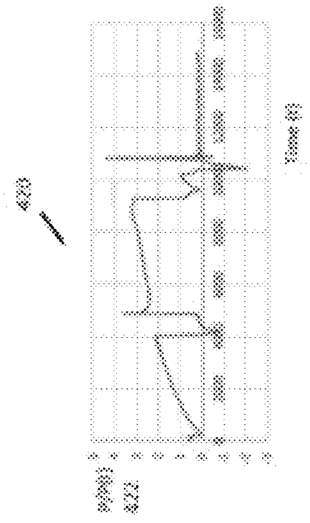
Figure 4C:
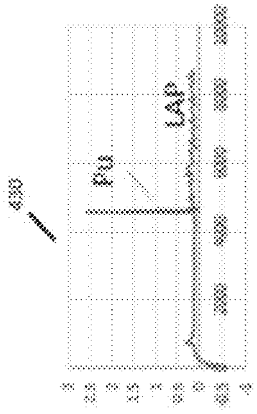

FIGS. 4A-4C depict both a piezo actuator (Pz in FIG. 4A) based haptic feedback system that provides deformation information to the operator. This deformation can be implemented to convey static information to the operator. By way of example, the tactile feedback is representative of the degree of tissue deformation and proportionate to the pressure head (P) from a catheter opposed to the interatrial septum during transeptal puncture as shown in FIG. 4B. In this example, the intracardiac pressure signal acquired by a catheter with end hole manometry as shown in FIG. 4C can be used to provide tactile information to the operator as the catheter is manipulated within the left atrium and opposed to the septum with different amounts of applied force and degree of septal deformation, PZ (1). This is distinct to the time varying pressure waveform acquired when the catheter is free floating in the left atrium (LAP) after puncture (Pu) of the septum.

Figure 5:
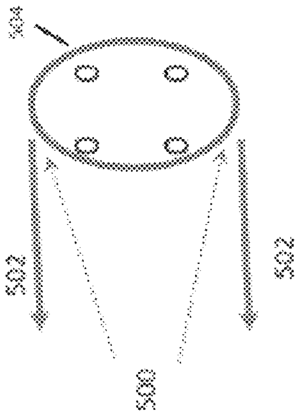
FIG. 5 shows an embodiment of a haptic system for pulsed field ablation system for atrial fibrillation and sensing of tissue necrosis.

FIG. 5 illustrates pulsed field ablation about the pulmonary veins as is known by those experienced in the art. The degree of tissue necrosis (TN) is measured and conveyed to the operator in a haptic format. This can be accomplished with haptic rendering techniques to simulate temperature (e.g., psychophysical haptic rendering) by imparting a high frequency vibration tactile signal where the change in frequency leads the user to sense an increase in heat (due to an increase in high frequency haptic feedback). The extent of tissue necrosis can be measured by assessment of intracardiac electrical properties (e.g., electrogram amplitude, impedance changes), tissue temperature trends/data, or means for tissue characterization (e.g., properties of reflected ultrasound or light). The same haptic computing system can input varying signals and output the appropriate haptic response(s).

Figure 6:
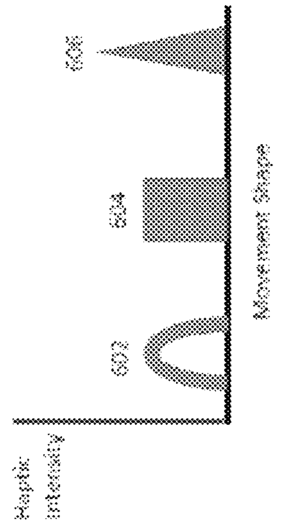
FIG. 6 shows varying haptic waveforms/transients used in accordance with various embodiments to prevent deficits in haptic attentional resources.
Figure 8:
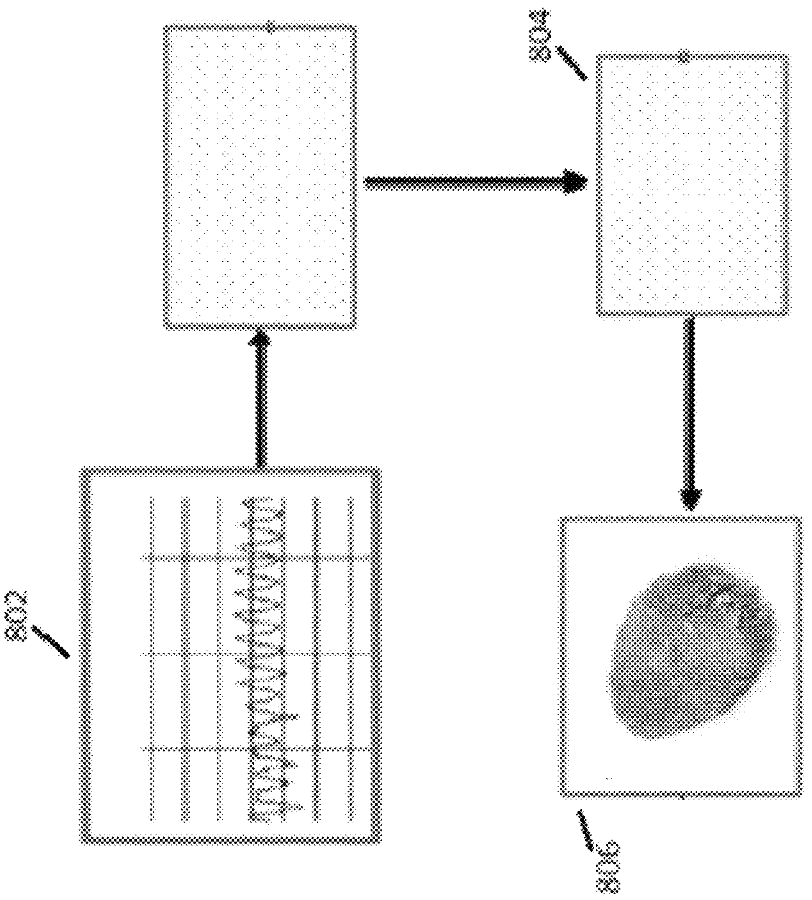
FIG. 8 shows a schematic diagram of variable haptic signal generator in accordance with various embodiments.

During lengthy cardiac interventions, visual, auditory, and sense of touch attentional resources become saturated. To mitigate the saturation or fatigue of post-synaptic receptors in both the peripheral and central nervous systems the haptic system varies the type of haptic feedback signal generated by modifying the haptic intensity and sharpness for each haptic effect over time as shown in the examples presented in FIG. 6 using a variable haptic signal generator 800 as shown in FIG. 8 that accepts input signals at 802, processes data at 804 and output haptic feedback at 806. By way of example, referring to FIG. 6, the action of a given actuator (e.g., haptic speaker, linear motor) is modified to displace over time with sharp, precise, or rounded movement such that the degree of displacement, acceleration, deceleration of the element varies providing a distinct haptic sensation with essentially the same information relevant to the measured physiologic or biophysical signal that is sensed (e.g., tissue displacement over time during transeptal puncture, change in contact degree over time).

Figure 9A:
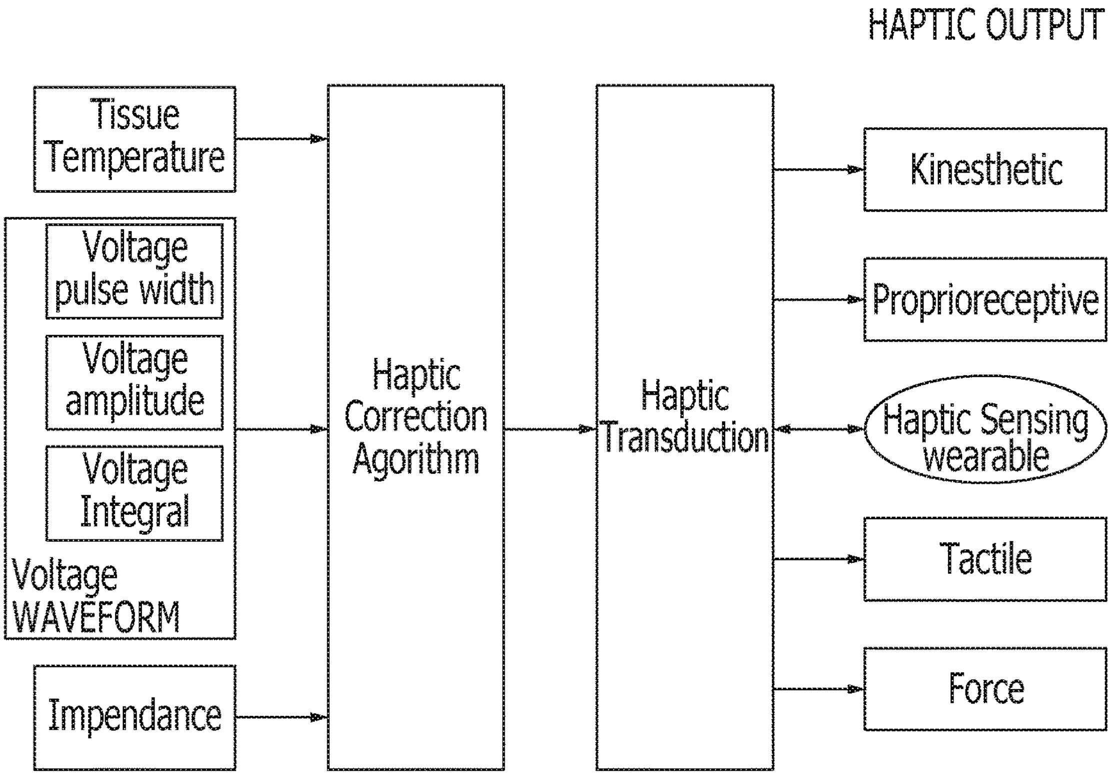
FIGS. 9A and 9B show schematic diagrams of an embodiment of a reciprocating haptic sensory glove/rings/wristband incorporating sensors (e.g., accelerometer, gyroscopic sensor, piezosensors) that detect actions of the operator and relationship to biophysical/physiologic events (e.g., delivery of RFA energy, transeptal puncture) in accordance with various embodiments.
Figure 9B:
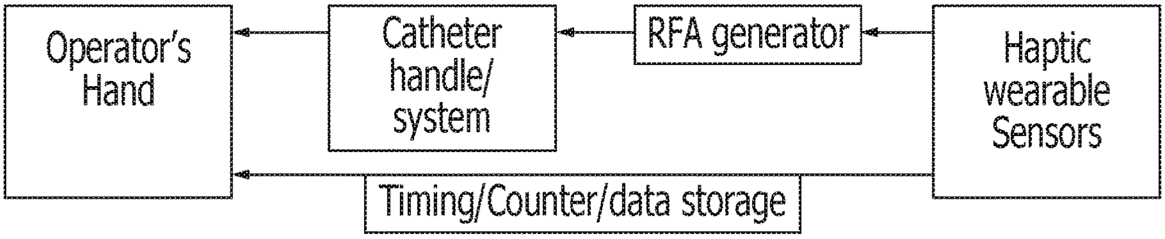

In an alternate embodiment, internally or externally deployed sensors (e.g., accelerometers, piezo sensors, gyroscopic sensors, etc.) located in or on the haptic interface sense timing of an operator's simple and complex handle/hand/finger motion and catheter manipulations relative to fiducial events (e.g., transeptal puncture, time between change in sensed signal representative of effective ablation (e.g., change in impedance, differential voltage, other sensing indicator of tissue necrosis, fluctuation in catheter: tissue contact force) and time of application or removal of applied ablation energy (e.g., delivery of PFA, cryogenic, or thermal energy, radiofrequency energy) or time of change in catheter position or other salient events. Timing intervals are stored and available for review and comparison to previous haptic motor reaction times from the operator and other interventionalists. The reciprocating haptic sensory glove/rings/wristband/sleeve incorporates sensors (e.g., accelerometer, gyroscopic sensor, piezo sensors) that detect actions of the operator and relationship to biophysical/physiologic events and therapies being delivered as depicted in FIGS. 9A and 9B (e.g., delivery of RFA energy, transeptal puncture).

Figure 11:
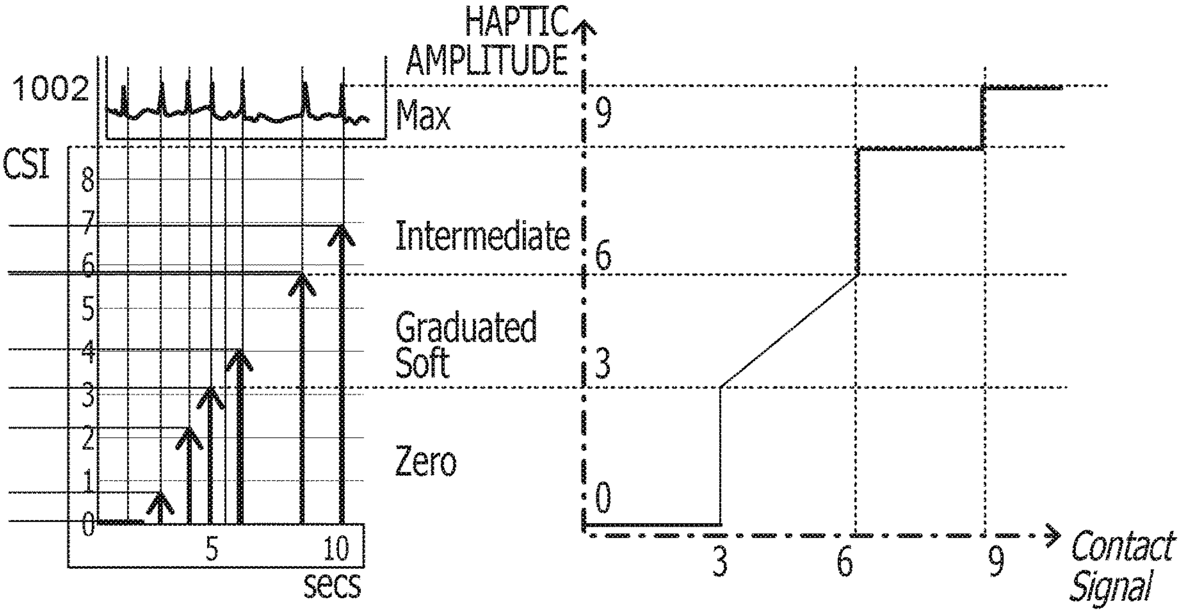
FIG. 11 shows a graphic representation that demonstrates an embodiment of gating of sensed signals to generate haptic effect based on cardiac cycle using step function with discrete rather than gradual increases in haptic effect (e.g., haptic force) based on magnitude of sensed signal (e.g., degree of contact sensing) and no haptic effect below a specific threshold (e.g., contact sensing signal value=3).
Figure 12:
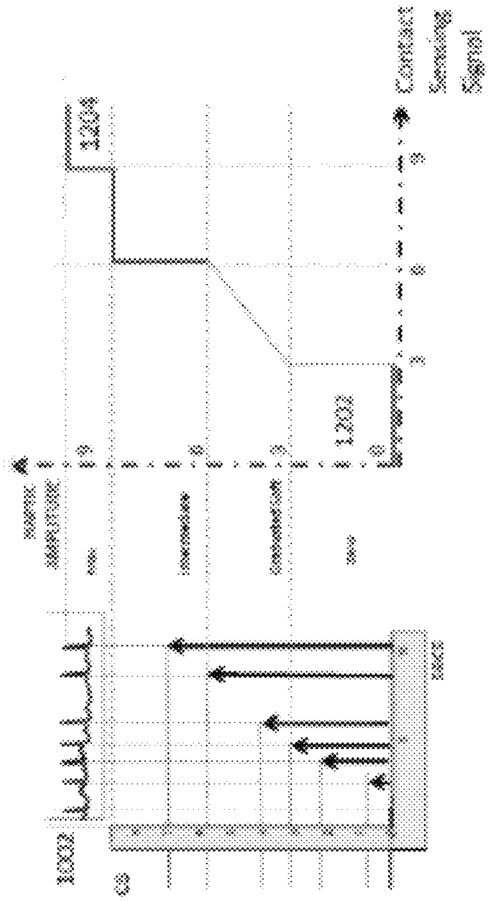
FIG. 12 shows a graphic representation of an embodiment of FIG. 11 with programmable haptic gain that can be adjusted after the case begins.
Figure 13:
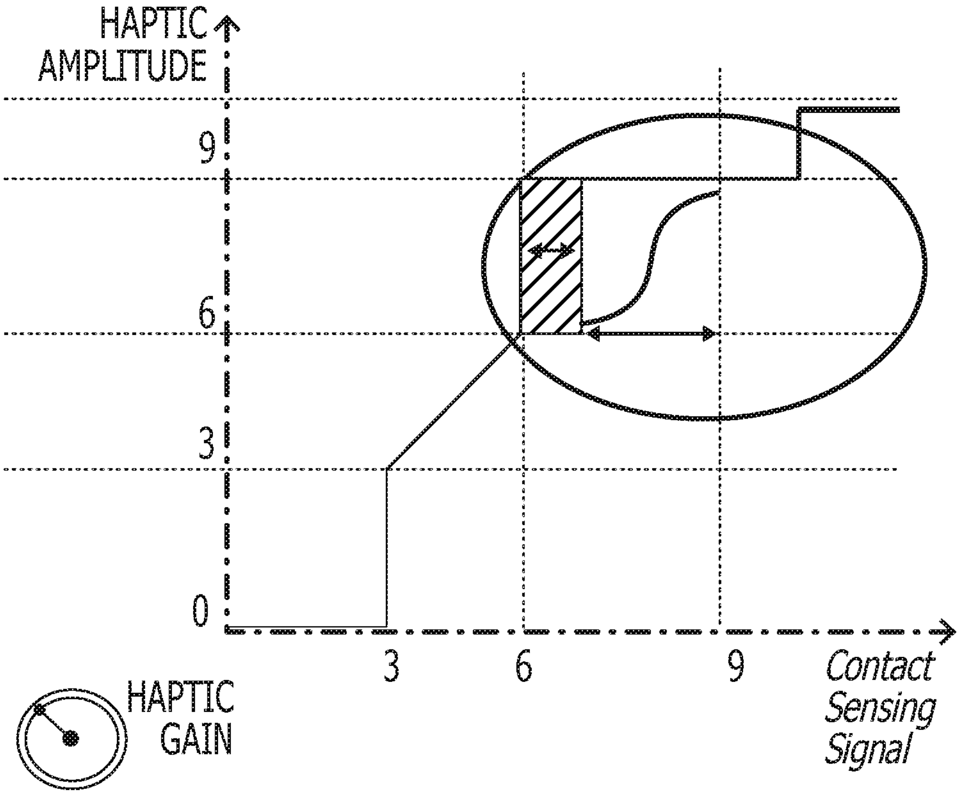
FIG. 13 shows a graphic representation of an embodiment in which temperature data is implemented as input to haptic system with a curvilinear relationship between temperature and degree of haptic effect that can be the same as when RFA is not applied, or modified in type of haptic effect, quality/quantity, and/or location of haptic effect (e.g. different anatomic location such as first 2 digits vs last 2 digits).
Figure 14:
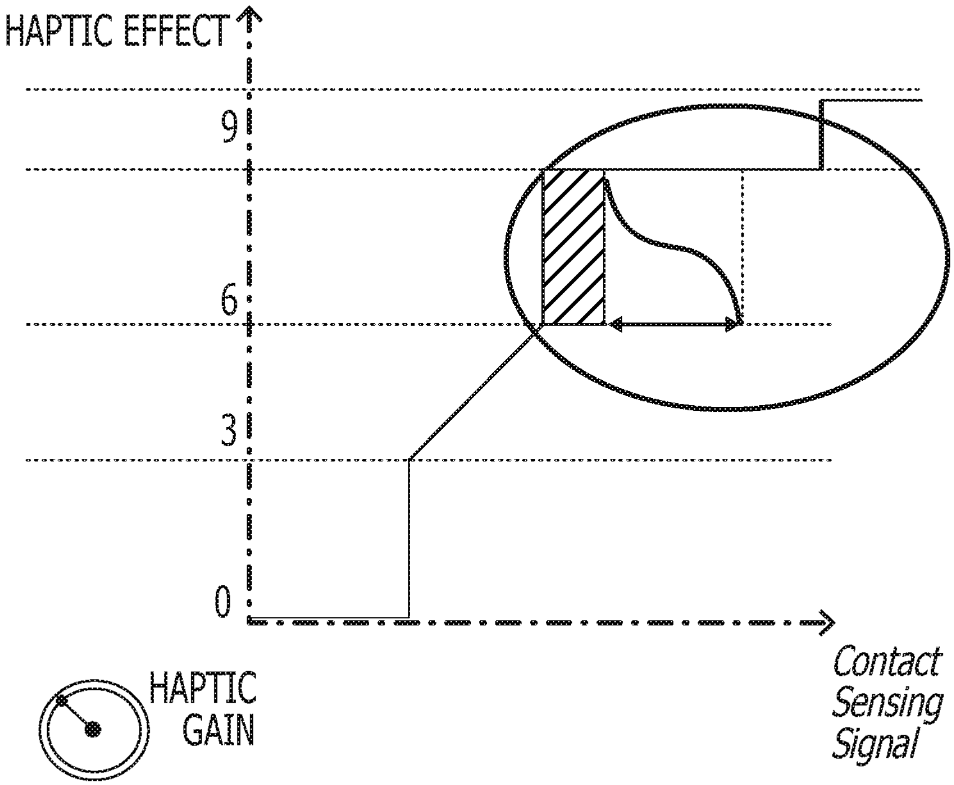
FIG. 14 shows a graphic representation of an embodiment of FIG. 13 but with haptic effect during RFA application is based on electrogram/voltage properties and has an inverse relationship with contact sensing signal data and electrogram voltage at distal electrodes is analyzed to assess degree of tissue necrosis (index of ablation success) rather than tissue contact (which would have a directly proportionate relationship to peak electrogram voltage).
Figure 15:
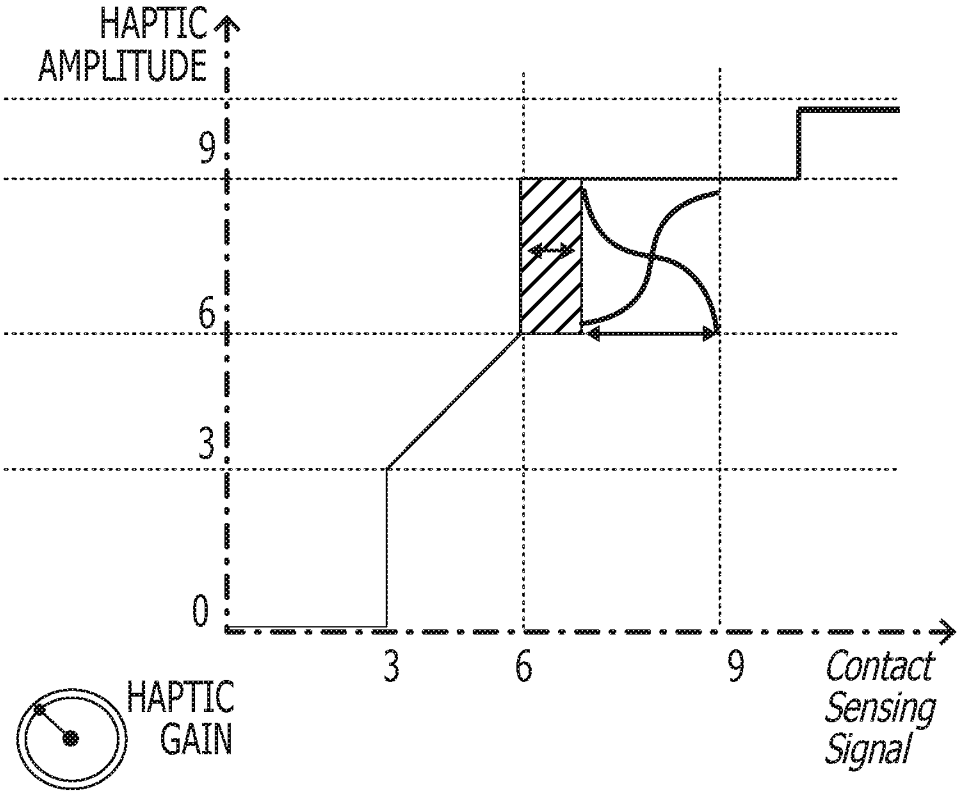
FIG. 15 shows a graphic representation of an embodiment that demonstrates multi-modal haptic effects related to temperature, EGM, contact sensing and relationship of these signals to haptic effect magnitude in a form of musical score for qualitative and quantitative description of frequency, amplitude, information.
Figure 16:
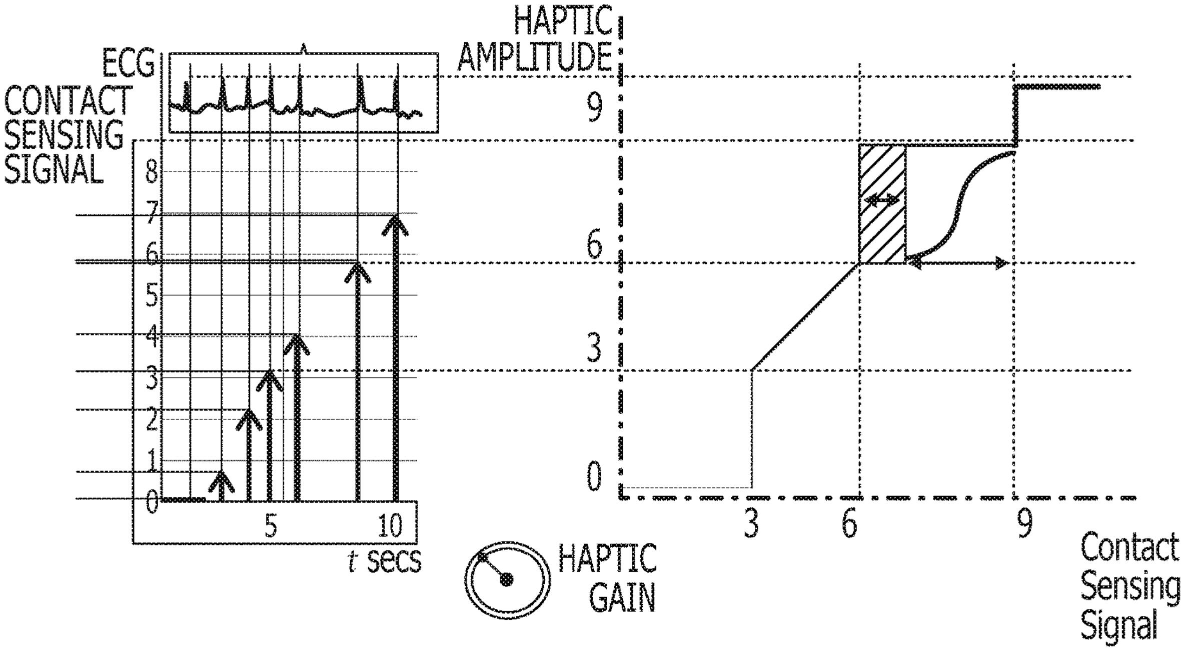
FIG. 16 shows a graphic representation of an embodiment of FIG. 15 with layered haptic effect such that temperature is manifest using psychophysical haptic rendering techniques (e.g., vibratory effect to simulate temperature) along with contact sensing index and electrogram data.

In some embodiments, there is gating of static and quasistatic signals at a 1:1 ratio with electrical depolarization or a multiple (e.g., 2:1) as programmed by a multiplier as depicted in FIG. 10 that adjusts the frequency of the haptic signal. Haptic feedback can be programmed to be linearly proportionate to the amplitude or magnitude of the sensed signal/index or as depicted in FIG. 11 as a step function, so that there are discrete incremental increases in magnitude of haptic feedback (e.g., force of linear motor, degree of deformation of haptic surface) that may be more readily interpretable by the operator. In various embodiments, no haptic effect can be programmed in certain situations even when there is an input signals (e.g., contact force<10 μm) as shown as 1202 in FIG. 12 and haptic gain adjusted to help the operator better differentiate if an adjustment is needed (e.g., in applied catheter force) as shown at 1204 in FIG. 12. Programmability can be more sophisticated and the operator can modify the input signal for haptic processing as depicted in FIG. 13 where an impedance based contact sensing signal is substituted for a tissue temperature index during application of radiofrequency energy or a layered haptic effect is provided that may include additional data related to other sensed signals such as EGM properties as illustrated in FIGS. 14 and 15. FIG. 16 illustrates the composite of using the multiplier and layered haptic effects based on multiple input signals.

Figure 17:
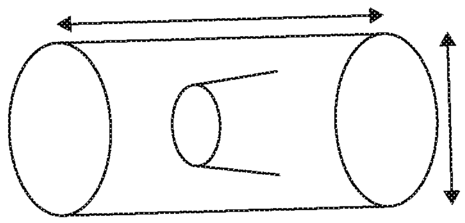
FIG. 17 shows a schematic representation of an embodiment of a haptic speaker (Sp) that generates a haptic force effect (e.g., contact sensing) encased in a cylindrical tube that has piezoelectric material (Pz) and deforms to generate a haptic tactile effect (e.g., tissue deformation, temperature, tissue necrosis).

In some embodiments the haptic signal is transmitted by one or more haptic speaker(s) (Sp) or voice coil(s) that generate(s) feedback below the frequency for audible signals and is enclosed in a shallow cylindrical unit that can be worn on the wrist, hand, arm, or other body part. Optimally, the haptic speaker unit is less than 1 cm in circumference and length as illustrated in FIG. 17 and serves to generate force feedback to the operator. In an alternate embodiment, the outer surface of the haptic speaker is a deformable semi-rigid haptic actuator (e.g., Young's modulus between 0.01 and 0.1 GPa) such as a piezoelectric surface (Pz) that deforms and provides tactile feedback to the operator and the unit generates both force and tactile information.

Figure 19B:
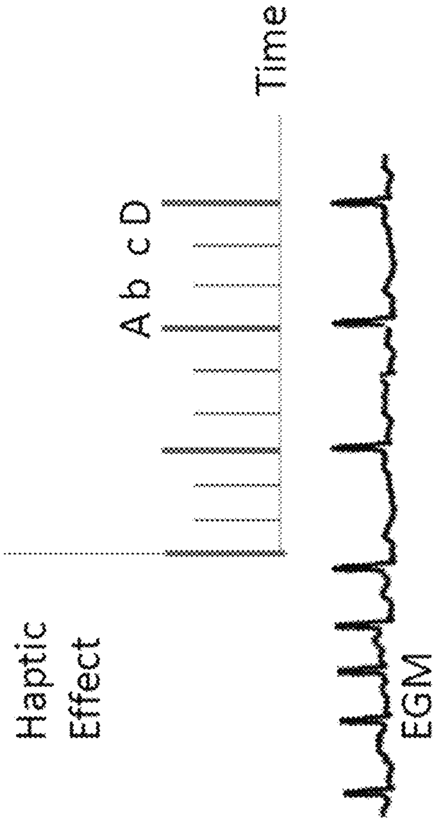
FIG. 19B shows a graphic representation of an embodiment of the amplitude of each haptic signal proportionate to the sensed signal amplitude so that the baseline haptic signal (rather than the multiplicative signals) appropriately generates the relative change in sensed signal amplitude.
Figure 19A:
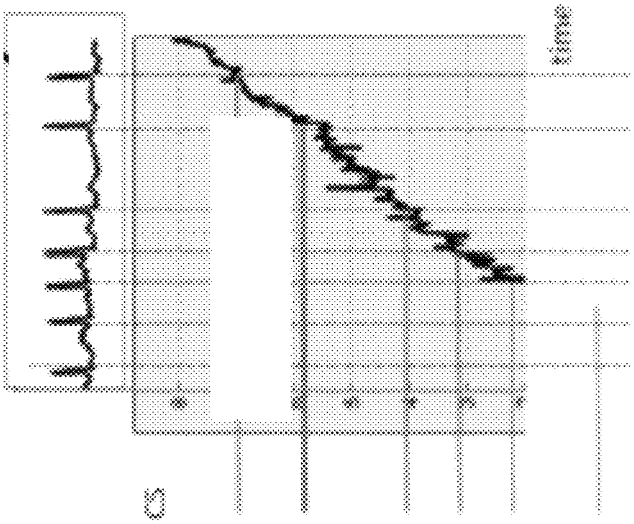
FIG. 19A shows a schematic representation of an embodiment of a haptic force effect of a haptic speaker delivered at the same cycle length/frequency of the cardiac cycle or a multiple proportionate to the cardiac cycle.

The haptic force effect of the speaker can be delivered at the same cycle length/frequency of the cardiac cycle or a multiple proportionate to the cardiac cycle as depicted in FIG. 19A at a rate or haptic frequency rate (HFr) of 180, three times the heart rate of 60 based on the programming of the haptic multiplier, fx. The amplitude of each haptic signal is ideally proportionate to the sensed signal amplitude or at least a proportionality is maintained so that the baseline haptic signal (rather than the multiplicative signals) appropriately generates the relative change in sensed signal amplitude as shown in FIG. 19B. The physiologic signal is a sensed signal and by way of example can be one or more of heart rate, inotropic state of the heart, intracardiac electrogram amplitude, blood flow velocity, intracardiac pressure, tissue motion characteristics, catheter: tissue contact force. In an embodiment, the haptic speaker or other haptic element (e.g., thin piezo actuator) is designed to conform in a concave fashion to a fingertip and generate tactile and/or force signals to the highly innervated distal most aspect (DMA) of the operator's finger. Any time of haptic actuator is within the scope and spirit of the present disclosure and may be implemented to achieve the same result and use of a haptic speaker is by way of example.

Figure 18:
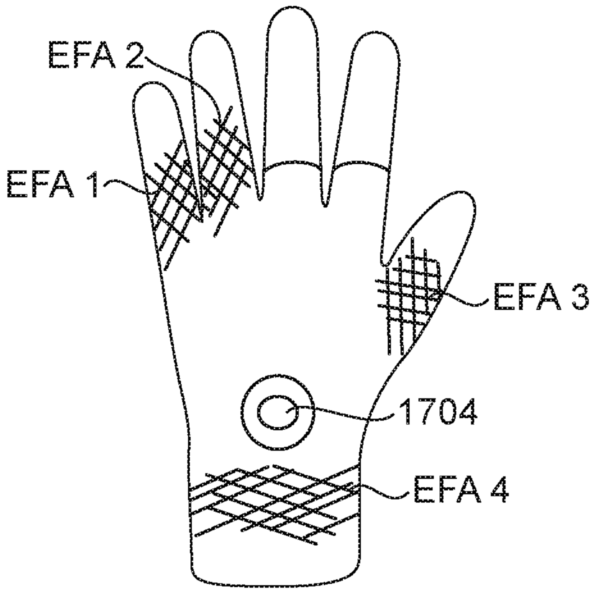
FIG. 18 shows a schematic representation of an embodiment of a haptic homunculus having a plurality of cylindrical tube elements for delivering representative sensed physiologic/biophysical signals and a wearable holographic haptic display.

In yet another embodiment, a wearable deformable haptic actuator (DeHA) is a cohesive stretchable polymeric support with electrically conductive elastomeric properties or comparable properties made of differing material/haptic properties. By way of example and depicted in FIG. 18, the DeHA incorporates one or more elastic force actuators (EFA) that in various embodiments are an elastic fibrous web intertwined with piezo actuator filaments with yams of about 500 to 2000 denier uniformly spaced at about 10-30 yams per 0.5 cm width and having a Young's elastic modulus such that there is less than moderate compression and comparable to human tissue such as tendon, skin, ligament (e.g., between 1.0 and 2.0 GPa) with comparable viscoelastic mechanical behavior and force-strain curves. As depicted in FIG. 18, EFA 1-3 are shaped as to conform to the base of one or more fingers (digital) and about the distal aspect of the hand or wrist (palmar or dorsal) at EFA4 and all provide tactile signals.

In embodiments, this DeHA is preferably fit with a subsonic (<20 Hz) haptic speaker Sp at B that provides force feedback and can also be fit with inaudible high frequency (>20 Hz) haptic speakers (not shown) that employ psycho-physical haptic rendering in one or more locations and provide sensory feedback such as temperature sensations. This complements the delivery of piezo actuator based haptic feedback in other locations providing a blended haptic feedback wearable device but to this present disclosure serves as a contiguous haptic display designed to function with the most distally located haptic actuator (e.g., at the fingertip) and innervate contiguous portions of the somatosensory cortex separate and apart from signals generated at the distal most aspect. In practice, the distal most actuator (DMA) provides signals from the distal most aspect of an inserted catheter and other actuators along the DeHA generate more proximal signals from signals sensed by an inserted catheter and/or non-contact sensors as explained in more detail below. In an embodiment, the catheter's sensor (s) generate(s) signals that are transduced in real time and represented along the operator's extremity (e.g., finger) sequentially in a distal to proximate location based on time and location/space so that previously detected signals are transduced in a haptic format more proximally along a finger, hand, wrist, arm or elsewhere and provide spatial and temporal information to the operator as the catheter is advanced into an alternate (e.g., deeper intracardiac) location. In this fashion, distinct locations of haptic actuation correlate to different anatomic locations and thus a different region of the somatosensory cortex (homunculus) as depicted in FIG. 18.

By way of example, during a transeptal puncture the biophysical signal of crossing the interatrial septum (TP) is rendered palpable by transduction of a pressure signal from a transeptal needle to DMA at the fingertip at the time of puncture. As the catheter tip is directed into the left atrium, left atrial pressure is palpable at the DMA while the sensation of the catheter's now more proximal location where the interatrial septum was located is rendered palpable coursing further back along the finger, wrist, forearm as the catheter is manipulated deeper into the left atrial cavity. This provides the operator with a holographic haptic sensation and innervates contiguous yet distinct portions of the somatosensory homunculus in real time. The haptic sensation that represents the changing location of the interatrial septum relative to the tip of the catheter moves more proximal along the finger, hand, wrist. This can be accomplished using piezo actuator filaments (PzF) in the EFW which wraps around, for example, the operator's digit or other aspects of a limb of the operator.

Figure 20A:
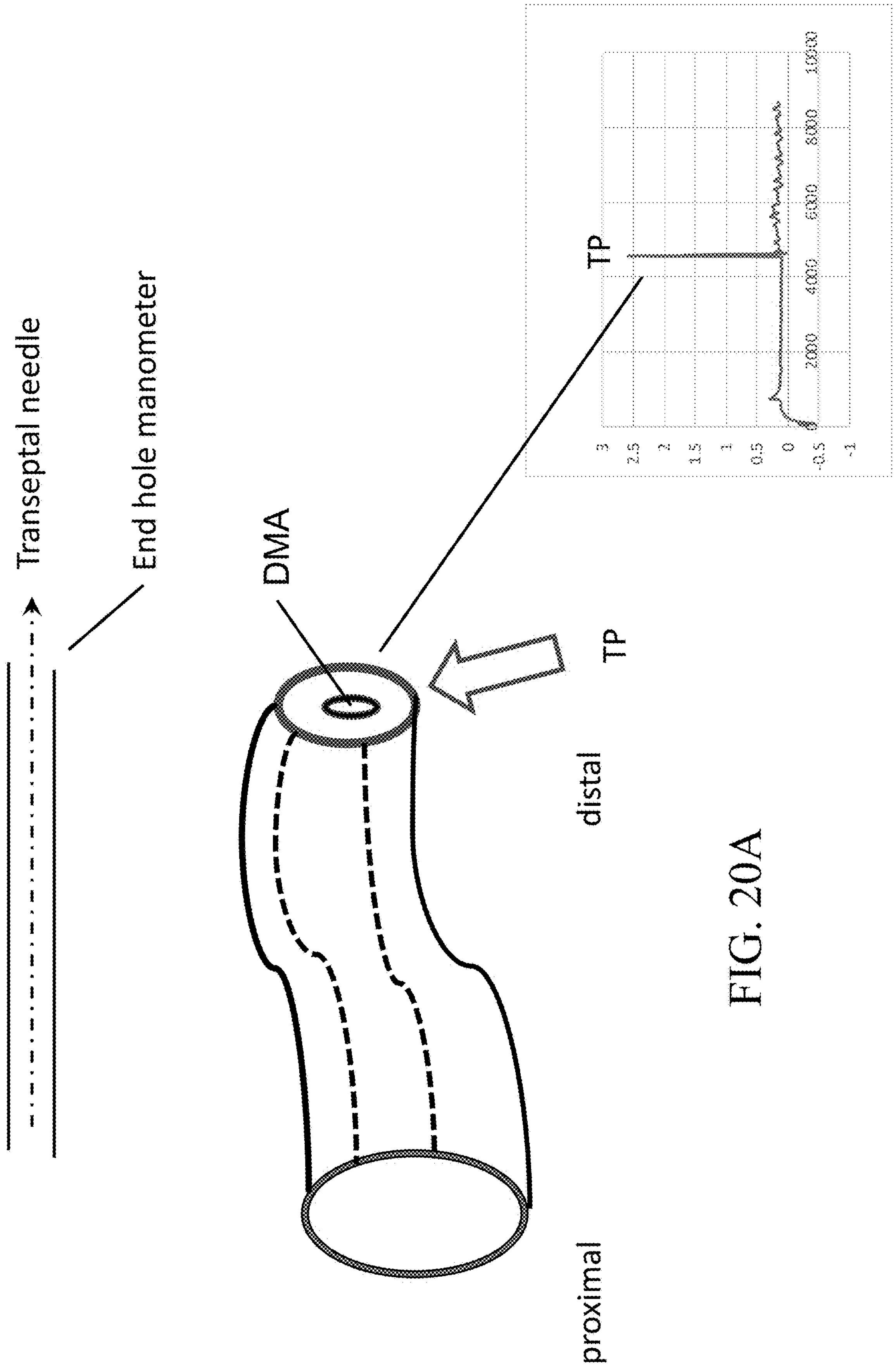
FIG. 20A shows a schematic representation of an embodiment of a haptic finger sleeve (HFS) fitted and is worn by an operator with different haptic actuators with a distal most actuator (DMA) that is the distal most aspect and provides continuous position and time dependent haptic feedback to the operator.
Figure 20B:
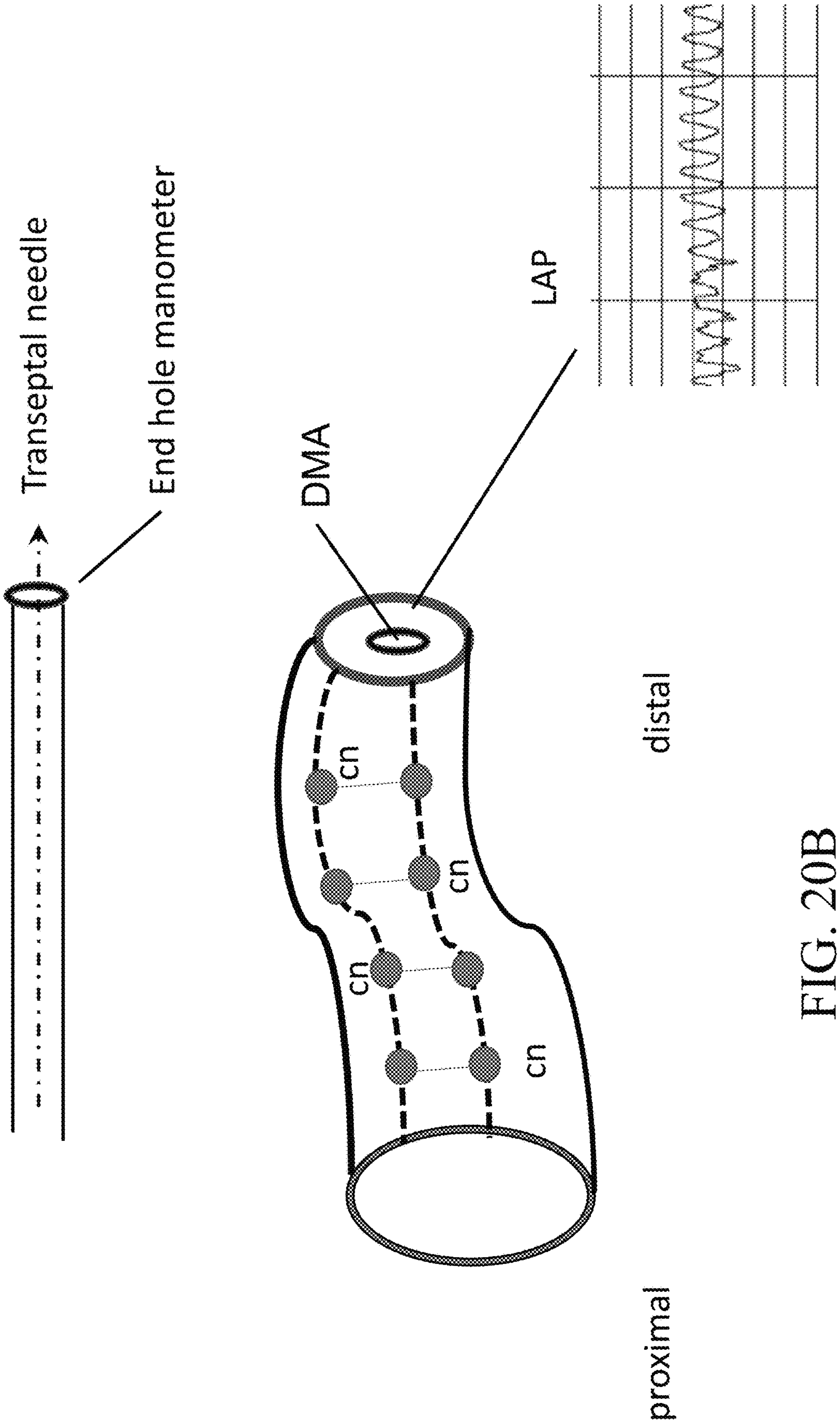
FIG. 20B shows the schematic representation of FIG. 20A as the inserted guiding catheter is advanced into the left atrium the intra-atrial pressure waveform sensed from within the left atrial cavity (LAP) is transduced and rendered palpable at DMA notifying the operator that the catheter tip has just entered the left atrium and is free floating as the pressure signal from the transeptal needle is not dampened.

By way of example, referring to FIG. 20A, the DeHA is a haptic finger sleeve (HFS) fitted with different haptic actuators and is worn by the operator and provides continuous position and time dependent haptic feedback to an operator. The HFS can be worn on any digit or be worn on an arm or other body part. DMA positioned at the distal most aspect is actuated to provide a single impulse at time of transeptal puncture (TP) to the fingertip (e.g., using a haptic speaker). Referring to FIG. 20B, as the inserted guiding catheter is advanced into the left atrium the intra-atrial pressure waveform sensed from within the left atrial cavity (LAP) is transduced and rendered palpable at DMA notifying the operator that the catheter tip has just entered the left atrium and is free floating as the pressure signal from the transeptal needle is not dampened (i.e., from being opposed to the interatrial septum or atrial wall). The transeptal needle can then be removed, and LAP signal sensed by the guiding catheter's end hole manometer.

Figure 20C:
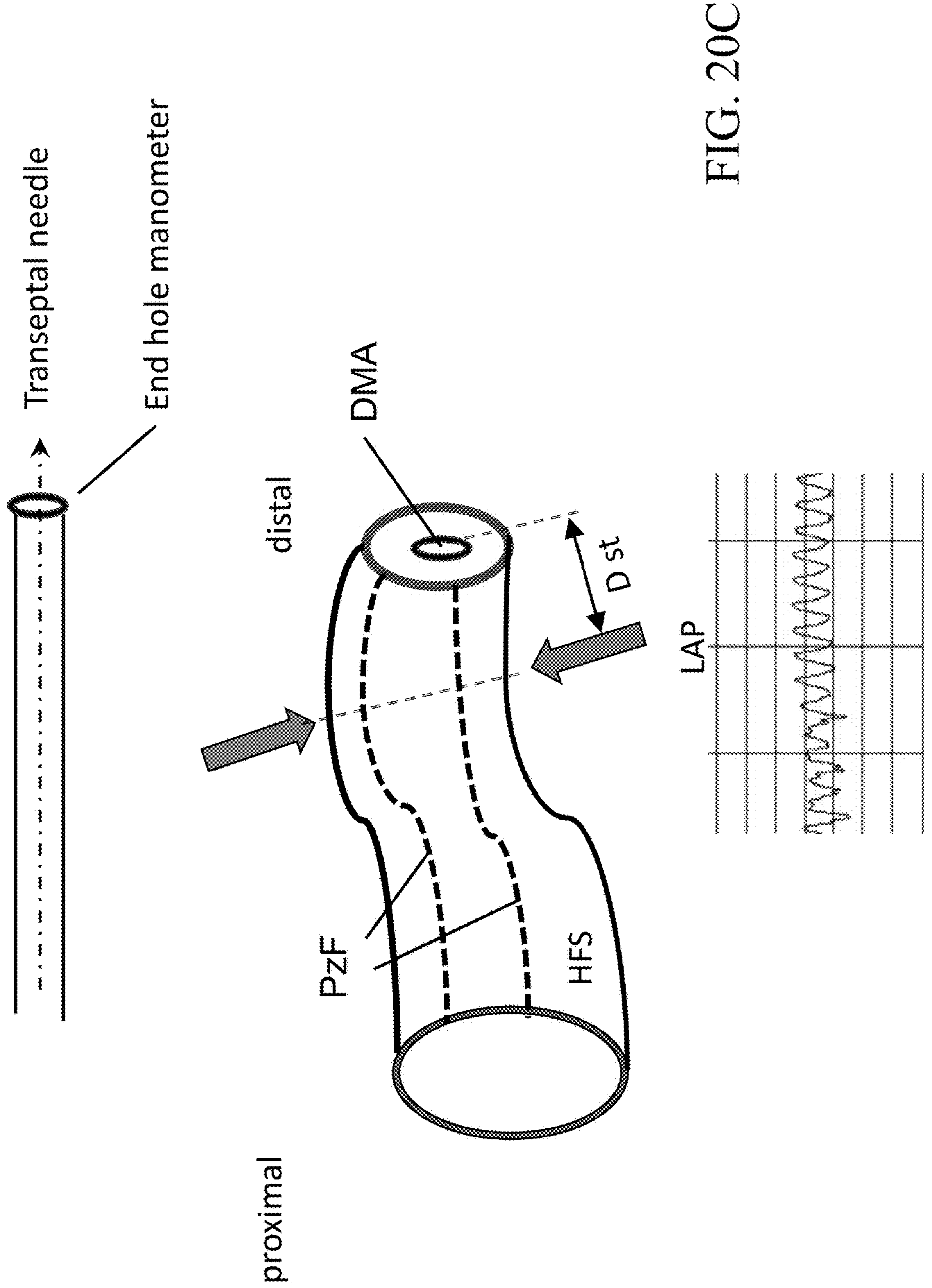
FIG. 20C shows the schematic representation of FIG. 20A as the guiding catheter is advanced, the LAP haptic signal is transduced focally by piezo electric filaments (PzF) rather than DMA, and the haptic effect palpated further proximally back along the HFS as the catheter is advanced providing the operator with time dependent haptic spatial feedback so they are aware of the change in relative distance between the catheter tip and interatrial septum.

As depicted in FIG. 20C, as the guiding catheter is advanced, the LAP haptic signal is now transduced focally by PzF (rather than DMA) and the haptic effect palpated further proximally back along the HFS as the catheter is advanced providing the operator with time dependent haptic spatial feedback so they are aware of the change in relative distance between the catheter tip and interatrial septum. This haptic effect in one embodiment is a gentle contraction of segments of the wearable haptic finger sleeve generated by stimulating piezo actuator filaments/yams as described above at the location of conductive nodes (cn) as depicted in FIG. 20B. The effect is that the piezoelectric yams (or other haptic actuator) focally contract about the operator's finger, hand, wrist and the like at progressively more proximal locations, the distance of which is proportionate to the distance between a given anatomic regions (e.g., interatrial septum in this example) and another site (e.g., catheter tip). Note that the LAP signal (rather than TP) is being used to indicate location of the interatrial septum in this embodiment, but alternate embodiments are within the scope and spirit of the present disclosure where alternate haptic transducers/haptic sensations can be generated to denote change in distance between anatomic structures in real time. This signal is thus a surrogate for TP and, in an embodiment, generated from either real-time haptic pulsations coincident with a 1:1 ratio or alternate ratio (e.g., 3:1) relative to the cardiac cycle.

In embodiments, the haptic effect can be from previously stored signals (e.g., loop of LAP signal that was acquired earlier in the procedure prior to the catheter being further advanced within the left atrium) or a real time signal such as intracardiac electrogram (EGM) or intracardiac pulse pressure denotation of the R wave/cardiac systole or even be representative of inotropic cardiac state. If a higher frequency (not 1:1) ratio haptic effect is desired by the operator, then the amplitude of the haptic effect relative to the sensed signal ideally remains proportionate and temporally related to the real time sensed signal (e.g., R wave amplitude, pulse pressure) as is illustrated in FIG. 19B where A and D occur coincident with sensed signals (EGM) and are gained according to sensed physiologic signal and B and C which are interpolated, fixed, and have a lower amplitude. This helps prevent attenuation/habituation of tactile sensing and optimizes operator haptic response times while preserving physiologically relevant information in a haptic format. The location of the tip of the catheter (or other segment) relative to the interatrial septum (or other anatomic location), Dst, can be calculated by any number of imaging modalities including intracardiac echo, fluoroscopic data, electromagnetic, magnetic, impedance based navigational systems and the like and a Dst calculator that accounts for the anatomic features of a given patient's heart and characteristics of the inserted guiding catheter. Any type of navigational system can be implemented and is within the scope and spirit of the present disclosure. Once the guiding catheter is free floating within the left atrium an ablation catheter with contact/contact force sensing capability (CFs in FIG. 20D) can be exchanged in place of the transeptal needle and use for delivery of ablation energy or other device for structural heart interventions.

Figure 20D:
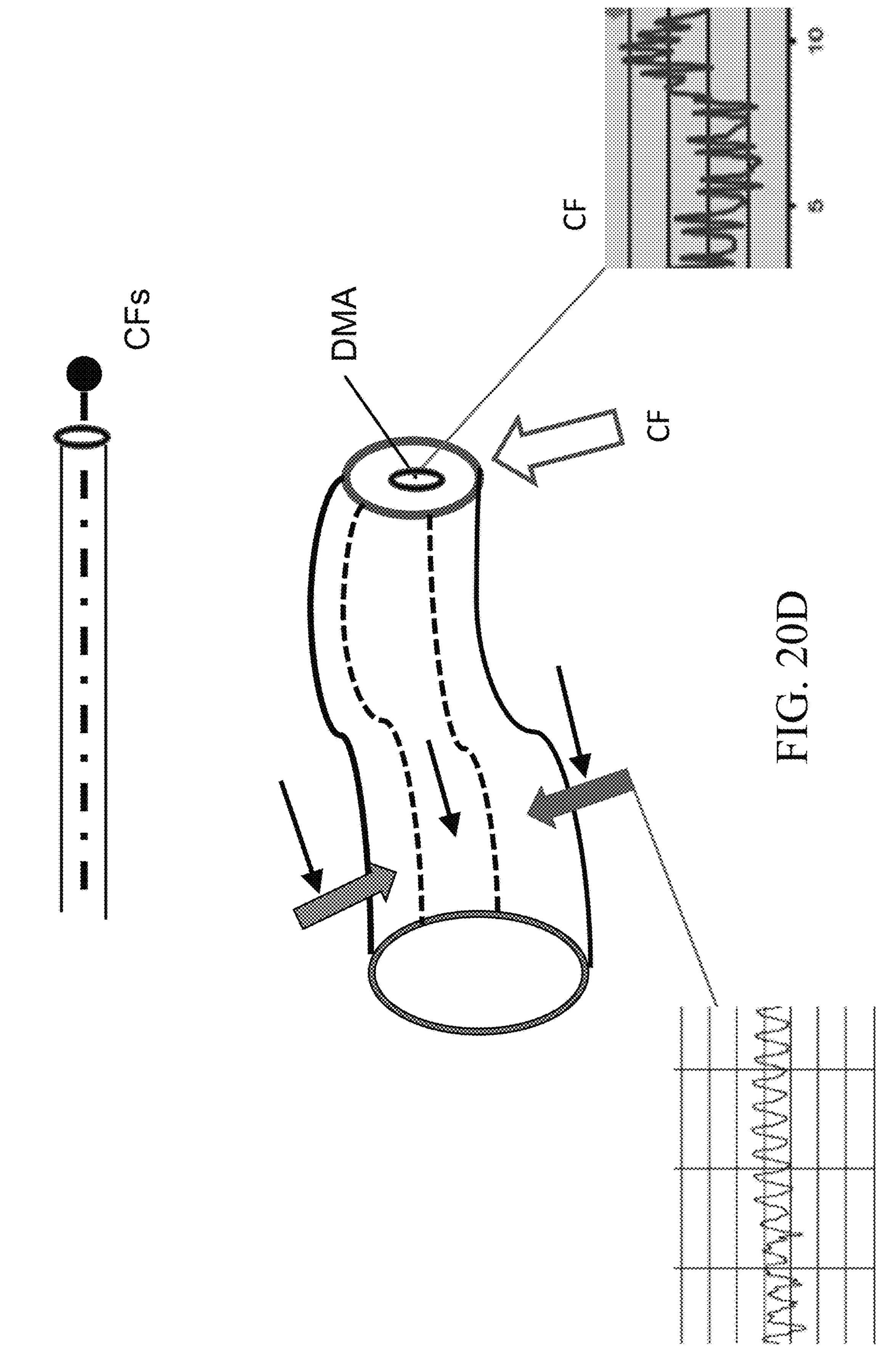
FIG. 20D shows the schematic representation of FIG. 20A as a distal aspect of the ablation catheter's contact sensing sensor is opposed to cardiac tissue in preparation for delivering radiofrequency energy (e.g., about the pulmonary vein os) and the sensed CF signal is rendered palpable at DMA while the LAP surrogate signal generated by PzF is now more proximal and can continue to serve as a haptic identifier of the location of the interatrial septum or other cardiac structure.

Continuing with referring to FIG. 20D, the distal aspect of the ablation catheter's contact sensing sensor is opposed to cardiac tissue in preparation for delivering radiofrequency energy (e.g., about the pulmonary vein os) and the sensed CF signal is rendered palpable at DMA while the LAP surrogate signal generated by PzF is now more proximal and can continue to serve as a haptic identifier of the location of the interatrial septum or other cardiac structure. The operator can choose whether to keep the LAP signal active or not (or in one embodiment it fades out in amplitude over time until tissue contact is achieved) and once ablation energy is being delivered LAP haptic signal ends and the operator just appreciates the CF signal (CFs) generated in this embodiment at DMA.

Figure 20E:
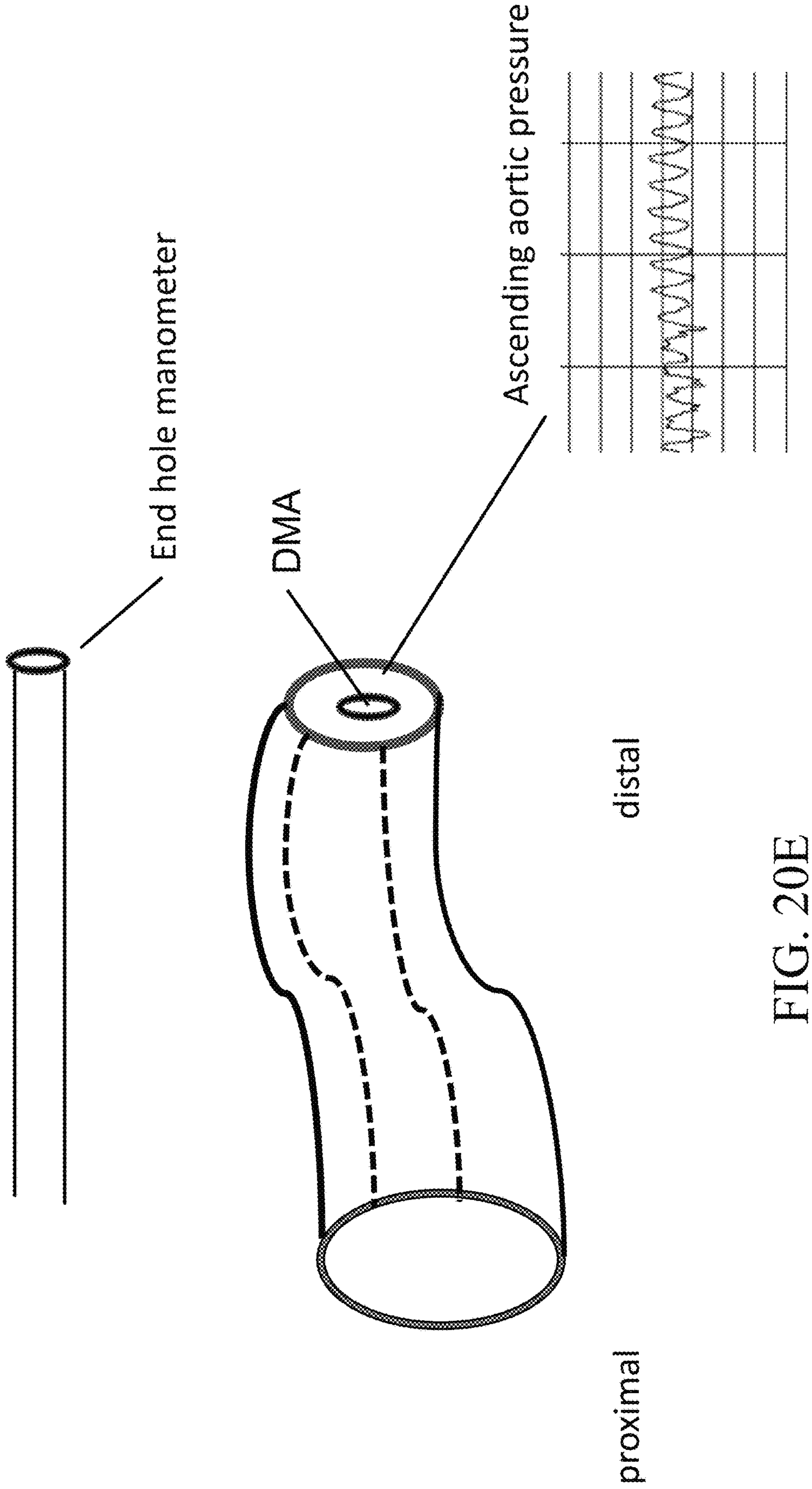
FIG. 20E shows the schematic representation of FIG. 20A with the fiducial signals include palpation of intra-aortic pressure, palpation of high velocity blood flow emanating from a stenotic aortic valve.
Figure 20F:
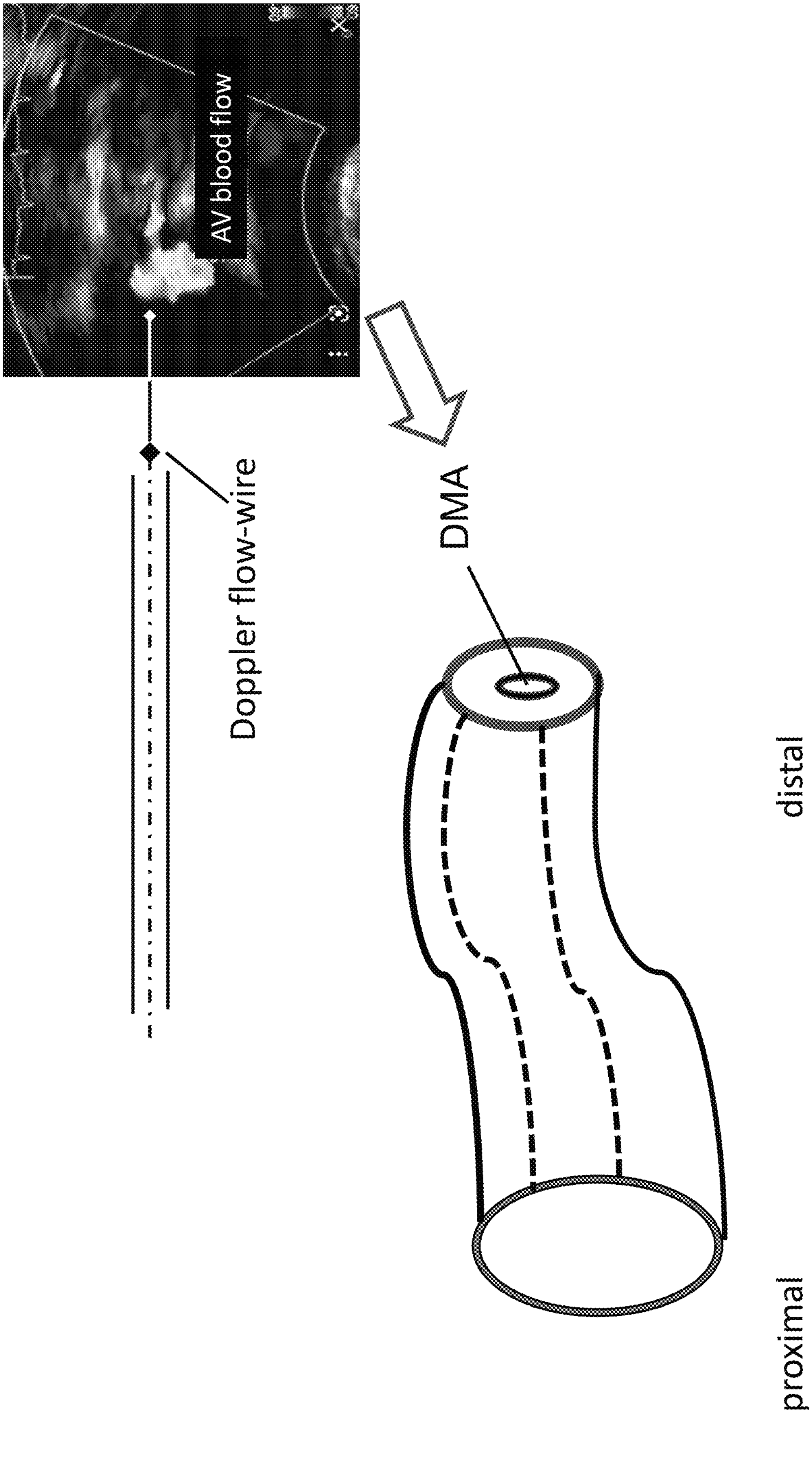
FIG. 20F shows the schematic representation of FIG. 20A with blood flow velocity measured by a ultrasonic Doppler flow-wire as in as to assist crossing a guidewire across the valve plane through a potentially critical stenosis, and sensing the left ventricular pressure waveform once the catheter is positioned into the left ventricular outflow tract.

The spirit and scope of this haptic algorithm is not limited to accessing the left atrium via transeptal puncture to perform ablation which is exemplary and can be implemented during other interventions including but not limited to transfemoral aortic valve replacement (TAVR) or transcatheter mitral valve repair/replacement. By way of example, during TAVR, the fiducial signals include palpation of intra-aortic pressure as shown in FIG. 20E, palpation of high velocity blood flow emanating from a stenotic aortic valve (e.g., measured by a ultrasonic Doppler flow-wire as shown in FIG. 20F) as to assist crossing a guidewire across the valve plane through a potentially critical stenosis, and sensing the left ventricular pressure waveform once the catheter is positioned into the left ventricular outflow tract. Likewise, the sensed signals can include other physiologic or biophysical information such as inotropic state of the heart, sensation of a needle/catheter crossing tissue planes including but not limited to structures encountered during epicardial puncture or transapical placement of a bioprosthetic heart valve. The valve plane can also include the mitral, tricuspid or pulmonic valves, or any structure affected by congenital heart disease including but not limited to atrial or ventricular septal defect, patent foramen ovale, patent ductus arteriosus, coarctation of the aorta, supravalvular or sub valvular stenosis. Additional haptic sensations can be rendered palpable as well including palpation of tissue necrosis (e.g., at DMA) during delivery of ablation energy (radiofrequency, cryoablation, pulse field ablation, etc.), and even palpation of the induction of ventricular fibrillation, VF, (which is used to cause cardiac standstill) during deployment of the bioprosthetic aortic valve during TAVR. In the latter application the ECG or intracardiac electrogram signal can be input into the haptic system to be transduced into a palpable physiologic VF event with a haptic sensation with the same or similar frequency (e.g., 300 BPM=5 Hz) and variable amplitude/frequency dependent on the sensed EGM signal.

Figure 21:
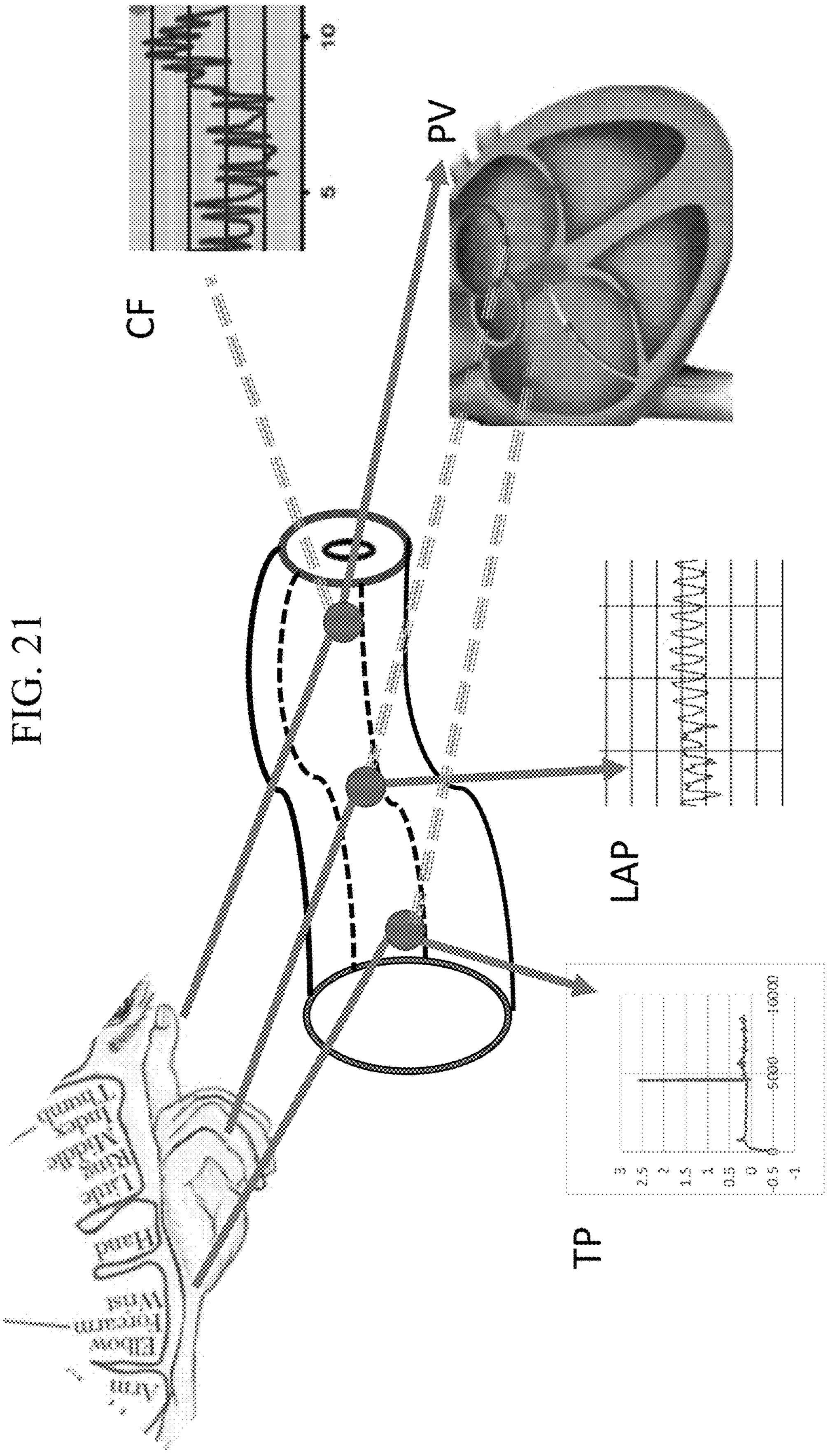
FIG. 21 shows a schematic representation of an embodiment of a haptic sleeve system fitted and is worn by an operator with different haptic actuators that provide sensed physiologic/biophysical signals (transeptal puncture (TP), left atrial pressure (LAP), catheter tissue contact force (CF)) from a given patient acquired at different, contiguous anatomic intra-cardiac locations (e.g., interatrial septum, left atrium, pulmonary vein (PV)) are used to generate haptic signals to different anatomic contiguous sites (e.g., fingertip of thumb, ring finger, wrist) and provide time dependent physiologic information in a haptic format that is processed by contiguous regions of the somatosensory parietal cortex creating a real time haptic homunculus.

Referring to FIG. 21, sensed physiologic/biophysical signals (transeptal puncture (TP), left atrial pressure (LAP), catheter tissue contact force (CF)) from a given patient acquired at different, contiguous anatomic intra-cardiac locations (e.g., interatrial septum, left atrium, pulmonary vein (PV)) are used to generate haptic signals to different anatomic contiguous sites (e.g., fingertip of thumb, ring finger, wrist) and provide time dependent physiologic information in a haptic format that is processed by contiguous regions of the somatosensory parietal cortex creating a real time haptic homunculus.

In yet another embodiment, the haptic system performs haptic Doppler display with or without aliasing. Those experienced in the art of Doppler echocardiography understand that the color-coded visual display from ultrasonic blood flow (or tissue Doppler) identifies blood flow velocity and direction. Blood flow that is moving away from the transducer is colored blue and towards the transducer is red. Brighter colors indicate higher velocity blood flow and can identify stenotic valves or severely regurgitant valvular pathology. Aliasing occurs when blood flow velocity is greater than a pre-specified cut off value. Referring to FIG. 20F, yellow color indicates any blood flow velocity over 4.5 meters/second and is seen with severe stenosis. Likewise, the haptic signal provides a metric of blood flow direction and tissue or blood flow velocity. As the velocity increases the haptic frequency and/or increases. Above a pre-specified cut off value haptic aliasing occurs where the frequency and or amplitude of the signal jumps significantly in value (e.g., 5 times the current frequency and/or amplitude). Blood flow direction can be indicated by the direction of haptic response or in an alternate embodiment by using a greater (e.g., moving towards an inserted catheter/sensor>3 times the cardiac cycle) or lower frequency (e.g., moving away from an inserted catheter/sensor<3 times the cardiac cycle) about a baseline frequency (3 times the cardiac cycle).

In various embodiments, the haptic system and DMA are capable of transducing signals from multiple sensors manufactured by a variety of vendors including impedance-based data (e.g., Boston Scientific, Medtronic), mechanical force sensors (e.g., Biosense Webster), fiberoptic force sensors (e.g., Abbott), temperature indices (e.g., Medtronic), and indices of tissue necrosis based on one or more signals including but not limited to reflected light, acoustic signals/ultrasound, intracardiac electrogram signal analysis, impedance, temperature information. The location of the haptic actuators and type of haptic feedback is preferably in anatomic regions that have myelinated mechanoreceptive afferents such as rapidly adapting type I (Meissner), or rapidly adapting type 2 (Pacinian) receptors rather than slowly adapting type I (Merkel), slowly adapting type 2 (Ruffini) or unmyelinated (e.g., C-tactile) afferents which have slower response times and catered to the type of receptors being innervated and the wearable haptic interface is constructed to meet these requirements. In embodiments, this can optimize operator haptic to motor response times. Stimulated anatomic regions can also include sensory receptors in muscle (e.g., muscle spindles, Golgi tendon organs) that are sensitive to velocity and stretch (e.g., for communication of force information) and joint spaces (e.g., proprioceptive sensors).

In embodiments, differing sensory cutaneous branches of the median nerve that innervate one or more portions of a user's anatomy such as the hand, wrist, arm (e.g., palmar digital cutaneous branches, palmar cutaneous branches that arise in the forearm and extend to the hand innervating lateral, medial aspects of the palm and digits) are stimulated by different haptic elements optimizing the operator's ability to differentiate varying physiologic and biophysical signals based on anatomic location of haptic feedback in addition to the type of haptic feedback. The anatomic location that is provided with haptic feedback can be programmed to vary from time to time (e.g., temperature sensation moves from first and second digits to third and fourth digits) reducing the likelihood of fatigue of haptic attentional resources but are specifically configured in the shape and structure of the human heart as depicted in FIGS. 22A.

Figure 22A:
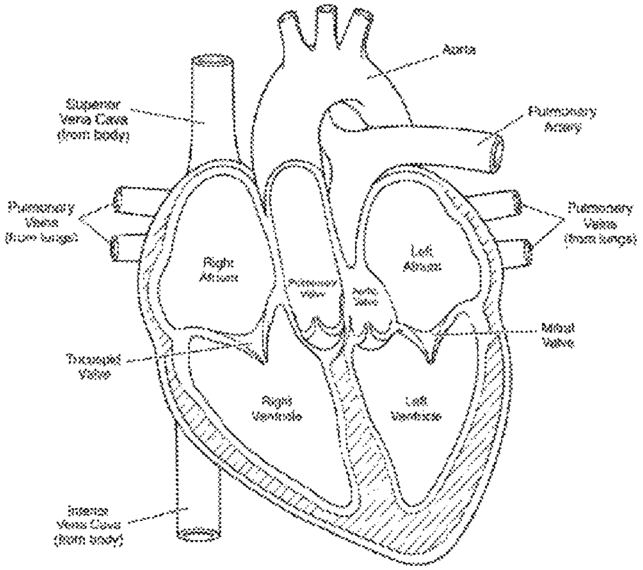
FIG. 22A shows an anatomical representation of the heart used to transduce signals from electrophysiologic procedures.
Figure 22B:
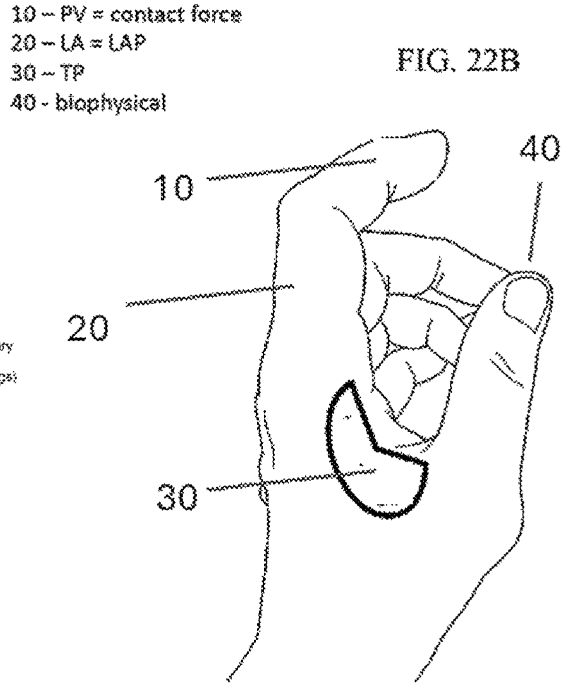
FIG. 22B show a schematic representation of an embodiment of a haptic sleeve system with a haptic hand (left oriented) relative to the anatomical representation of FIG. 22A.
Figure 24A:
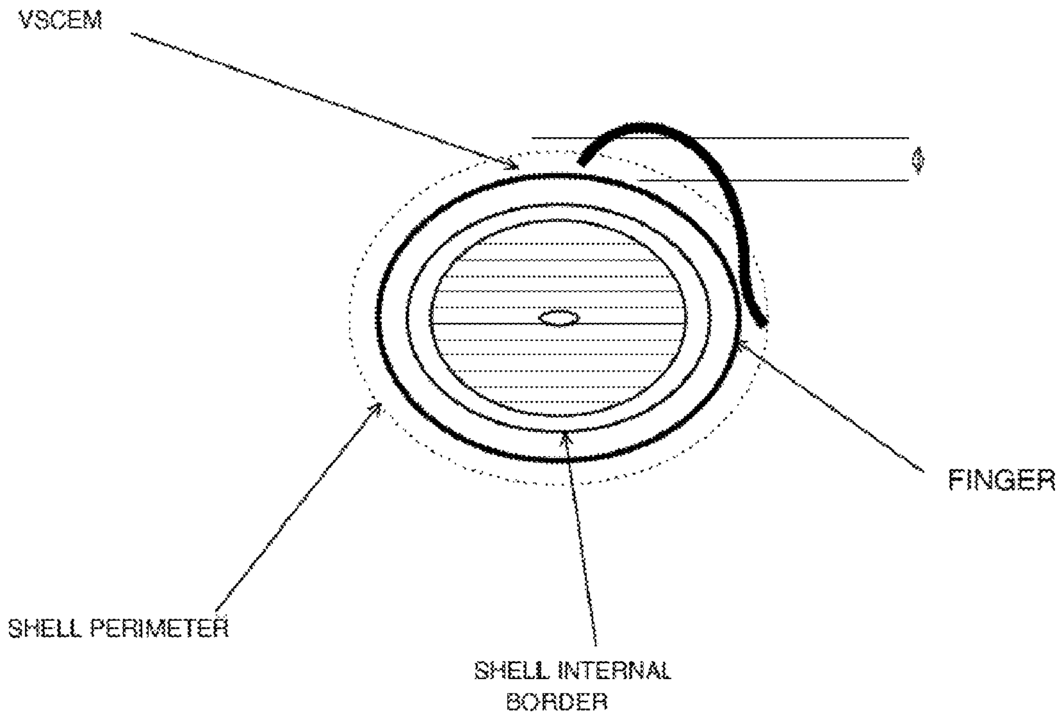
FIG. 24A-24C show schematic representations of an embodiment of a haptic ring system with varying positions of a deformable shell/surface.
Figure 24B:
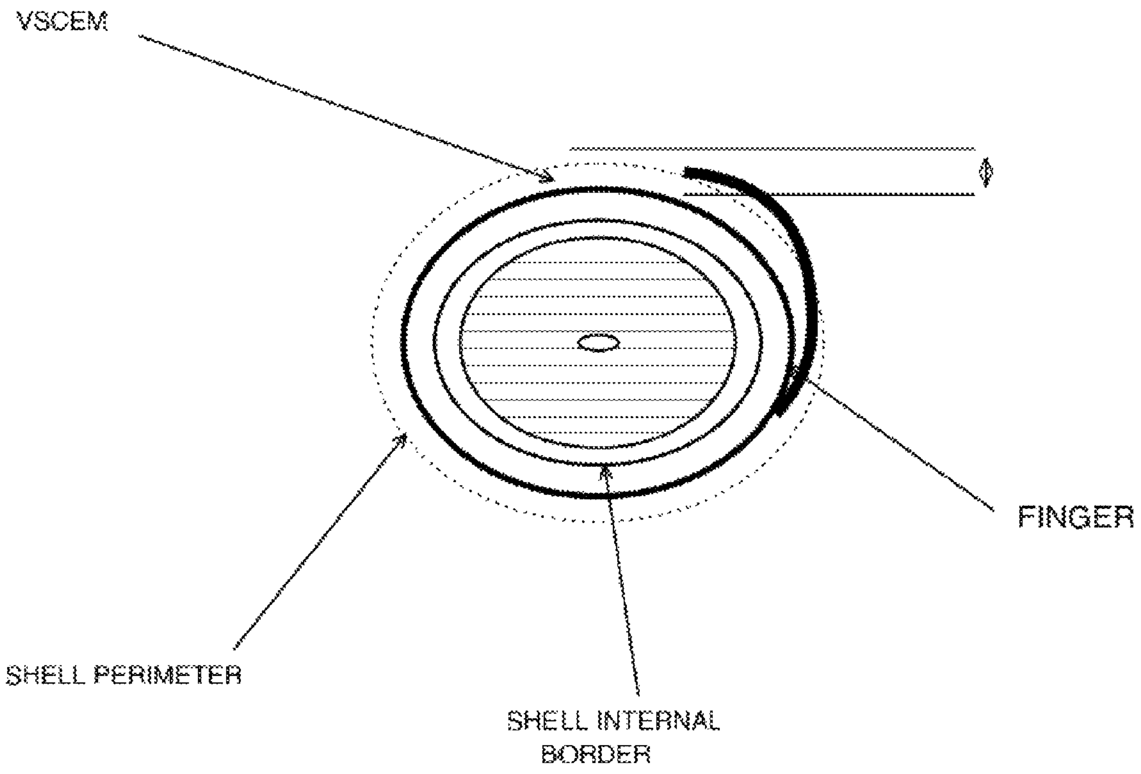
Figure 24C:
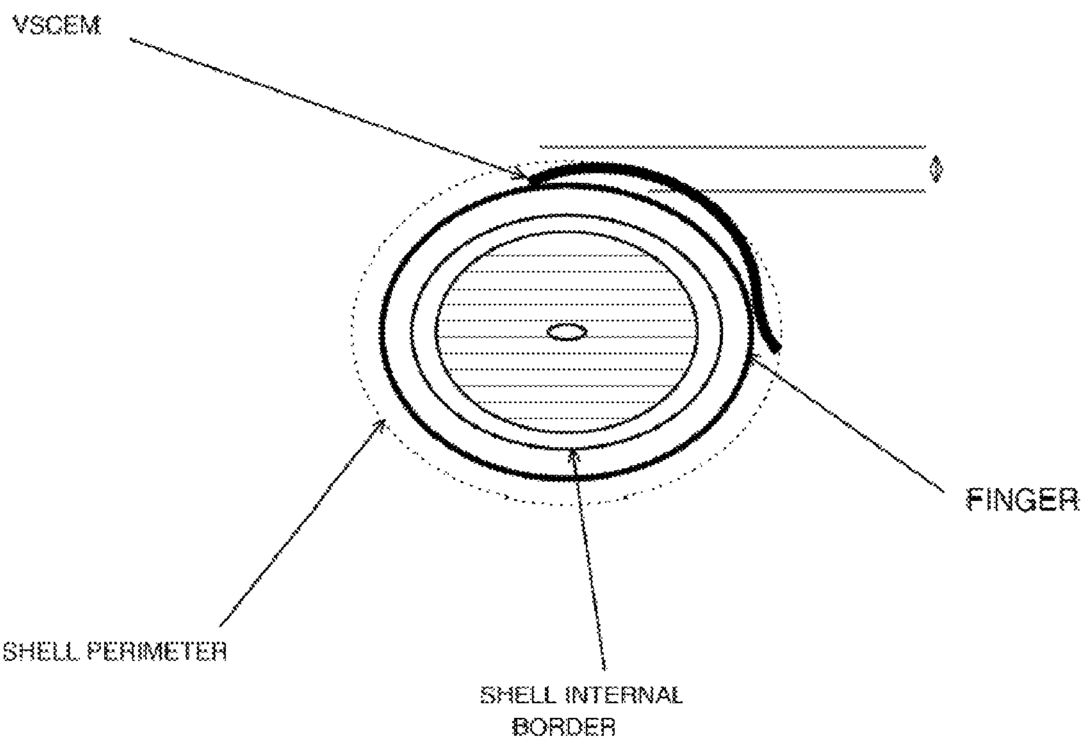
Figure 24D:
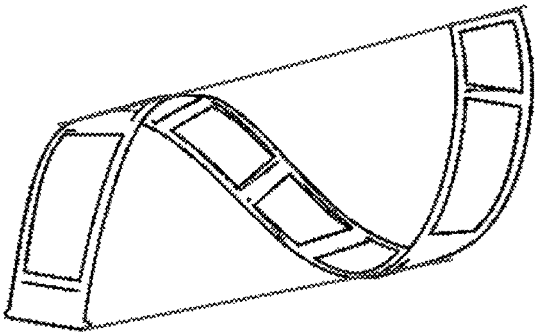
FIG. 24D-24E show pictorial representations of embodiments of the haptic ring system of FIG. 24A.
Figure 24E:

FIG. 22B shows a hand (left oriented) and an anatomical representation of the heart in FIG. 22A. This embodiment is exemplary and in no way is this limited in scope or spirit to any combination of anatomic locations (cardiovascular site in a given patient, anatomic location for haptic feedback applied to the body part of a given operator), type of tactile/force sensation, types of haptic feedback, types of physiologic/biophysical signal generated, type or location of haptic actuator, methods for signal processing, AD conversion, etc. Referencing FIG. 22B, Section 10 at the distal aspect/phalange of the pointer finger is representative of a haptic actuator that provides real time force feedback proportionate to the amount of contact force between a catheter and cardiac tissue (PV os in this example). Section 20 provides force feedback proportionate in amplitude and synchronous in time with LAP, left atrial pressure and is ideally proportionately more proximal on the hand (e.g., metacarpus, proximal phalange) relative to the location of a given sensed signal. The haptic effect of Section 30 is not in a fixed location, it covers more skin surface, and is representative of the proximal anatomic site of transeptal puncture relative to the location of the distal most aspect of an inserted catheter/instrument. In this example, this haptic actuator applies focalized deformation to the anterior and/or posterior aspect of the thenar eminence in one or more contiguous locations (represented by dashes). Section 40 is located over the distal aspect of the thumb and is reserved, in this example, for transducing biophysical signals including but not limited to an index of tissue necrosis, amplitude of an electrogram signal, indices of impedance, resistance, admittance, temperature, denotation of time of resolution of an arrhythmic focus (e.g., pulmonary vein isolation), sensations of steam pop when too much ablation energy is applied and the like.

At Section 10 a user appreciates force feedback by way of example from a small haptic speaker, thin piezo actuator or other haptic element at the DMA (a distal most actuator) that generates a gentle force or tactile sensation proportionate in amplitude to contact force or an index or contact force (e.g., in part or whole using tissue impedance-based data). At Section 20 left atrial pressure is transduced using a piezo actuator (or other haptic element) that applies a dynamic force proportionate to measured pressure. This pressure signal is present when end or side hole manometry or other pressure sensor provides a signal to the haptic computing system. At Section 30 the intra-cardiac location of the interatrial septum is landmarked by a constant tactile deformation signal (e.g., soft pinch, compression) generated, for example, by an elastic fibrous web (EFW) intertwined with piezo actuator filaments with yams of about 500 to 2000 denier uniformly spaced at about 10-30 yams per 0.5 cm width and having a Young's elastic modulus such that there is less than moderate compression and comparable to human tissue such as tendon, skin, ligament (e.g., between 1.0 and 2.0 GPa) with comparable viscoelastic mechanical behavior and force-strain curves as shown in FIG. 18A. Thus, in this example, Sections 10 and 20 apply force feedback, and 30 applies tactile and force feedback representative of varying anatomic locations, types of sensed signals. Another example of a sensed signal that can be provided at Section 30 is sensed left atrial appendage tissue motion (reference is made to FIG. 2C). In this example, ultrasonic tissue Doppler, mechanical sensor or other sensor modality may be used to detect uniform opposition of a left atrial appendage occlusive device (e.g., Watchman) within the left atrial appendage and the haptic signal can be generated by a piezo actuator, circular resonator, micro-electromechanical device, and the like.

At Section 40 in FIG. 22B, the DMA provides tactile sensations representative of biophysical signals and in an embodiment employs psychophysical haptic rendering as known by those experienced in the art and covered in the inventor's prior intellectual properties. These rendered haptic effects relay sensations such as temperature (hot or cold), steam pop from cavitation of intracardiac blood subjected to too much energy that poses risk for stroke, indices of tissue necrosis or other representation of tissue health or injury, intracardiac electrogram or other electrical information, thermal energy, esophageal temperature, etc. Users will intuit force feedback rendering of contact force and intracardiac pressure, while some degree of training will be important to fully appreciate the transduction of sensed signals using psychophysical haptic rendering.

In another application, the Haptic Heart Hand is employed during transfemoral valve replacement/repair (e.g., TAVR). Referring to FIG. 23C (right-handed orientation), at Section 50, DMA, the pressure sensed by the most distal aspect of the inserted guide catheter (e.g., pressure sensor including but not limited to simple end hole manometry) is transduced as a force signal on or about the pointer finger's distal phalange (or other anatomic site). At Section 60, more proximal pressure data (e.g., intra-aortic pressure) is transduced as force feedback at the proximal phalange (or other more proximally located anatomic site). At Section 70, (referred to as haptic flow and fit transducer), the haptic signal is tactile and capable of haptic representation of either blood flow velocity or contact uniformity of an inserted bioprosthetic device (or other implanted device, Watchman, CE ring, other valve prosthesis, balloon valvuloplasty device, cryoballoon ablation system. clamshell atrial septal defect/PFO closure device, etc.). Contact uniformity can be derived by readily available signals including ultrasonic data, blood flow velocity or microfabricated sensors (as known by those experienced in the art and depicted in FIG. 23) that are seamlessly positioned about the circumference of the implanted device and can be used at time of implant or for outpatient remote monitoring. This enables haptic confirmation of uniform contact and opposition to treated tissue (e.g., aortic valve plane, left atrial appendage orifice, etc.) and detection of para-prosthetic leaks and device instability. Implementation of the wearable haptic feedback system for blood flow related to valvular pathology is one application though the teachings herein are also applicable to revascularization procedures for peripheral vascular and coronary artery disease.

In this example, the sensed signals are initially blood flow velocity (e.g., detected by a Doppler flow-wire) and used to guide the operator to cross a critically stenotic aortic valve (as described in more detail above). During deployment of the bioprosthetic valve, the same haptic transducer or alternate transducer in the same location (e.g., distal most aspect of the thumb, distal phalange) provides haptic confirmation of uniform opposition of the TAVR in the aortic annulus with a specific focally applied haptic signal whose properties are proportionate to the degree of contact uniformity (e.g., high frequency vibration that increases or decreases in frequency and or amplitude). Calcific aortic stenosis leads to heterogeneous tissue properties due to myxomatous degeneration, calcium deposits, and the like and lack of uniform contact of a TAVR prosthesis can result and lead to paravalvular aortic regurgitation, intra-procedural dislodgement, or even future valve dislodgement. In an embodiment, the haptic signal at Section 70 is applied in a uniform circumferential fashion about a user's anatomic site (e.g., about the wrist, finger, along the thenar or hypothenar eminence). A piezo actuator, viscoelastic membrane (VSCEM) embedded as a shell about a shell-like ring support, smart material, or other haptic device(s) can be used to deliver the haptic signal, for example, about a user's finger or other aspect of their extremity (e.g., wrist, forearm as depicted in FIGS. 24A-24E.

In this embodiment, the circumference of the TAVR bio prosthesis contains 4-8 haptically enabled contact sensors (and/or vibration sensors as discussed below) that are preferably evenly spaced about the bioprosthetic circumference. The sensors (depicted as 80 in FIG. 23A) include but are not limited to any mechanical or pressure sensor that seamlessly conforms to the circumference of the bioprosthetic valve ring as known by those experienced in the art. One of the salient and clinically relevant haptic feedback scenarios occurs when the TAVR is deployed correctly and the pressure gradient across the aortic valve plane drops. This will be appreciated by the same amplitude force feedback at Sections 50 and 60 which will have a notable palpable differential amplitude until the transvalvular gradient normalizes.

Figure 25A:
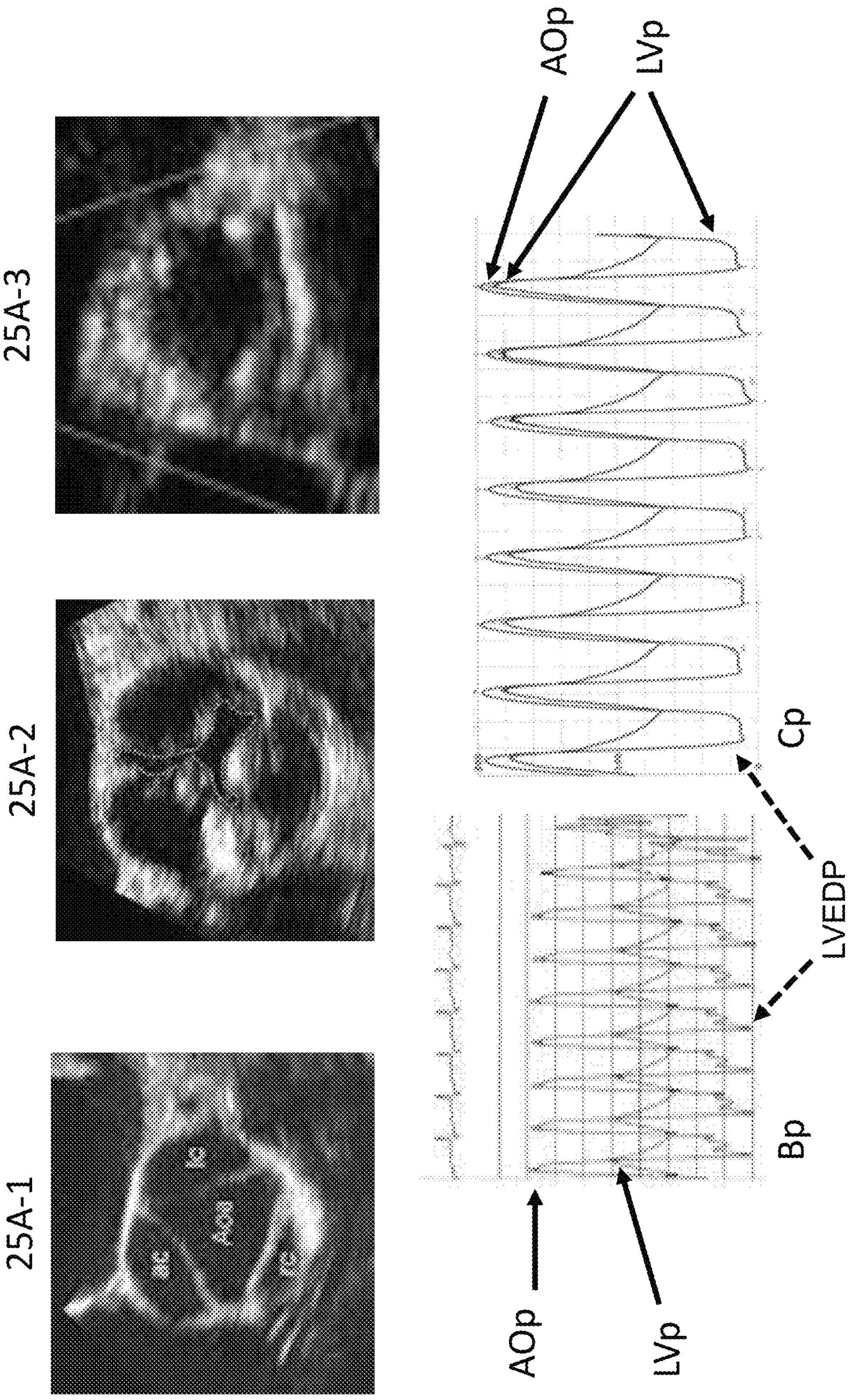
FIG. 25A shows a set of graphical representations of a cross sectional echocardiographic short axis view of a normal aortic valve (25A-1), a stenotic aortic valve (25A-2), and a normal bioprosthetic aortic valve (25A-3) together with graphs of associated pressure waveforms post TAVR deployment.
Figure 25B:
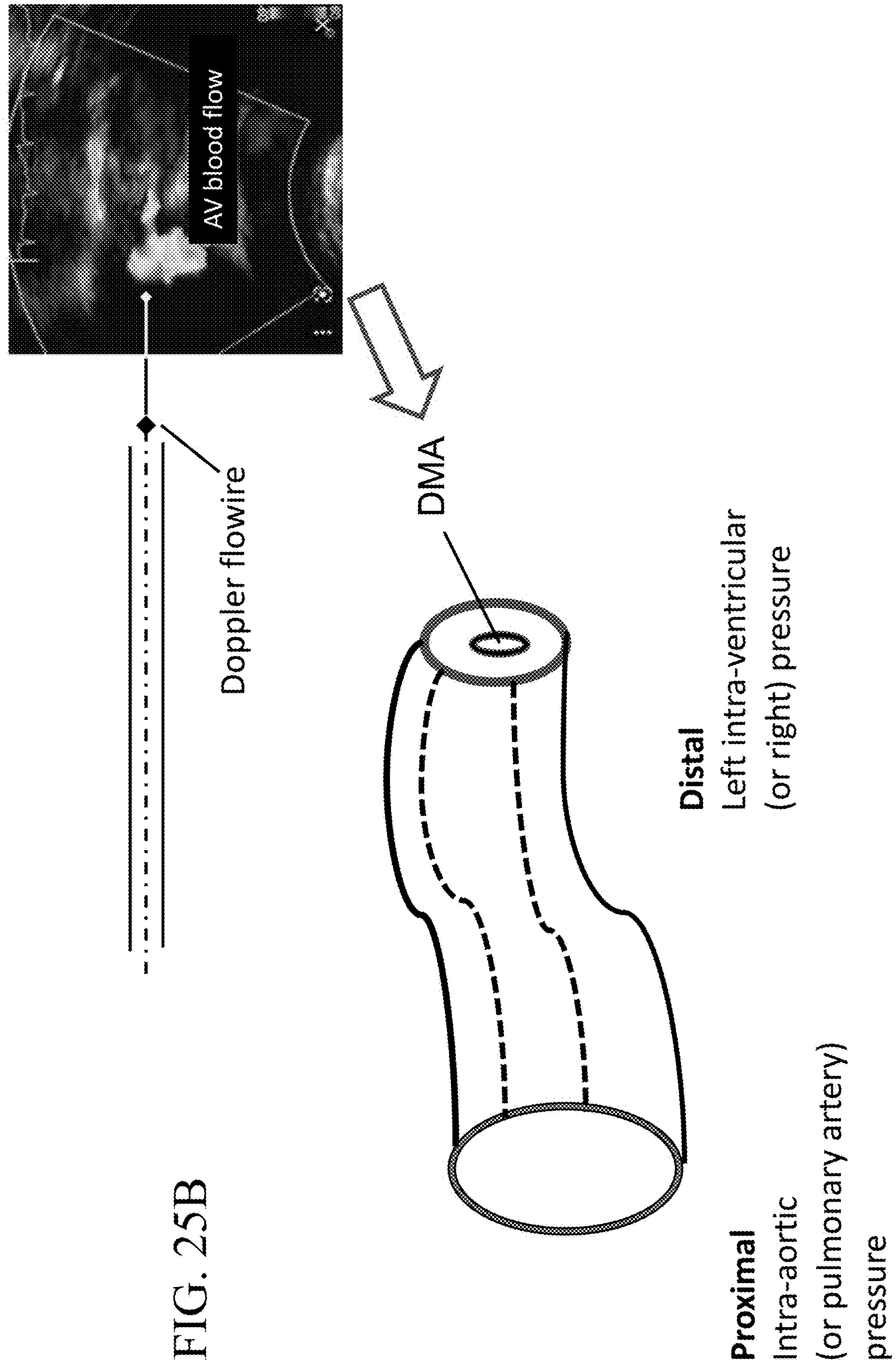
FIG. 25B shows a schematic representation of an embodiment of a haptic sleeve system fitted and worn by an operator with different haptic actuators where Doppler flow-wire senses high velocity blood flow through a stenotic aortic valve transduced at DMA of a haptic sleeve which also provides distal (left ventricular) and proximal (aortic) pressure data to the operator.

Referring to FIG. 25A, a cross sectional echocardiographic short axis view of a normal aortic valve is shown at 25A-1, of a stenotic aortic valve is shown at 25A-2, and a normal bioprosthetic aortic valve status-post TAVR deployment is shown at 25A-3. Waveforms in Bp demonstrates the pressure gradient between the left ventricle (LVp) and aorta (AOp) in the setting of aortic stenosis and waveform Bc normalization of the pressure gradient. The peak-to-peak pressure difference between the aorta and left ventricle are notable in Bp due to aortic stenosis causing a pressure gradient and resolve with the same peak pressure in Cp. Note that the minimum pressure gradient inside the aorta (at end of cardiac diastole) is higher than the minimum pressure gradient in the left ventricle (left ventricular end diastolic pressure=LVEDP). These changes in pressure will be palpable and distinct and will resolve/normalize after successful TAVR implant as seen in Cp. The pressure can be transduced to haptic feedback using force or tactile sensations. By way of example, a piezo actuator can apply both dynamic pulsatile force feedback and deformation (tactile feedback) to a user enabling the operator to palpate aortic and left ventricular pressure waveforms simultaneously providing physiologic hemodynamic information in real time. FIG. 25B shows another embodiment where Doppler flowwire senses high velocity blood flow through a stenotic aortic valve transduced at DMA of a haptic sleeve which also provides distal (left ventricular) and proximal (aortic) pressure data to the operator. Such a sleeve as described in more detail above can be worn on an arm, wrist, finger.

In another embodiment, vibration or other microfabricated sensors (80 in FIG. 23A) positioned circumferentially about a deployed bioprosthetic valve sense a pathologic physiologic signal associated with regional bioprosthetic paravalvular aortic regurgitation and relay this to the operator with a vibratotactile signal at a representative location about their anatomic site (e.g., finger, wrist) that informs them that there is inadequate contact at that location so that they can apply more pressure more effectively deploying the TAVR so there is contact uniformity. Likewise, signs of any injury to the aortic annulus would be rendered palpable (e.g., as a vibration) at time of implant as well as post-implant via remote monitoring of sensed signals using wireless (e.g., Bluetooth) communication systems as known by those experienced in the art or remote monitoring of other implanted systems (pacemakers, defibrillators, pulmonary artery pressure sensors, etc). Thus, the Haptic Heart Hand or other wearable haptic device provides the user with palpable confirmation of successful TAVR or other device implant (e.g., LAAO device) and enables identification of pathologic blood flow properties and tissue damage at time of implant and thereafter.

While the examples provided herein are meant to teach various applications of the technology the wearable haptic feedback system can be utilized for a broad spectrum of pathologic cardiac and vascular diseases including catheter based or minimally invasive valve repair (e.g., transcutaneous edge to edge repair of mitral/tricuspid valves), congenital heart disease therapies, ablation of endocardial or epicardial arrhythmic foci, coronary artery revascularization, cardiac or vascular device implantation. The examples and technologies taught herein are meant to be exemplary and by no means limit the scope and spirit of the present disclosure nor limit the application to cardiovascular interventions.

Geometric Positioning of Haptic Actuators

A plurality of haptic actuators can be positioned within a haptic display enabling a user to sense a dynamic range amplitude haptic effect proportionate to the magnitude of sensed signals (e.g., pressure, force) that would otherwise not be appreciated with a single haptic actuator. The single haptic actuator in these embodiments is small and low cost (e.g., linear vibrator/accelerometer), yet has a limited dynamic amplitude range due to fixed or limited displacement, acceleration, vibration force, etc. Thus, the system can operate within the size and costs constraints required to fit a wearable haptic interface with such actuators and be able to convey amplitude information using an array of inexpensive, simple, small dimension elements. To circumvent the limitations of small sized actuators the haptic display/computing system uses a greater number of actuators and applies palpable sensations over a larger surface area. The number of activated actuators is proportionate to the amplitude of the sensed signal as each individual actuator may not be able to generate a dynamic range of haptic amplitudes.

In one embodiment, several (e.g., 4) linear actuators are positioned a fixed distance apart. The distance is enough so that there is minimal palpable distinction in geometric location but that there is a greater palpable sensation as each actuator is on. The 4th actuator delivers the maximum frequency and maximum vibrotactile effect and the $1^{st}$ has the least while the $2^{nd}$ and $3^{rd}$ intermediate if that is possible, even though the dynamic range may be limited. Introducing a time delay in the order of milliseconds (<40 ms first to last) may render the sensation more pulsatile/realistic though efforts to limit time delays are taken as to avoid any significant latency. The system proportionately can recruit in a stepwise fashion additional actuators when sensed signal amplitude (e.g., contact force, intra-cardiac pressure) increases by, for example, 10 mm Hg between 10-50 mm Hg or 10-50 μm for contact force.

Figure 26A:
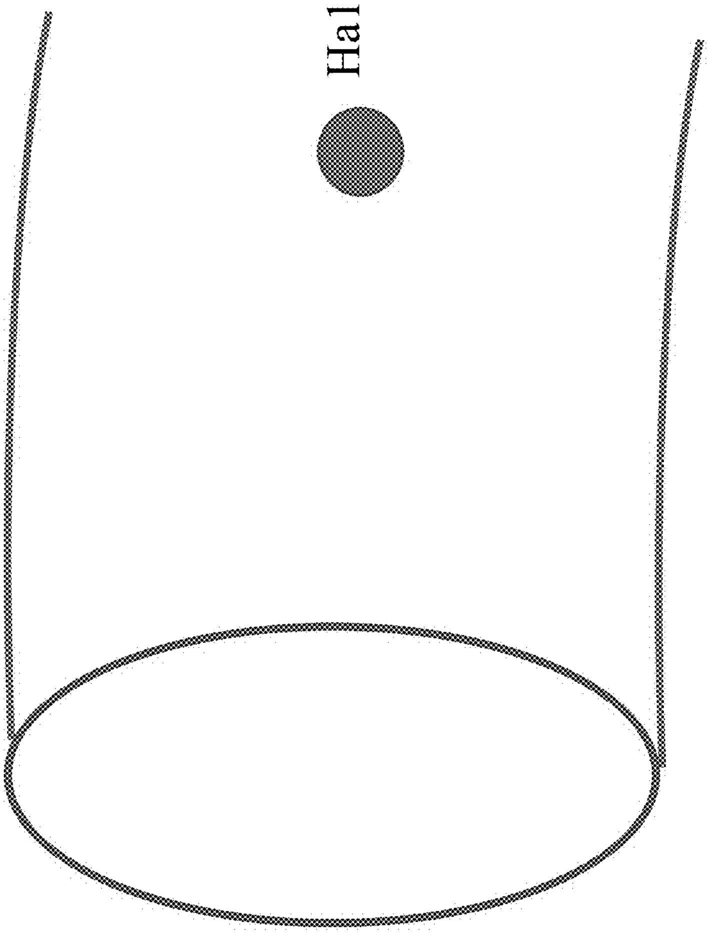
FIGS. 26A-26G depict various exemplary geometric arrangements of small dimension haptic actuators of an embodiment of a haptic sleeve system that provide a surrogate amplitude scale proportionate to sensed physiological/biophysical signals.

By way of example, referring to FIG. 26A, haptic actuator 1 (Hal) is circular with a diameter between 0.2 and 2 cm and thickness between 0.1-0.5 cm and can deliver a palpable sensation (e.g., vibrotactile effect) but has either a fixed or narrow range of haptic amplitudes unable to be differentiated by the user. In embodiments, each of a set of actuators can generate varying frequency (e.g., 0.5 Hz to 500 kHz) haptic effects if not variable amplitude. Any type, size, shape, or thickness actuator as known by those experienced in the art is within the scope and spirit of the present disclosure and those described herein are by way of example. FIGS. 26A-G depict exemplary geometric arrangements of small dimension haptic actuators that in congregate provide a surrogate amplitude scale proportionate to sensed physiological/biophysical signals.

In FIG. 26A a single vibrotactile actuator, Hal, delivers a fixed or relatively fixed amplitude haptic effect. This haptic effect can have variable frequency information but has limited or no amplitude dynamic range.

Figure 26B:
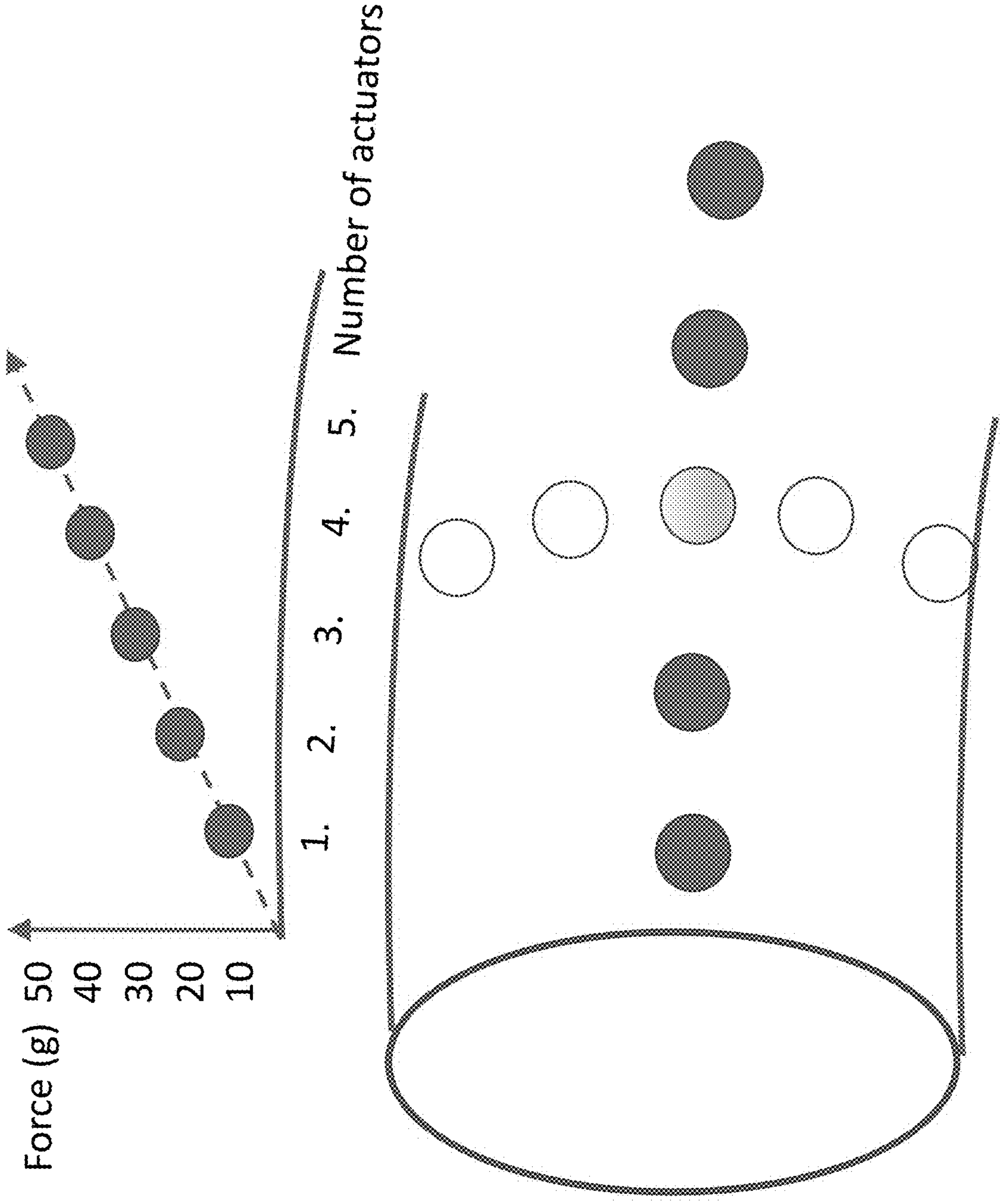

In FIG. 26B, there are multiple actuators depicted in a linear and semi-circular array. In this example 5 actuators are positioned radially along a circumferential direction (circles with no fill) about a user's body part such as a wrist, arm, hand, finger or along one axis (solid fills) that in one embodiment is parallel to the axis of the forearm. The central actuator is depicted with a gradient fill as it can function as part of the circumferential or linear array. In different embodiments both or one of the circumferential or linear arrays can be implemented.

Figure 26C:
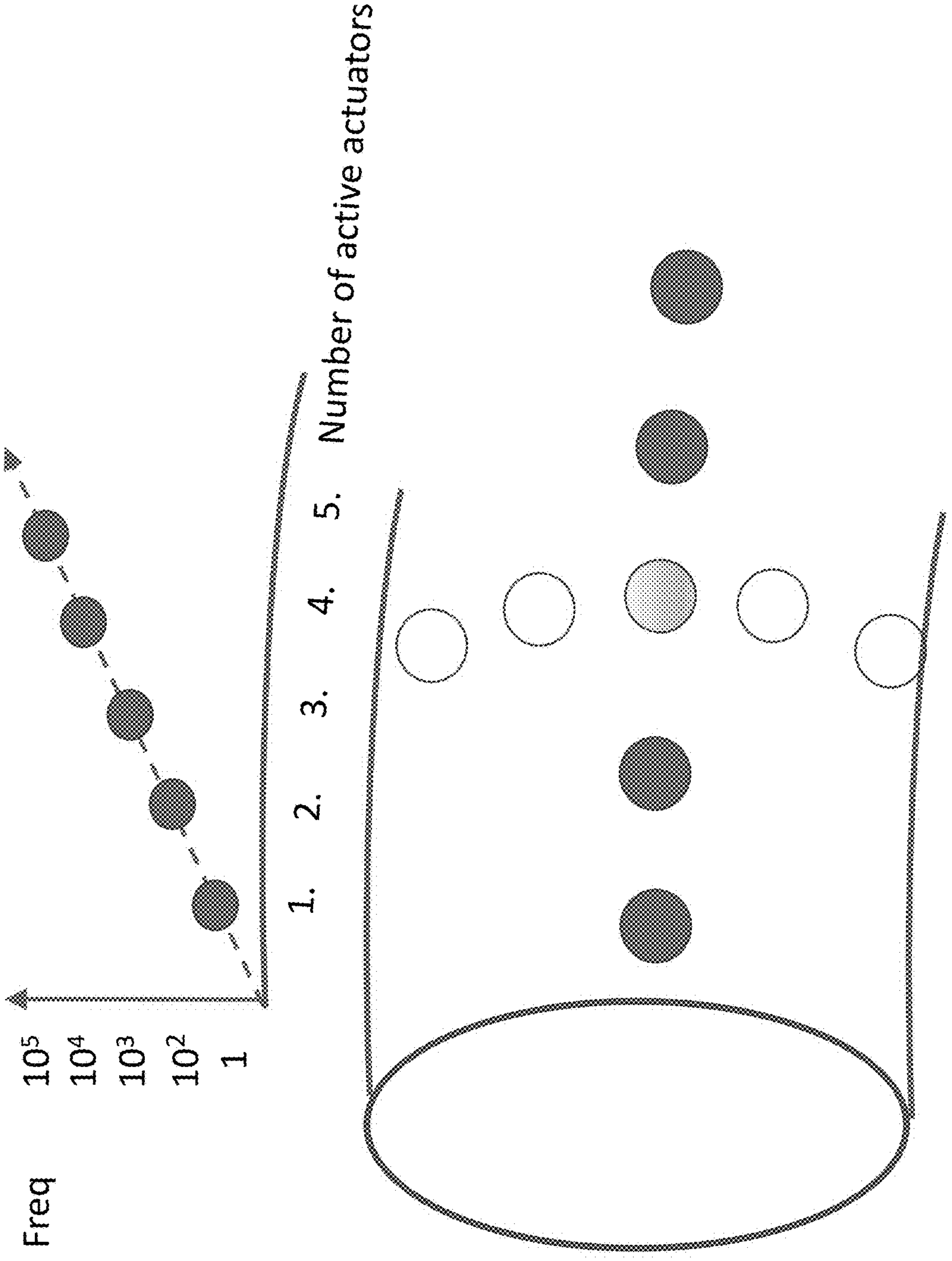

To convey a higher magnitude haptic effect, proportionate to a given sensed signal (e.g., pressure, contact force, temperature, index of tissue necrosis, etc.), the number of actuators are incrementally activated with one actuator representing the lowest amplitude sensed signal and an increasing number of actuators representing higher amplitudes. For example, one active actuator represents too low a catheter: tissue contact force, <or =10 μm, and 5 active actuators indicate a high amplitude (e.g., >50 μm) while 2-4 actuators represent intermediate amplitudes that may be more optimal for tissue ablation. Varying frequency haptic effects can also be implemented to convey changes in the sensed amplitudes such that higher frequencies correlate with higher amplitudes (FIG. 26C). In one embodiment, as an increased number of haptic actuators are active there is a serial increase in frequency of vibrotactile information for all or each sequential one-dimensional actuator as illustrated in FIG. 26C. Thus, actuator 1 may have a vibrotactile frequency of 1 Hz, actuator 2 has a frequency of 10 Hz, actuator 3100 Hz, actuator 4, 1 kHz, and actuator 5 10 kHz. The relative increase in actuator frequency can be linear, curvilinear, logarithmic, stepwise, or otherwise and when considered together with the number of activated actuators accurately informs the user of changes in the amplitude of a given sensed signal.

Figure 26D:
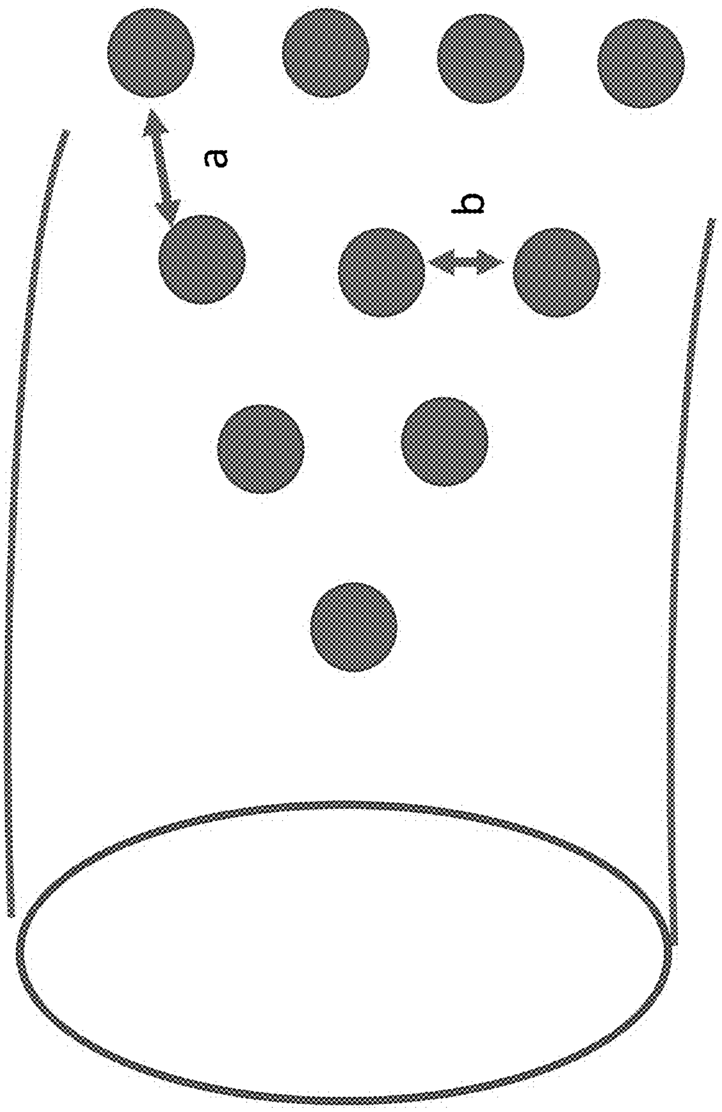

Referring to FIG. 26D, 10 actuators are oriented in a triangular pattern where an increasing haptic effect is represented by a greater number of actuators delivering haptic effects over a larger surface area (e.g., on the forearm). The maximum haptic effect can represent an alert condition such as excessive contact force or tissue necrosis, one haptic actuator representing too low of a force and intermediate numbers represent a graduated amplitude scale. In an embodiment, each actuator may have a dynamic, albeit limited, magnitude range of haptic effect so that an incremental amplitude of any given sensed events causes a more powerful haptic effect (e.g., linear displacement, force), activation of a greater number of actuators, and a higher frequency haptic effect for any number of haptic actuators.

The distance between each actuator, orientation, and actuator features can vary in any of the embodiments and are optimized for haptic feedback. For example, in FIG. 26D distance a and b can be between 0.25 and 0.75 cm. Sequential actuators can be separated by increasing or decreasing distances apart but preferably have the same separation in the provided figures. The separation distance and haptic effects (frequency, amplitude, acceleration, contact surface area, qualitative characteristics, stimulation vector) optimize the user's haptic spatial acuity and ability to distinguish each actuators effect. The anatomic positioning of any given haptic array is likewise optimized to best simulate sensed physiological signals.

In an alternate embodiment, the array of actuators provides anatomically relevant haptic data confirming tissue contact, tissue catheter: contact force, and/or contact uniformity from an array of intracardiac electrodes used to assess therapeutic systems designed for ablation of cardiac arrhythmia (e.g., pulsed field ablation (PFA)) or as to ensure uniform implantation of a cardiac device (e.g., left atrial appendage occlusion device, prosthetic valve implant).

PFA is a non-thermal energy that holds promise to ablate cardiac arrhythmia without incidental damage to surrounding structures (esophagus, phrenic nerve, vasculature). PFA ablation systems can have complex electrical waveforms and variable parameters, but all deliver short duration (seconds) high current, low density energy that causes irreversible electroporation and tissue necrosis disconnecting electrical tissue conductivity and blocking arrhythmic substrates. PFA systems have different constructs and may have electrodes positioned in any number of configurations including a circular fashion, ribbon shape, or spherical array. Some may contain a uniform lattice of electrodes for energy delivery as well as for sensing impedance and temperature data (e.g., Affera Inc.). Bipolar electrograms and impedance data acquired between the electrode(s) and a centrally located indifferent electrode measure indices of catheter tissue proximity/contact and local tissue response to energy delivery (e.g., based on impedance change, temperature response).

Figure 26E:
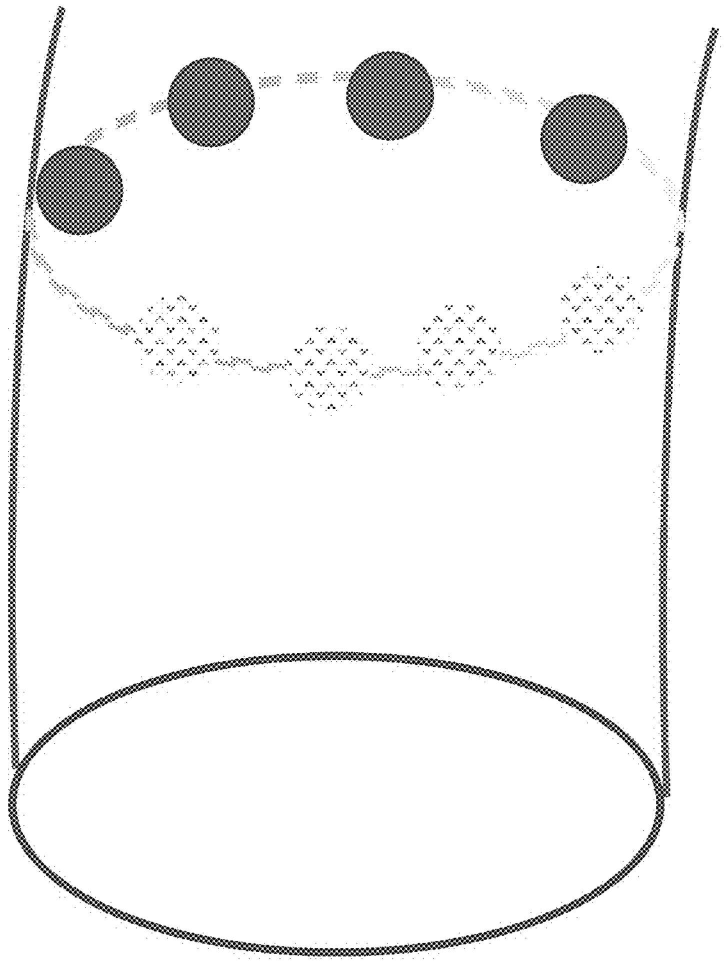
Figure 26F:
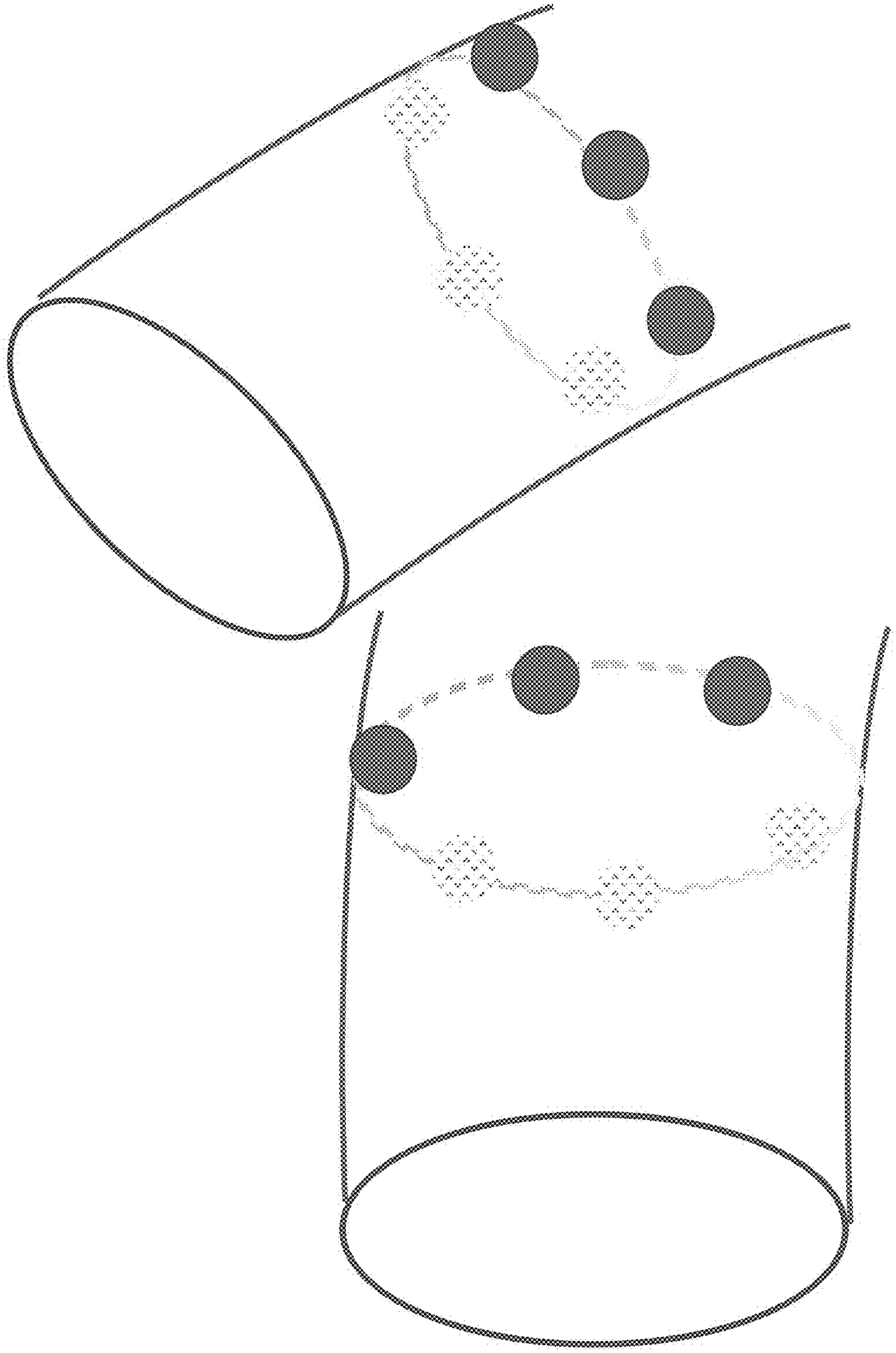

While PFA was initially designed to enable tissue ablation without requiring tissue contact, data has emerged that contact is important for effective ablation as it is with thermal and radiofrequency systems. In one embodiment of the present disclosure, haptic feedback generated by an array of actuators will enable palpation of tissue contact based on data acquired from multiple electrodes simultaneously (e.g., impedance, electrogram, temperature) so that PFA catheter position can be optimized prior to energy delivery by enabling sense of touch confirmation of electrode location as well as identification of effective tissue necrosis (e.g., by using one or more of the same indices for determining tissue contact). FIG. 26E illustrates a circular array of haptic actuators that can be positioned about an extremity (wrist, forearm, finger). Each of 8 actuators is representative of a single electrode and can be arranged about one or 2 extremities as shown in FIG. 26F.

Figure 26G:
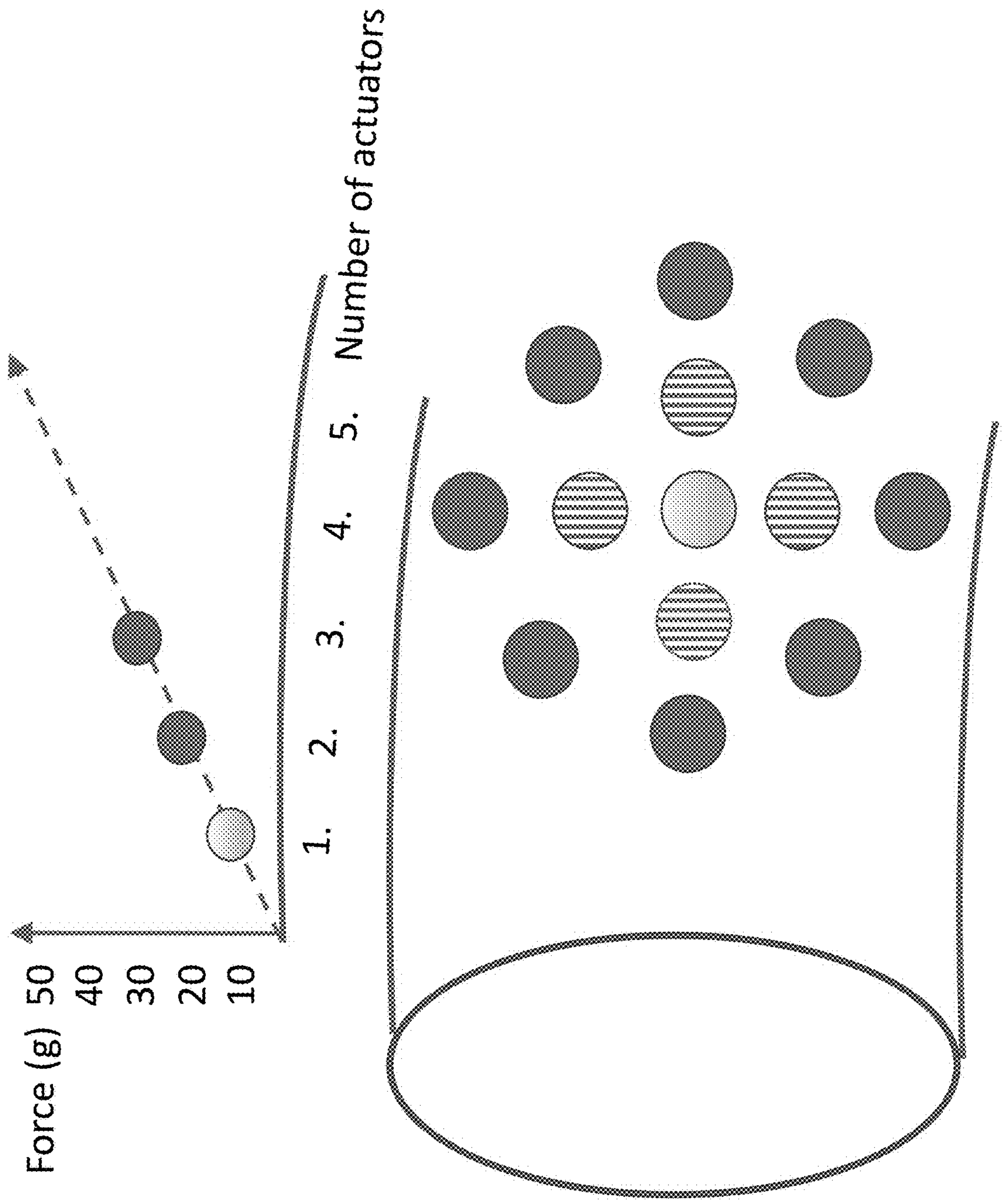

In another embodiment of the present disclosure the geometric arrangement has layers arranged in radial fashion with circular, square, diamond or other shape configuration haptic elements in form of a bullseye wherein activation of the more radially distant actuators indicates a higher amplitude sensed signal. Referring to FIG. 26G the central haptic actuator (light hashed) is representative of too low of a force (or low intra-cardiac pressure, inadequate tissue necrosis), the second diamond configuration of 4 actuators (vertical lines) indicates optimal force (or normal intra-cardiac pressure, adequate tissue necrosis) and the outer circular 8 actuators (solid circles) too high of a signal. Different characteristic haptic effects can be manifest by each level of actuator and any number of configurations can be implemented for the haptic interface including but not limited to those that mimic the geometry of catheter-based electrodes (e.g., ribbon, spherical configuration) and are all within the scope and spirit of the present disclosure.

Haptic Timing System and Counter

The haptic feedback systems taught in this application will have their greatest benefit for users in training or those interventionalists who perform the lowest number of cardiovascular procedures. In an embodiment, the haptic system has a Haptic Timing System and Counter and calculates the duration of time between sensed physiologic and biophysical events and evaluates haptic motor reaction of the operator. A Haptic Counter (600 in FIG. 30) identifies motor reactions, physiologic events, catheter-based signals, and events that are and are not anticipated to be associated with task completion. In this fashion the system provides valuable feedback to the operator, reduces their learning curve, and identifies operational miscues that may lead to deleterious outcome, longer procedural times, and/or lack of success. This can be accomplished any number of ways as described in detail below and the cases described are exemplary and not meant to limit the scope and spirit of the present disclosure.

Figure 27:
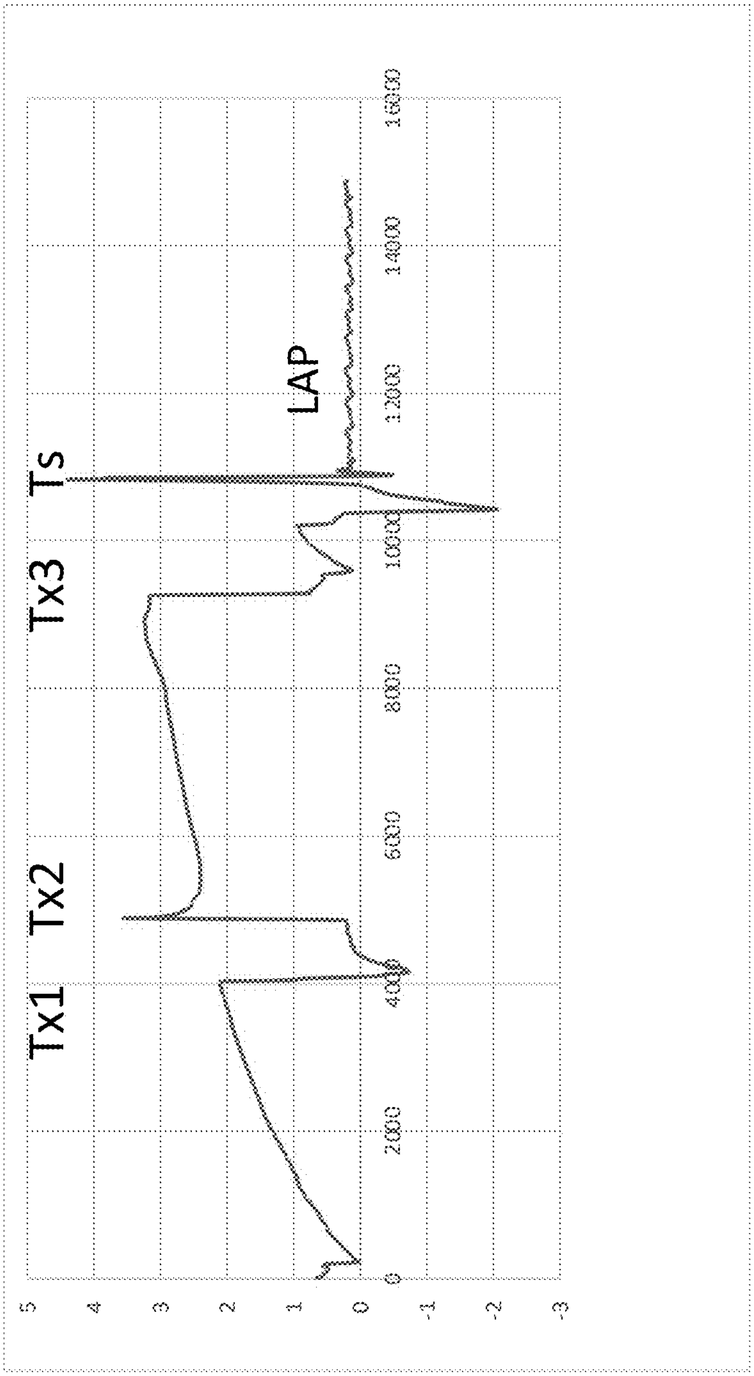
FIG. 27 shows a graphical representation of a complex transeptal puncture waveform.

Referring to FIG. 27, the intracardiac pressure signal has several sharp deflections Tx 1-3, where the slope of the waveform has a morphology that matches an impulse at times of contact with the interatrial septum but in each case the impulse is not followed by a left atrial pressure (LAP) waveform as it is after the successful TP noted at impulse Ts. The Haptic Counter evaluating efficacy of transeptal puncture would count 3 negative points for each of the ineffective attempt at TP, Tx1-3, and a success point for 1 event for Ts. Numbers of success vs. number of failures provides a metric of operator competency when evaluated over many procedures. Haptic Counter (600 in FIG. 30), as will be described in more detail below, can be applied to any procedure including but not limited to attempts to cross a guidewire across a stenotic aortic valve, attempts at ablation of an arrhythmic focus, attempts to deploy a TAVR.

Figure 28A:
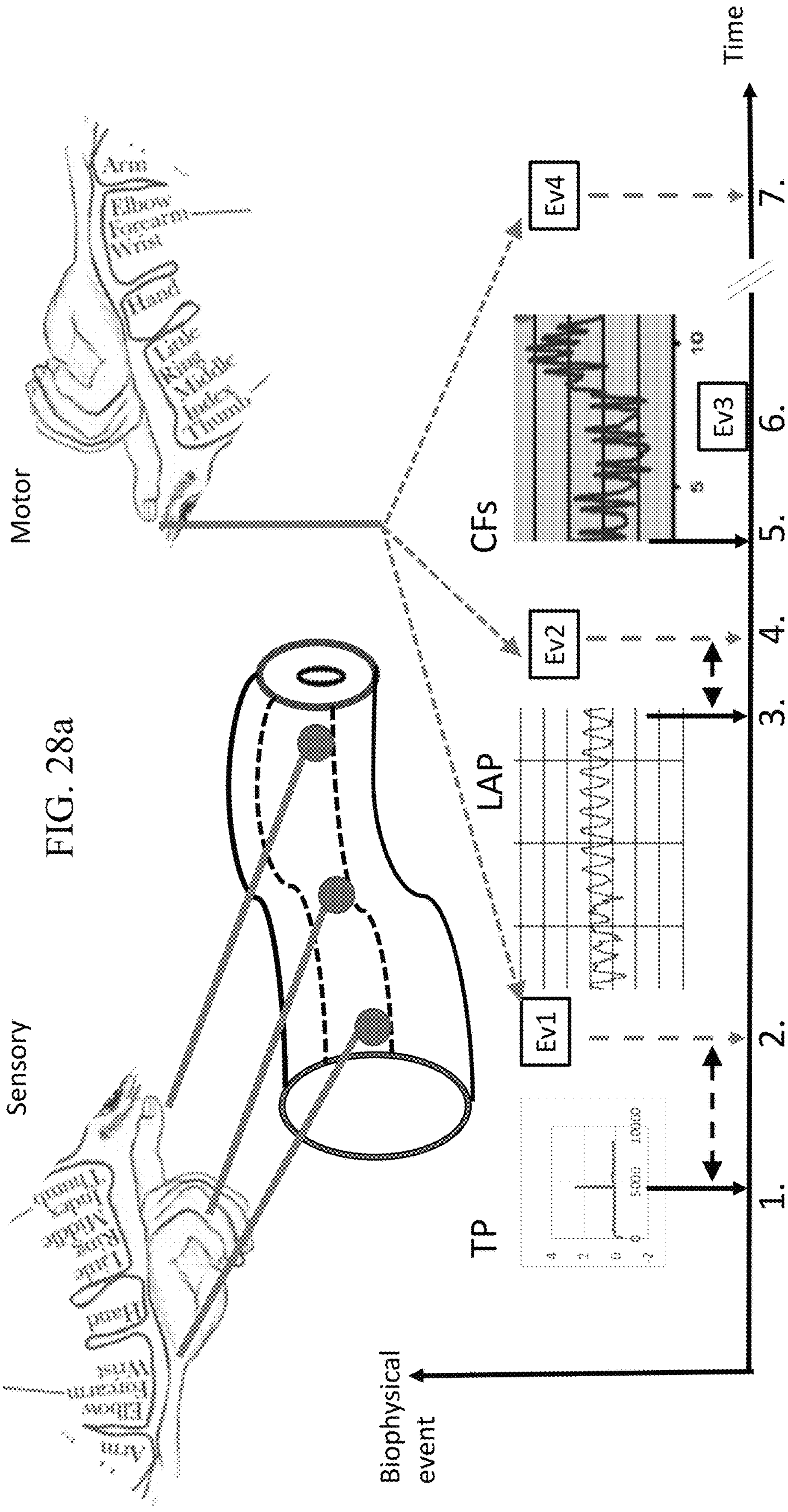
FIG. 28A is a comprehensive depiction schematic and graphical representation of an embodiment of a haptic sleeve system showing temporal relations of haptic timing of the system for electrophysiology procedures.

Referring to FIG. 28A, haptic time stamps of physiological or biophysical events during an electrophysiology procedure inclusive but not limited to time of transeptal puncture, TP (at time 1), are identified and rendered palpable. In various embodiments, these events can be based on sensed physiological signals, the nature of the signals being sensed, as well as, timed events, Ev, in FIGS. 28A and 28B that can be dependent (and determined by monitoring catheter control, positioning, manipulation, and actuation. In various embodiments, the means of monitoring a catheter or inserted instrument does not require modification of the catheter/instrument design and are device agnostic. In FIG. 28A TP starts the timing system. TP is exemplary and the biophysical event can be epicardial puncture or a biophysical signal generated from a catheter or needle crossing any biological tissue plane. Once left atrial pressure (LAP) is sensed this indicates that the operator stopped advancing the guiding catheter (motor command Ev1 at time 2.) and exchanges the transeptal needle for an ablation catheter or other device (e.g., Watchman delivery system, PFA catheter) in preparation for the remainder of the procedure. At time 2 (motor command or catheter actuation Ev1) the system identifies that the operator stopped advancing the guiding catheter with transeptal needle (e.g., via any imaging/tracking modality as known by those experienced in the art or after a prompt elicited by the operator including clicking on an icon or switch) as the operator recognized that there was successful TP. The duration between TP at time 1, and event Ev1. is stored and reflects operator haptic motor reaction time. If the transeptal needle was not exchanged in time and advanced too far there would be risk of cardiac perforation (e.g., across the left atrial free wall and into the aorta). At time 3 the operator exchanges the transeptal needle and places an ablation catheter into the guiding catheter (by way of example) as there is stable LAP signal and the catheter is within the left atrium. The time of this exchange can be identified any number of ways including use of navigational systems, loss of LAP signal, operator setting a new counter via a switch, an operator or observer clicking on an icon located on or not on an inserted instrument, Such events EV are dependent on identifying how an operator controls, steers, positions, orients or otherwise controls an inserted catheter or other means. At time 4 (Ev2) the ablation catheter with contact force sensing system is manipulated towards the anatomic target for ablation, the pulmonary vein os. Once the ablation catheter is opposed to cardiac tissue at time 5, and CF data is obtained, the next motor event associated with appropriate catheter manipulation to be identified is maintenance of a stable contact force (CFs) between the pulmonary vein os and catheter tip at event Ev3 at time 6. Contact force or index of stable catheter tissue opposition is palpable with haptic feedback and ideally proportionate to sensed CF amplitude or alternate tissue contact sensing index.

Completion of ablation about a given pulmonary vein by the operator at Ev4 is identified when there is electrical isolation (e.g., determined by intracardiac EGM) at time 7. This is dependent on catheter-based measurements of intracardiac electrical signals. Stable CF can be determined by any number of methods including but not limited to CF value within a range or standard deviation over a plurality of cardiac cycles (e.g., >10) or designated time frame (e.g., >3 seconds). Statistical assessment of CF stability during the procedure can provide a metric of operator competency. The duration of time to complete the catheter exchange, time from transeptal puncture to delivery of ablation energy, time to maintain stable contact force, time to complete ablation, etc. can all also be measured, stored, and evaluated to determine procedural efficacy and operator competency.

The Haptic Timing System calculates the TP-LAP time and other relevant time frames and stores that information for future reference/scoring. The shorter that duration TP-LAP is, the more successful the transeptal puncture procedure is considered. In cases where the operator delays the catheter exchange, the location of the catheter is mapped (i.e., by any of the imaging systems as known by those experienced in the art and described elsewhere in the application) and stored so there is a recording of the intracardiac anatomic course that the catheter takes and timing of salient events. Likewise, time to complete successful isolation of one or more pulmonary veins relative to time of TP, initial contact with a first pulmonary vein, or times between any number of sensed events, motor commands, procedural completion and the like can be evaluated and dependent on measuring physiological, biophysical signals as well as metrics indicative of catheter control, manipulation, and positioning all of which are transduced and rendered palpable using tactile and/or force feedback.

Figure 28B:
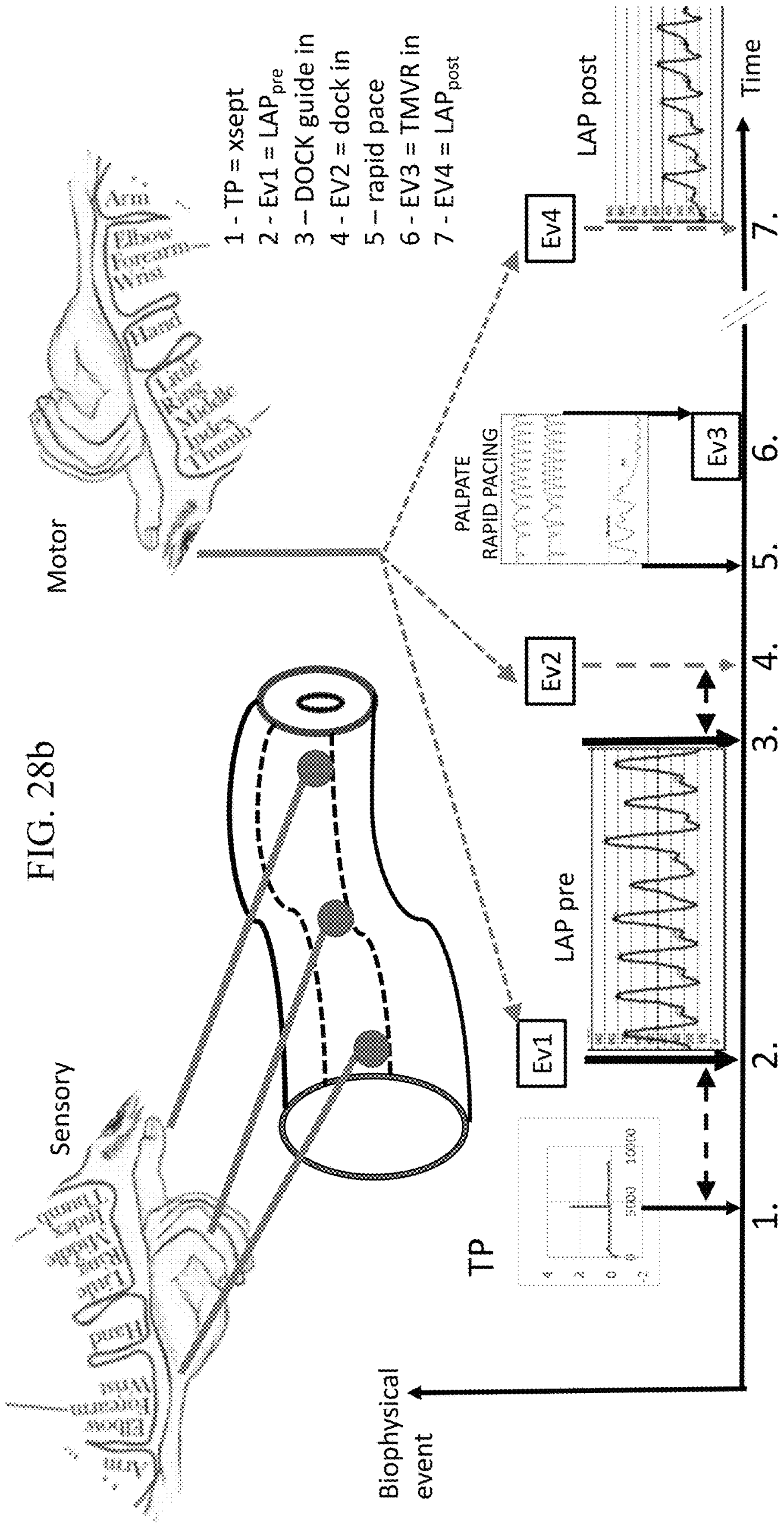
FIG. 28B-28I are a comprehensive depiction schematic and graphical representation of an embodiment of a haptic sleeve system showing temporal relations of haptic timing of the system for structural heart procedures, including.
Figure 28C:
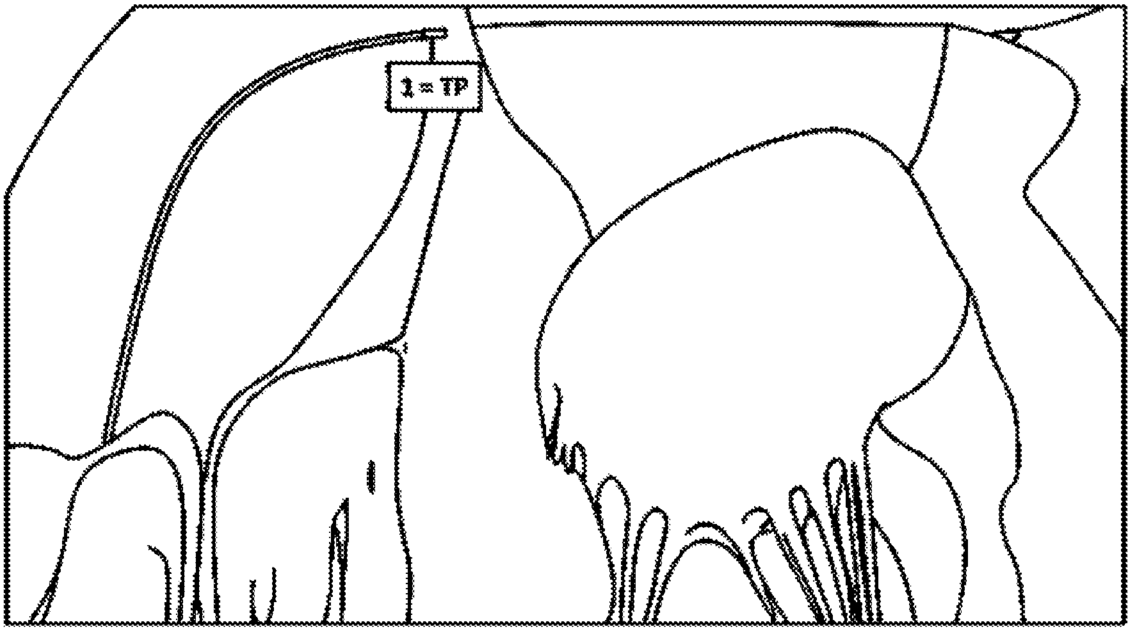
Figure 28D:
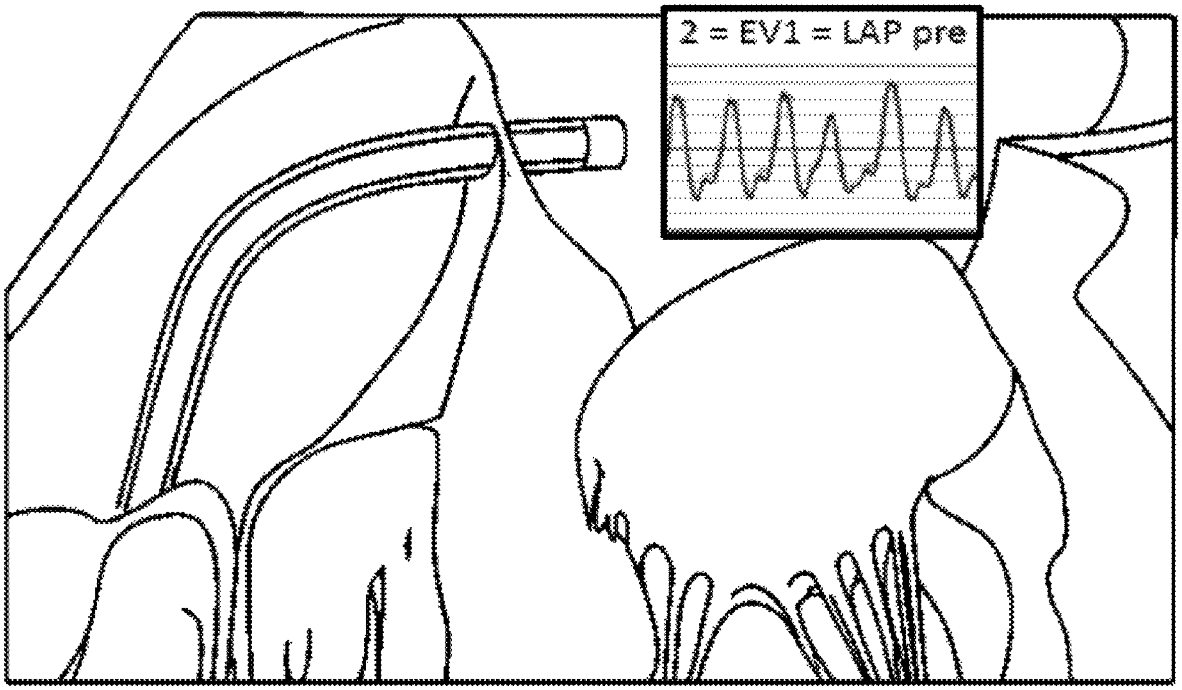
Figure 28E:
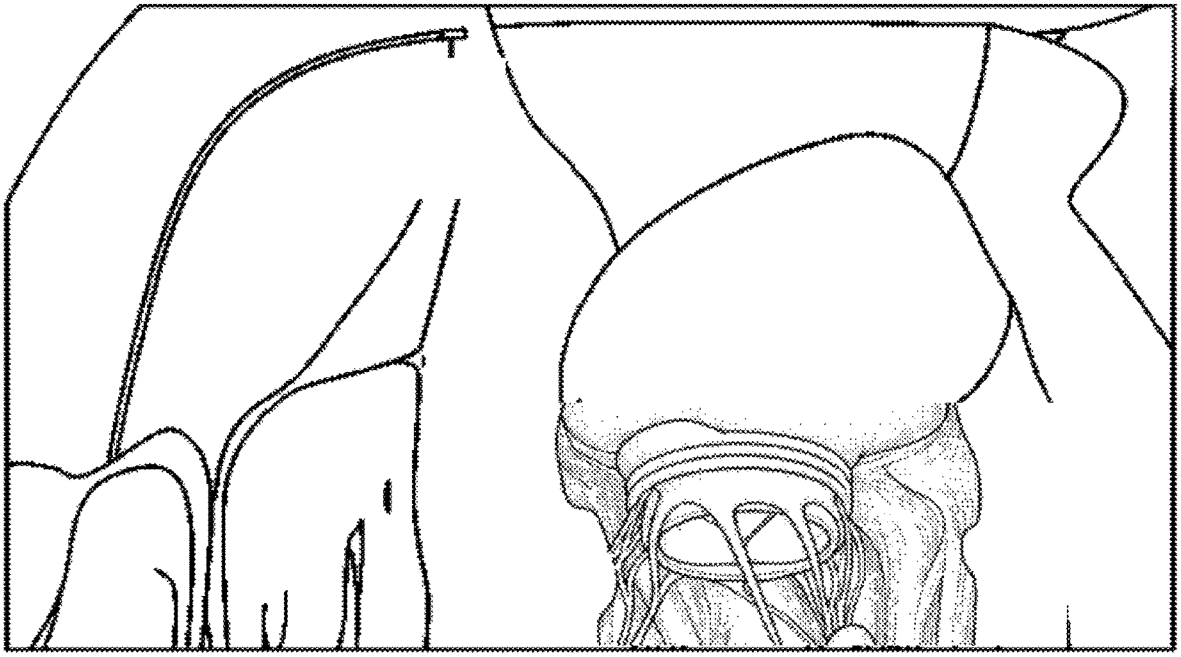
Figure 28F:
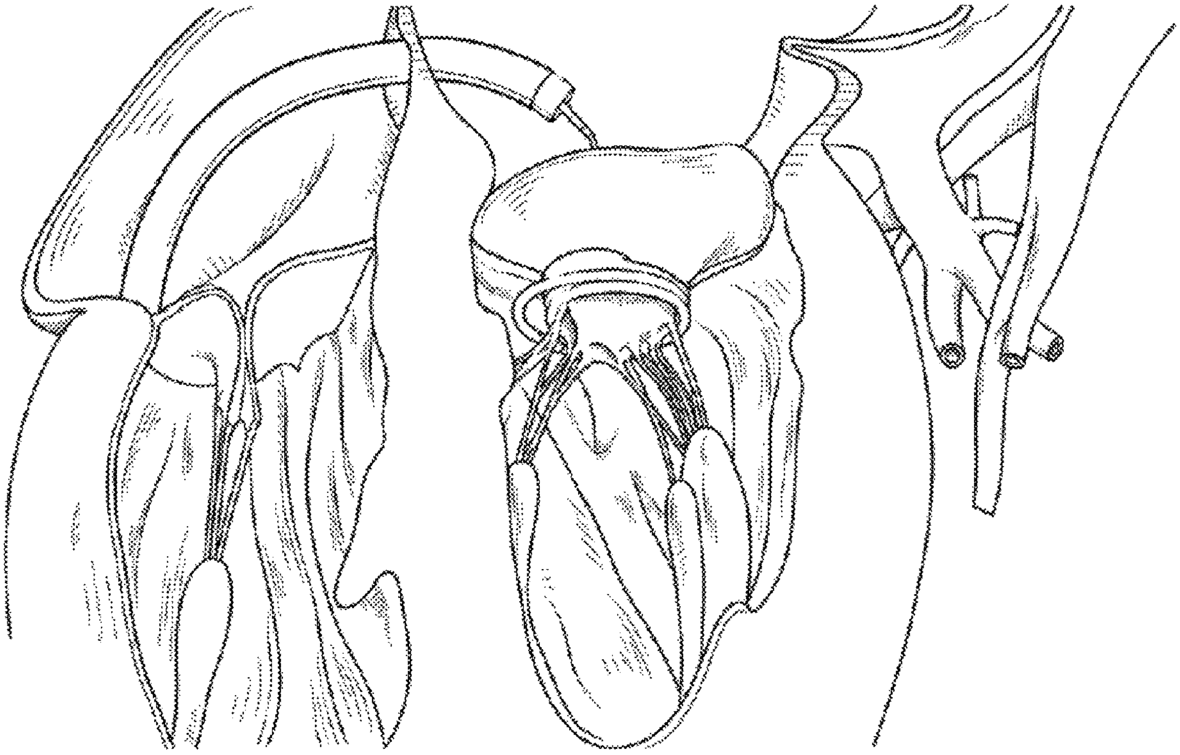
Figure 28G:
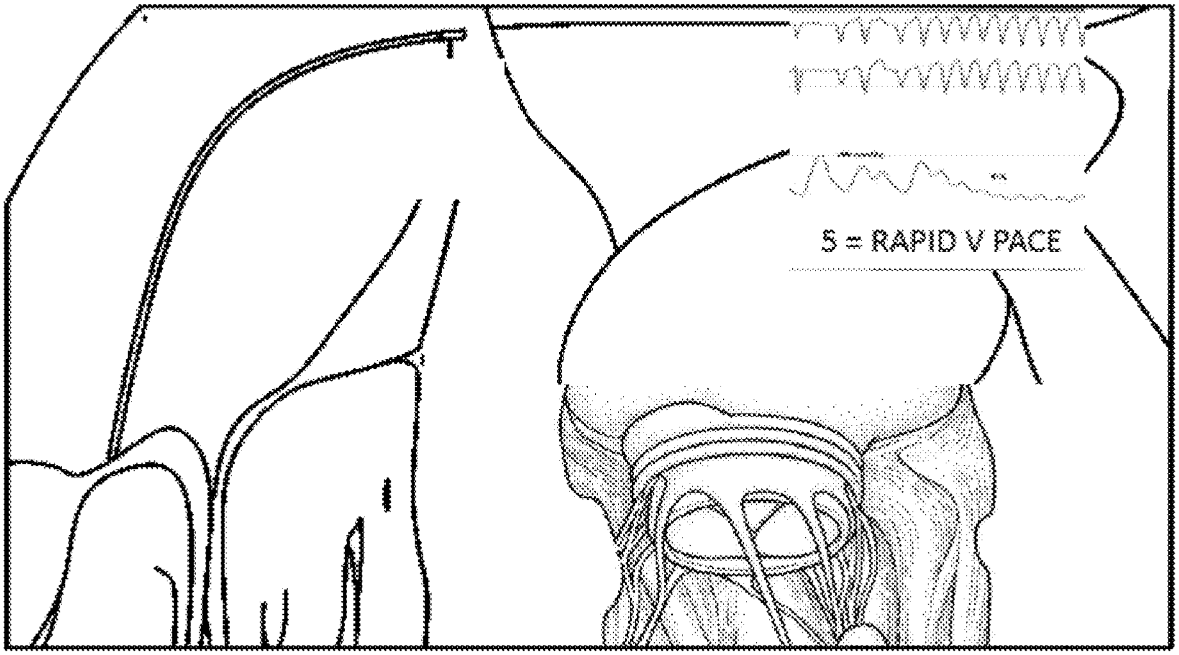
Figure 28H:
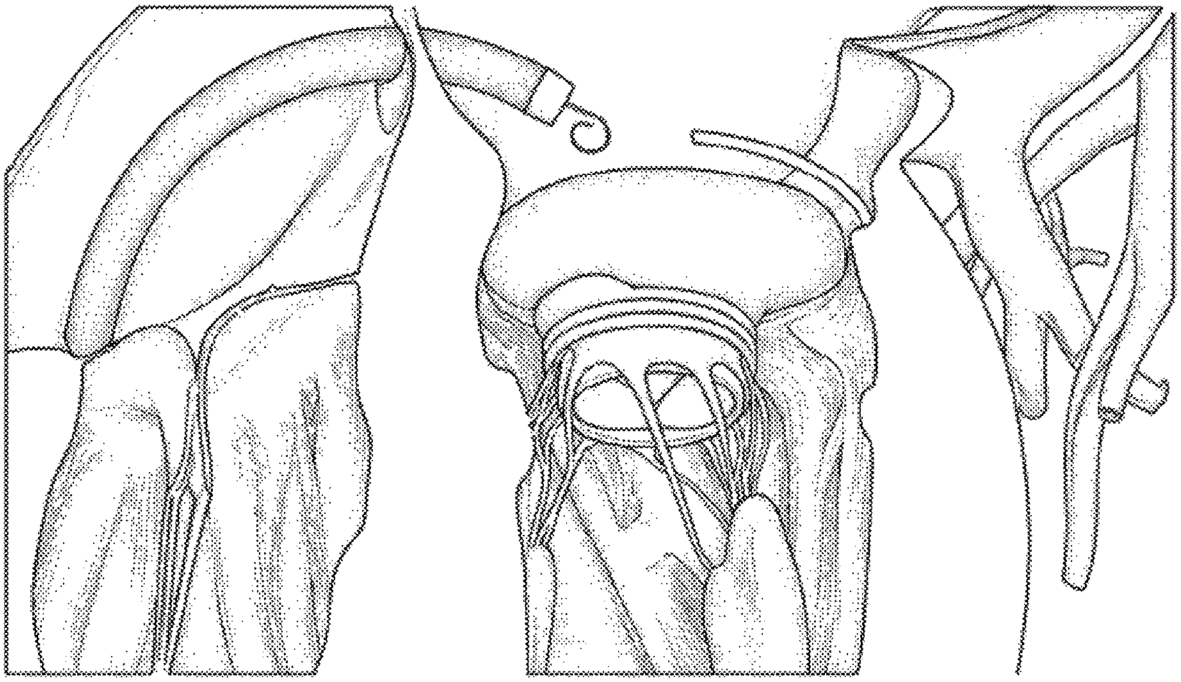
Figure 28I:
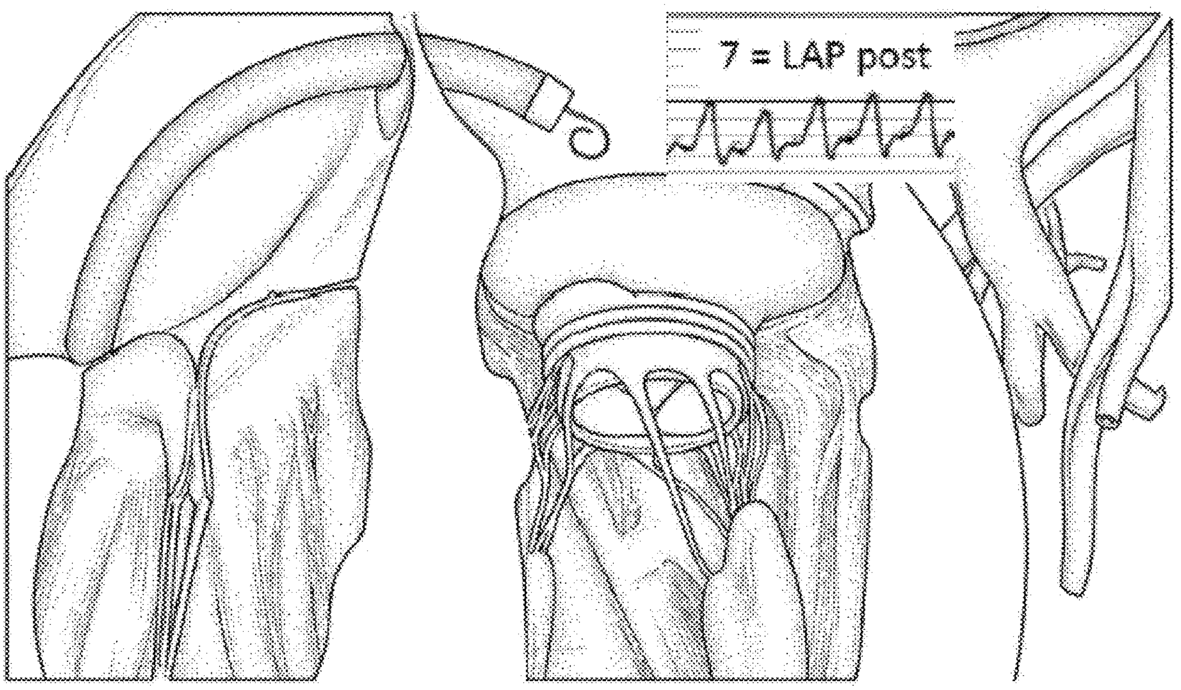

In structural heart embodiments, a plurality of biophysical or physiological indices are rendered palpable and evaluated to assess operator performance/motor reaction time, along with times of salient events dependent on control, manipulation, and positioning of an inserted instrument or catheter during structural heart procedures. Such structural heart procedures include but are not limited to valve repair or replacement, correction of congenital heart defects, or any cardiac device implant. Referring to FIG. 28*b* for transcatheter mitral valve replacement, TMVR, Time 1 is time of transeptal puncture, time 2=Ev1 is time of achievement of catheter stability within the left atrium and successful end hole manometric measurement of high amplitude left atrial pressure, LAP, in the setting of severe mitral regurgitation, time 3 is a indicator of deployment of a dock guide used to secure a docking mechanism for a bioprosthetic mitral valve, time 4=Ev2 is when the actual dock is positioned, time 5 is initiation and continuation of rapid ventricular pacing used to halt cardiac contractility during catheter manipulation for implantation of the mitral bioprosthesis, and time 6=Ev3 is actual time of implant of the bioprosthesis. Once all the guiding catheters and equipment are removed the guiding catheter remains in the left atrium and time 7=Ev4 is rendered palpable (e.g., as a palpable impulse or other haptic stimulus) and thereafter LAP post is palpable as a lower amplitude haptic pulsation relative to LAP pre until the guiding catheter is removed. In another embodiment, artificial intelligence or machine learning techniques can be utilized to evaluate sensed physiological signals, event timing, and for determination of salient events dependent on control, manipulation, and positioning of an inserted instrument or catheter during structural heart and electrophysiology procedures based on the composite of data acquired during any given procedure(s). The cases described herein are meant to be exemplary and not limit the present disclosure in spirit or scope. Below in Table I is a list of physiological, biophysical and catheter-based metrics that is not meant to be all inclusive.

TABLE I

| |
|---|
| TP-LAP |
| TP- contact force stability (CFs) |
| TP-Watchman Deployment |
| Doppler flow wire across stenotic valve - catheter entering LVOT |
| Doppler flow wire across stenotic valve - TAVR deployment |
| CFs-electrical isolation PV |
| TP = transeptal puncture |
| $LAP_{pre}$ - left atrial pressure prior to bioprosthetic valve implant |
| DOCK - positioning of a dock guide in the mitral annulus |
| dock in - positioning of the dock in the mitral annulus |
| rapid pace |
| TMVR in - time of successful implant of bioprosthetic mitral valve bioprostheiss |
| $LAP_{post}$ - left atrial pressure after bioprosthetic valve implant |

In embodiments, specific clinical scenarios complicate cardiovascular interventions, and a scoring system is needed to make a determination of procedural complexity. This is a standard of practice in percutaneous coronary interventions and is known as the Syntax score. Similar scoring systems exist for catheter-based valve repair/replacement and is accounted for when assessing risk: benefit of a given procedural technique. The present disclosure haptic timing system and haptic counter also accounts for level of anatomic and or physiologic complexity during cardiovascular procedures including electrophysiologic interventions including catheter ablation of cardiac arrhythmia, left atrial appendage isolation, and the like. By way of example, left atrial size, valvular regurgitation severity, intracardiac or intravascular blood flow or pressure, pulmonary vein anatomy, history of prior pulmonary vein isolation are factors that are weighted in the analysis of operator performance. These factors can be analyzed when evaluating a given clinician's competency using Haptic Counter and Timing System. Likewise, the efficacy of the Haptic System can be made using research protocols that call for a comparison between interventions with and without haptic feedback can be made by not enabling haptic actuators to be functional during some cases and other cases of like complexity.

Any number of cardiovascular interventions are within the scope and spirit of the present disclosure and there is no limitation on which procedures can benefit from a Haptic Counter and Timing System; ablation of atrial fibrillation and TAVR are exemplary.

Optimization of Haptic Motor Reaction Time

As discussed, procedural efficacy and ideal risk: benefit ratio is expected to be the outcome of optimal performance of an interventionalist who has the shortest haptic motor reaction times. This embodiment of the present disclosure focuses on methods for teaching low volume operators and those in training how to improve their reaction times by monitoring central and peripheral neurologic function during real time procedures and using haptic simulations that incorporate visual and haptic feedback data acquired during real time procedures. The simulations can be developed using visual, auditory, haptic data acquired during prior interventions where stored visual information can include 3 D navigational systems, fluoroscopic images, cardiac ultrasound, acoustic signals, impedance and electromagnetic data, contact force information, etc. and haptic data is generated by processing landmark signals such as transeptal puncture pressure waveforms, intracardiac/intravascular pressure signals, Doppler ultrasound or other acoustic means for evaluation of physiological/transvalvular data, and the like. Likewise, testing and optimization of performance can be accomplished to some extent as an initial evaluation with bench testing as described in detail below which was utilized to calculate signal processing time of a prototype haptic feedback system and compare haptic motor reaction time to visual motor reaction time to a simple on-off display. As described in detail below, this work demonstrated that mean signal processing time was 0.038 seconds for this system and significantly (10×) less than the time for normal cardiac ventricular systole and haptic motor reaction time for novice subjects was statistically significantly less than the visual reaction time for historical controls to react to the termination of a simple continuously visible stimulus 500 msecs in duration.

To better define and monitor user haptic motor reaction time, this embodiment implements monitoring of the sensory and motor aspects of the central and peripheral nervous system. Testing of a prototype haptic system was performed to define the robustness of signal processing and haptic motor reaction times of novice subjects.

A typical heartbeat's combined atrial and ventricular electrical depolarization (onset of P wave till end of the QRS complex or P-QRS interval) is normally less than 400 msecs. One total cardiac cycle is normally between 600 and 1200 msecs in duration and includes depolarization and repolarization phases. Cardiac systole is defined by a normal QTc interval=0.380 seconds. To define signal processing time of a haptic computing system through an analysis of the time between contact of a proprietary sensorized catheter touching *Gallus domesticus* skeletal muscle ("tissue") and detectable action of an actuator within a proprietary hand-held handle. The novel contact sensors used for this embodiment may be embedded as a circumferential array within a segment of a 9 French guiding catheter. The input data from the sensors was processed using a control and data acquisition system. The computing system output signals were input into a driver and haptic actuator contained within the handle. This handle was a 3D printed cylindrical contoured prototype fabricated with a polyamide (PA 2200); 120 mm long; 32 mm maximal diameter; Shore D hardness=75.

M-mode ultrasonography was used to evaluate the system's delay time. The tissue was secured in position and placed atop of and in contact with a phased array ultrasound transducer (GE Vivid i, GE Healthcare, Milwaukee, WI). Acoustically conductive gel medium was implemented as often as needed to couple the transducer to the tissue. The sensorized catheter was abruptly placed in contact with an approximately 2 cm thick segment of tissue as an impulse, at an incident angle of 90 degrees causing tissue agitation detected with M-mode ultrasound, which was time=0. The impulse generated from the tissue contact then triggered the haptic actuator to cause a second deformation upon the same tissue likewise detectable with M-mode ultrasound. The system's delay time is the total of processing and any mechanical delays from the time for tissue motion detected at the level of the sensorized catheter to the time for reaction of the haptic actuator. Data was acquired during thirteen consecutive time delays, t, between Impact 1 and detection of the haptic force upon the tissue as recorded from each experiment judged to have adequate image quality for interpretation.

Figure 29A:
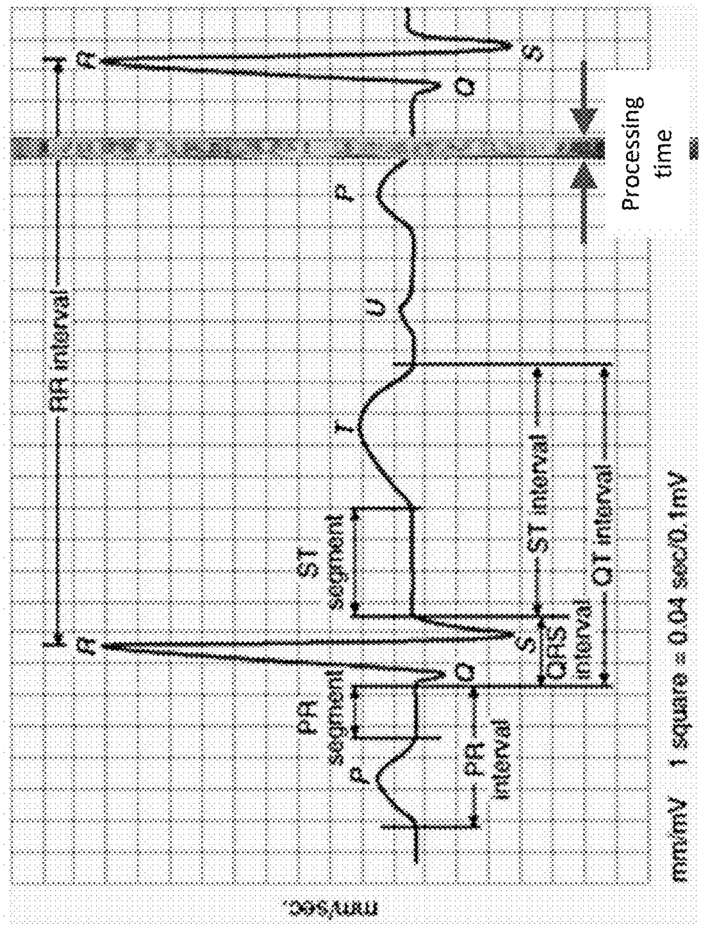
FIG. 29A shows a graphical representation of an embodiment utilizing M mode ultrasonic measurement of signal processing time relative to ECG.

The mean signal processing time was 0.038 seconds (n=13; SD=9.4 msecs). The mean processing time plus the time for the handle to impart a haptic effect upon the tissue was significantly (10×) less than the time for normal cardiac ventricular systole (p<0.0001; unpaired t test) as defined by a normal duration QTc interval=0.380 seconds and a fraction of a normal PR interval as is depicted in FIG. 29A where the M mode ultrasound signal is superimposed on a sample ECG tracing.

Figure 29B:
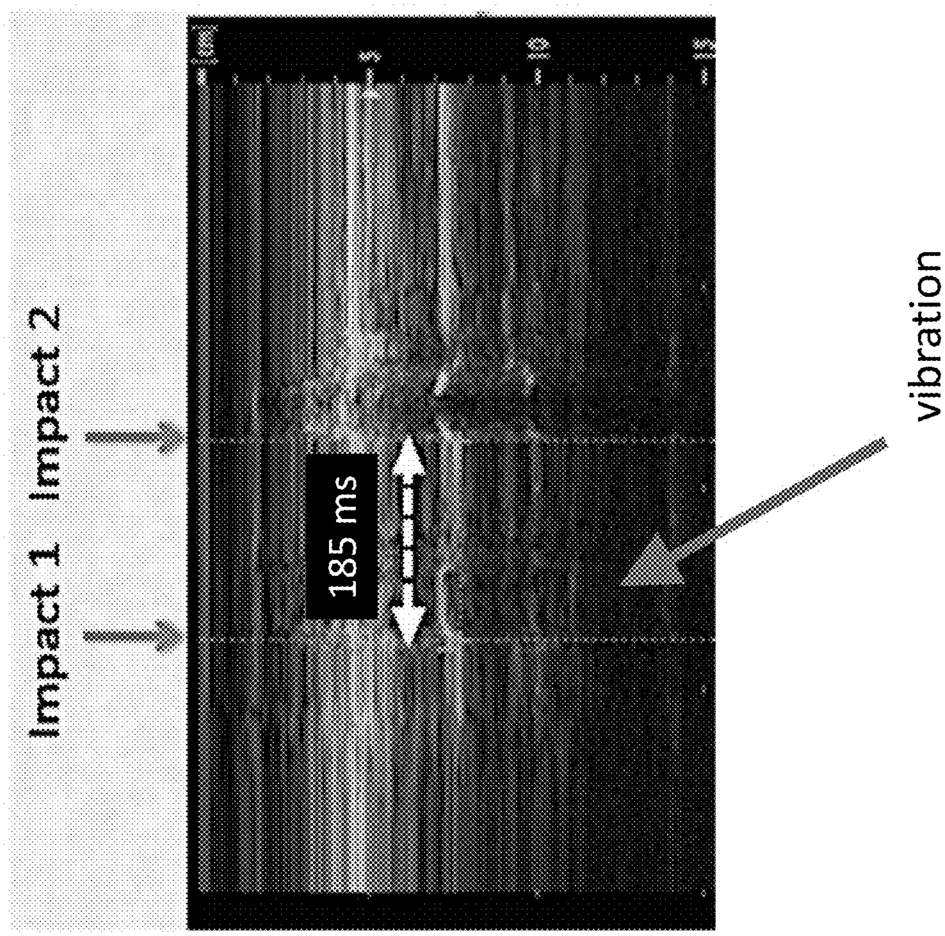
FIG. 29B shows a pictorial representation of an embodiment of a haptic sleeve system using M mode ultrasonic measurement of haptic motor reaction time corresponding to FIG. 29A.

In various embodiments, it is hypothesized that tactile: motor reaction time would be statistically significantly less than visual: motor reaction time to even a simple on-off visual display and to time for cardiac systole. The same M-mode ultrasound technique for Phase I was applied to measure subject haptic-motor reaction time from the time the proprietary sensorized catheter impacted tissue at Impact 1 in FIG. 29B (not performed by, nor visualized by, the subject) to time of motor response of blinded subjects holding the handle in one hand and impacting the same tissue with an instrument using the contralateral hand upon sensing haptic feedback as shown FIG. 29B: impact 2. Thus, the total time recorded accounted for the time for activation of the sensorized catheter, signal processing, generated haptic effect at the level of the handle, operator palpation of the action of the actuator within the handle, and ultrasonic detection of motor response of the operator to palpation of haptic effect. Each operator was allowed to practice five experiments to become familiar with the experiment design prior to data collection. Tactile: motor reaction time components of the cardiac cycle were compared to visual: motor reaction time of historical controls reacting to a simple, static on-off visual display as described in a study performed by Howe (E. Howe. The Plymouth Student Scientist, 2009,2, (1), 90-107.

Data was acquired a total of 5 consecutive times for each of two subjects (n=10) and the time delay, t, was recorded from each experiment judged to ha (ve adequate image quality for interpretation for each of two physicians, subjects A and B, a 49-year-old male interventional cardiologist, and a 54-year-old female echocardiographer, respectively. Calculations of the total time delay were performed inclusive and exclusive of processing time to better differentiate between system delays and operator performance. Results were compared between two subjects and compared these data to studies of visual: motor reaction times using historical controls as described in detail below.

For a total of n=10 experiments, exclusive of mean processing time, 5 for each of two subjects, the mean t=166 msecs (SD=34) for subject A, and 203 msecs (SD=16.0) for subject B; (p=0.06 between two subjects). The mean reaction time for both subjects combined, exclusive of mean processing time, n=10 experiments, was t=185 msecs (SD=32). For a total of n=10 experiments inclusive of processing time, 5 for each of two subjects, the mean t=204 msecs (SD=34) for subject A, and 241 msecs (SD=16) for subject B (p=0.06 between two subjects). The mean reaction time for n=10 experiments combined for both subjects=223 msecs (SD=32). The mean difference between the initial and last 5 experiments for both subjects (total n=10), exclusive of processing time, was 24 msecs shorter in duration for the terminal 5 studies (p=NS) when accounting for two subjects' data.

Visual motor reaction time in the Howe study was determined by analysis of subject reaction time (visual to motor, left and right hands) in 93 subjects with a mean age of 25 (+/−5.56) years. This work demonstrated that while constantly observing a screen, the mean reaction time for subjects to press a spacebar (analyzed 200 times) after seeing a continuous 500 msec visual stimulus disappear averaged 321.8 msecs after termination of the visual stimulus (and 821.8 msecs after initial appearance of the visual stimulus).

Figure 29C:
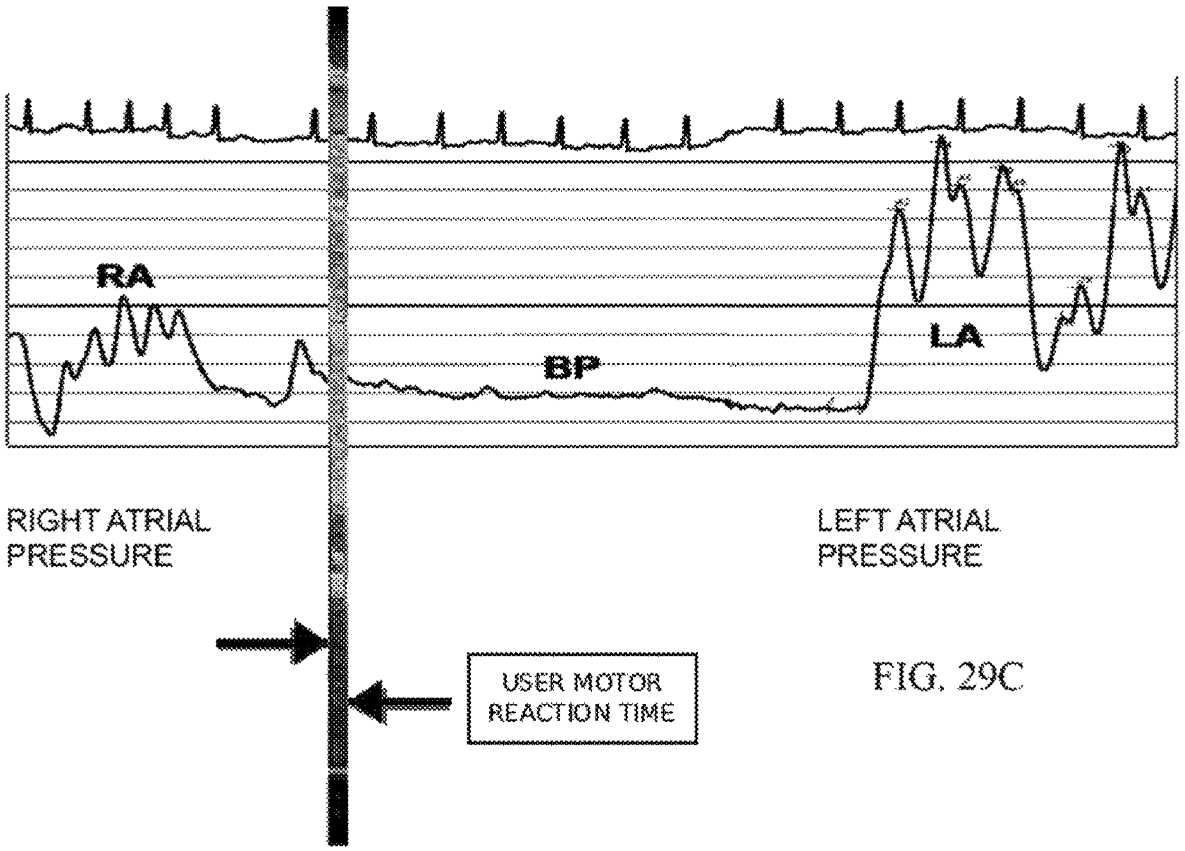
FIG. 29C shows a graphical representation of temporal relationship between user motor reaction time and time to complete transeptal puncture corresponding to the haptic sleeve system of FIG. 29B.

The time for operator reaction to haptic feedback with system processing was substantially less (4.5 times) than the time for one normal cardiac cycle for a person with a heart rate of 60 beats per minute, and less (1.8 times) than the time for normal cardiac atrial-ventricular electrical depolarization. The mean user reaction time for both subjects, exclusive of system processing=185 msecs (SD=32), which was statistically significantly less than the visual reaction time for historical controls to react to the termination of a continuously visible stimulus 500 msecs in duration; n=93; mean=321.8 msecs (SD=38.6); p<0.0001 (unpaired t-test) at 95% confidence level. Furthermore, mean user reaction time with processing=223 msecs (SD=32), which is also statistically significantly less than the visual reaction time for historical controls to react to the termination of a constantly visible stimulus 500 msecs in duration; n=93; mean=321.8 msecs (SD=38.6); p<0.0001 (unpaired t test) at 95% confidence level. FIG. 29C demonstrates mean haptic motor reaction time relative to an end hole manometry pressure waveform acquired during transeptal puncture. RA and LA are right and left atrial pressure, and BP is blunted pressure signal during contact with the interatrial septum.

Haptic Cardiovascular Brain Interface

Brain computer interface (BCI) technology is an evolving field with focus on assistive and rehabilitative systems and includes invasive, semi-invasive, and non-invasive means for monitoring neurologic impulses. While BCI technology has historically focused on improving functionality of patients with severe motor deficits/paralysis, the present disclosure employs BCI as a means for monitoring and optimizing haptic motor reaction times and testing subject's competency to perform invasive cardiovascular procedures or neurometric performance. BCI devices enable direct communication between the brain and external devices by recording and decoding signals from specific anatomic locations in the central nervous system (CNS) such as the precentral gyrus/motor cortex and have been used successfully even in patients who are completely in locked-in states. While this has been done with implanted microelectrode arrays it is also possible using less invasive techniques with electrode arrays positioned along the brain's superior sagittal sinus using vascular access via the jugular vein and a decoder located in a subcutaneous tissue location that analyzes CNS movement signals and translates these into actions using computer navigation. While a BCI that requires implantation of an intravascular or intracerebral electrode array is not intended for use in the current application, non-invasive means for monitoring CNS activity can be implemented as known by those experienced in the art.

Electroencephalography (EEG) is a commonly used modality for assessment of seizure and other neurological disorders including level of awareness/consciousness/attention. EEG records brain wave patterns with skin surface electrodes placed on the scalp over specific anatomic locations where underlying brain wave signals are acquired. Motor imagery (MI), P300, and steady stage visual evoked potentials are known methodologies. MI assesses the psychological process of movement prior to muscle actuation while P300 identifies peak EEG signal related to human event potentials. Thus, the mere thought process of performing a motor action can be detected using MI and the captured signal commands can command an assistive device to complete a specified movement (e.g., using an orthotic device). BCIs are also being used for entertainment purposes as game controllers and provide novel input channels and have been demonstrated to be able to assess cognitive status and attention deficits. The EEG monitoring apparatus in the current application is ideally wireless, compact, portable, multichannel, has optimal signal to noise ratio, and spatiotemporal resolution and is comfortable to wear as a headset as known by those experienced in the art. Magnetoencephalography (MEG) is also a non-invasive method for monitoring brain activity on a millisecond scale and provides neuroimaging/brain mapping with magnetometers. Magnetometers can include superconducting quantum interference devices and spin exchange relaxation-free sensors. These exemplary systems and others can be used to localize brain activity, assess cerebral functionality, and provide neurofeedback. MEG systems are currently not portable and require a large magnetometer while an EEG can be used in an ambulatory setting.

Figure 31:
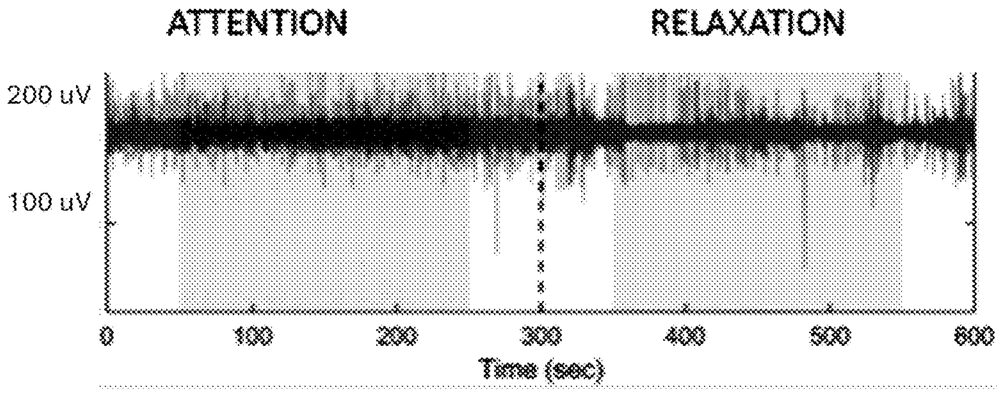
FIG. 31 shows a graphical representation of EEG waveform nomenclature representing states of attention that have different characteristic EEG patterns than states of relaxation.

Specific EEG waveforms (Table II) are associated with CNS directed motor, somatosensory, and sleep-wake cycle activities (FIG. 31) as known by those experienced in the art and analyzed for determination of an operator's psychological status and task-oriented performance.

Table II

- α activity: electromagnetic waves ranging between 8 and 13 Hz in frequency, and between 30 and 50 μV in amplitude. This type of periodic wave is produced in the parietal and occipital regions of the brain when in a state of consciousness, quiet, or at rest. When thinking, blinking, or otherwise stimulated, a waves disappear. This is known as an alpha block.
- β activity: electromagnetic waves ranging between 14 and 30 Hz in frequency, and between 5 and 20 μV in amplitude. This type of activity occurs in the frontal region when people are conscious and alert. These waves are particularly apparent when a person is thinking or receiving sensory stimulation.
- θ activity: electromagnetic waves ranging between 4 and 7 Hz in frequency, with an amplitude of less than 30 μV. This activity primarily occurs in the parietal and temporal regions of the brain. Such waves are produced when people experience emotional pressure, interruptions of consciousness, or deep physical relaxation.
- δ activity: electromagnetic waves ranging between 0.5 and 3 Hz in frequency, and between 100 and 200 μV in amplitude. In a conscious state, most adults exhibit almost no & activity; instead, this activity occurs when in a deep sleep, unconscious, anesthetized, or lacking oxygen.
- γ activity: electromagnetic waves ranging between 31 and 50 Hz in frequency, and between 5 and 10 μV in amplitude. Recent studies have found that γ activity is related to selective attention. Other studies have also highlighted that this activity is related to cognition and perceptual activity.

States of attention have different characteristic EEG patterns than states of relaxation (e.g., alpha and beta waves) and specific types of signal processing can be applied to discern attention deficits even with a one channel EEG, Journal of Medical and Biological Engineering volume 40, pages 230-238 (2020). Mobile inexpensive EEG sensors are capable of detecting degree of attention and can be utilized in students. Sensors (Basel). 2013 August; 13 (8): 10273-10286. For example, Mu rhythm is a type of alpha rhythm EEG signal that is detected by electrodes positioned in the more central head regions and has an arch like morphology and is apparent when there is motor activity of the contralateral limbs or even from thinking about initiating motor activity. Theta waves have a frequency of 4 to 7 Hz and are brought on by drowsiness and most notable in the frontocentral head region replacing alpha rhythm early on in drowsiness and useful for detecting lower level of alertness. Likewise, Ctenoids are 14 and 6 Hz positive spikes associated with drowsiness and most apparent as unilateral, bisynchronous or asynchronous regular repetitions with arciform morphology over the posterior and temporal regions. Ultra-fast EEG activity is seen in cognitive states and event-related potentials with frequencies over 200 Hz correlating to somatosensory stimulation and motor movements. This is not meant to be an exhaustive review of EEG monitoring and the reader is referred to references known by those experienced in the art (e.g., Nayak, C S, Anikumar A C. EEG Normal Waveforms. StatPearls Publishing. January 2022).

The types of energy or fields that exist in a human brain include electromagnetic and a lesser-known quantum field. Electromagnetic field (EMF) is dominant and relates to purely motor and sensory inputs while quantum field (QF) energy is more a function of brain cognition. EMF is caused by action potentials or electrical signals that travel along nerves (axons) and release chemicals known as neurotransmitters at synapses generating a simultaneous magnetic field or electromagnetic field (EMF) arising as a result of an individual's interaction with the external environment and a function of the five senses (including sense of touch), or even from within the brain itself (during thought, dreaming, virtual reality, hypnosis) not necessitating an external stimulus. QF energy relates to a oneness with the universe as one consciousness and is in form of light energy (lower frequency, lower wavelength not in the visible spectrum, non-directional) rather than as an electric feature (Newtonian). Thus, the brain can be viewed in both a particle (anatomical) and wave form. Brain waves are classifiable as those detected using EEG, MEG based on electromagnetic energy, as well as waves that originate from brain anatomical particles at a quantum physics level/quantum field at a subatomic level that is believed to be attributable to behavior (people mind).

In embodiments of the present disclosure, the brain waves are measured in the most simplistic application as to determine user motor reaction time and level of attentiveness but can also be analyzed as part of a computer brain interface for analysis of cognition, attention, overall performance, and implementation for actions perceived and performed in the metaverse. In addition to training users, such an application can be used for virtual reality, entertainment, and gaming purposes. For more detailed explanation on QF, see Malahs J Med Sci. 2020 February; 27 (1): 1-5 and its associated references. For the purposes of the embodiments of the present disclosure such central nervous system somatosensory recording devices are herein referred to as CNSrd and those discussed are by way of example and in no way limit the scope and spirit of the invention.

Monitoring of motor and peripheral nerve impulses can be accomplished using skin surface or inserted electrodes that obtain signals from peripheral nerves/muscles such as electroneurogram (ENG), nerve conduction velocity (NCV) and electromyograms (EMG) as known by those experienced in the art. Analog physiologic signals whether originating centrally or peripherally are amplified, filtered, optimized for signal to noise ratio, and digitized and processed using digital logic as to derive the most relevant waveforms/data (e.g., thresholding, principal component analysis, template matching). In embodiments, decoding algorithms and artificial intelligence are utilized to derive and identify the salient signals for analysis. Conventional (surface electrode) electrodiagnostics identify peripheral neuropathy and peripheral nerve entrapment with the Sensory Nerve Action Potential (SNAP) using conventional skin prep gel and conductive adhesive gel to conform sensing electrodes in the proper skin location. While surface electrode SNAP is a proven commonly used electrodiagnostic measure, magneto-neurography techniques are in development, capable of compound action current measurement in the peripheral nerve and muscle. Super conducting quantum interference devices (SQUID) sensor arrays are a non-invasive diagnostic tool employed to detect cortical neuronal action potentials with magnetoencephalography (MEG). Peripheral nerve action currents in the human upper extremity (median and ulnar nerve; termed magnetoneurography have also been successfully detected with SQUID sensor arrays. Conventional SQUID sensor requires cryogenic temperature provided with liquid helium (4 K or −269° C.) and magnetically shielded rooms and are housed in a rigid Dewar which prohibit adjacent placement to the sensory, motor nerve, or the target muscle that inherently requires highly mobile and conformal sensor arrays. QuSpin OPM sensors have been developed and are conformal with a 6.5 mm sensor stand-off that in aggregate contribute to an improved magnetic signal-to-noise ratio therefore capable of surpassing current SQUID sensor technology due to closer proximity to the neuronal source and can detect compound muscle action currents consistent with motor neuron activation and have been used to measure upper extremity action currents equivalent to the SNAP with conventional surface electrodes Front. Physiol., 18 Mar. 2022 https://doi.org/10.3389/fphys.2022. 798376. For the purposes of the present disclosure such peripheral nervous system somatosensory recording devices are exemplary and herein referred to as PNSrd and those discussed are by way of example and in no way limit the scope and spirit of the present disclosure. Non-invasive monitoring techniques are the methodology used in embodiments.

Figure 30:
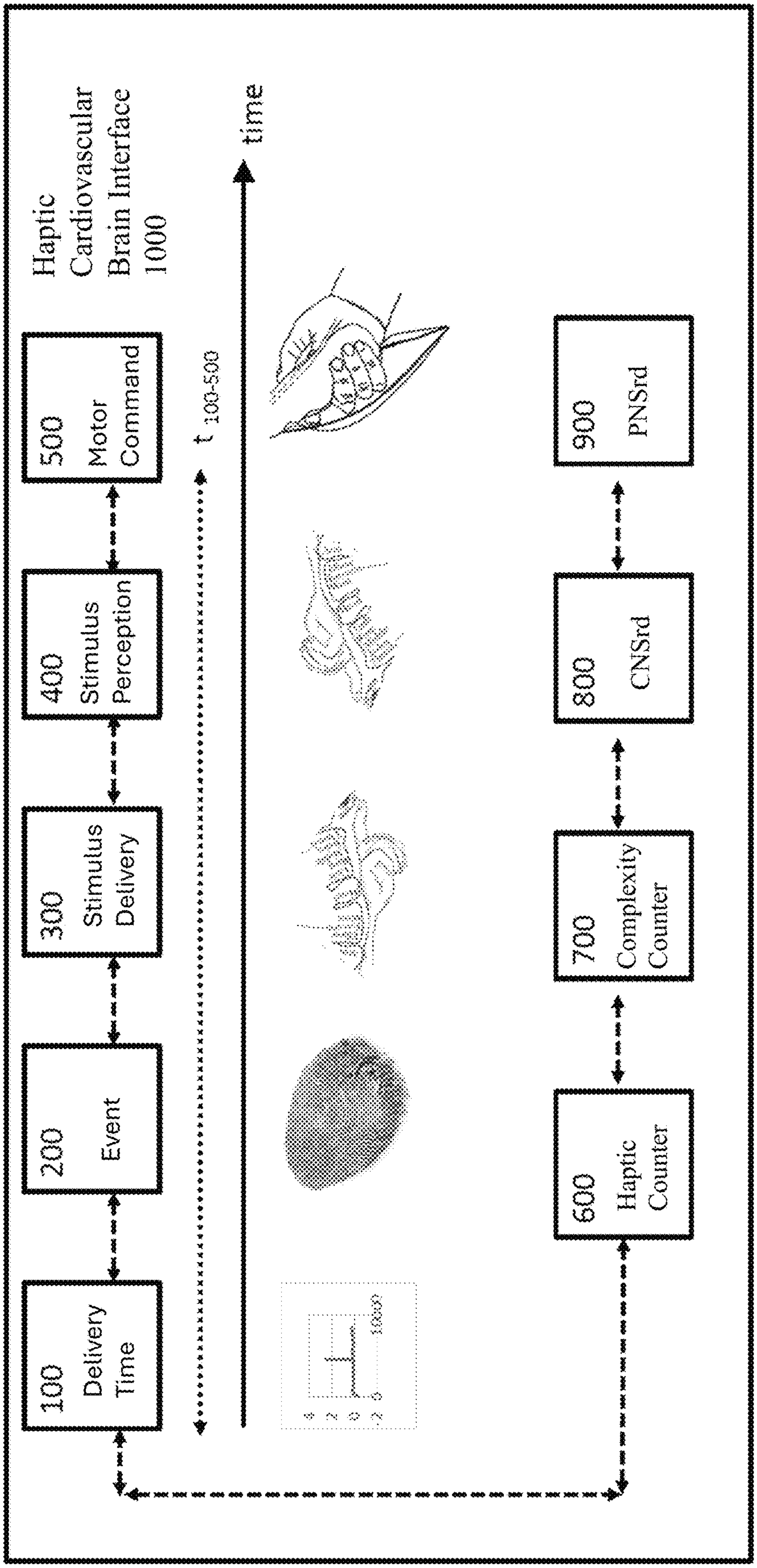
FIG. 30 shows a schematic representation of an embodiment of a haptic cardiovascular brain interface.

In one embodiment of the present disclosure, central and peripheral neurologic activity and motor responses are evaluated in many trained and untrained subjects as to determine pre-specified ranges for normal and abnormal delayed time frames between specific events. As depicted in FIG. 30, Haptic Cardiovascular Brain Interface 1000, note the time of delivery to a user of 100) biophysical/physiologic event (e.g., transeptal puncture), 200) delivery of a haptic stimulus (e.g., cutaneous, kinesthetic, proprioceptive, etc.), 300) sensory perception of the stimulus (by way of example using a surface EEG signal or other CNSrd), 400) central motor command to respond to the stimulus (by way of example using a surface EEG signal or other CNSrd), and 500) actual motor action (observed by a catheter directed intra-cardiac event; detected by a sensor on the user's body, instrument, integrated wearable haptic device, or catheter handle being controlled by a user, and/or an EMG signal or other PNSrd). The time for signal processing of the haptic system (e.g., 0.038 seconds) is a constant and not considered for the analysis of haptic motor reaction time. Determination of time between 100) and 500) $t_{100\text{-}500}$ is analyzed as the final denominator though specific interval time frames are assessed using a temporal counter as to determine more precisely when and at what point undesirable delays may be originating from.

In one embodiment, the PNrd not only receives afferent peripheral nerve signals but also delivers efferent electrical stimulation to motor assist interventionalists during procedures by delivering impulses to specific motor groups in an extremity, to control robotic arms/hands, or even mechanically constrain degrees of freedom of a surgical tool and limit an operator's ability to manipulate instrumentation.

Figure 32:
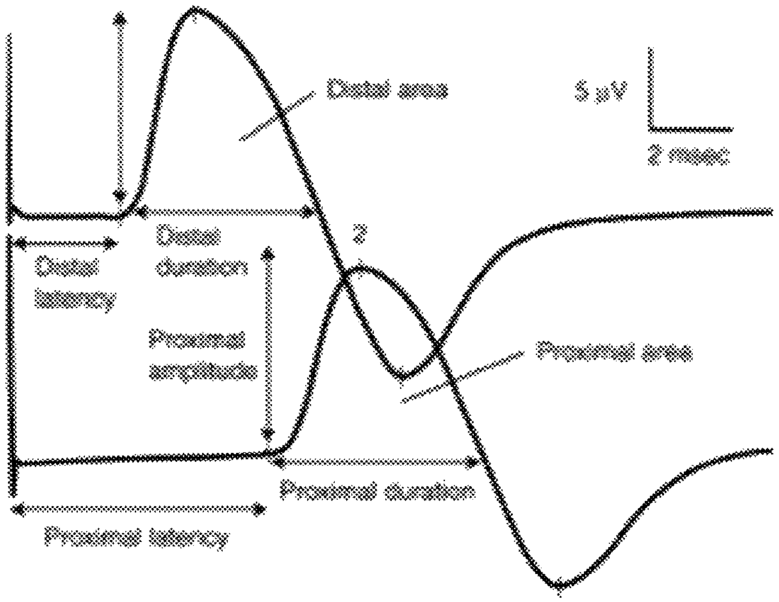
FIG. 32 show a set of graphical representations of time scale of central and peripheral neurologic and haptic motor response times and waveforms of amplitude, latency, duration of a given user's peripheral nerves.

By way of example, delays between 100) and 200) would indicate a system delay between time of sensed signal and delivery of haptic stimulus. This can be due to issues with signal processing, malfunction of the haptic actuator, or device connections (preferably Bluetooth/wireless). A delay between 200) and 300) would indicate that a given user may have a peripheral sensory deficit that could interfere with task completion/performance while delays between 400) and 500) are indicative of a peripheral motor deficit. Delays between 300) and 400) would be indicative of delays in cortical processing that could be improved with repeated training after identification of a lower level of competency in a given user or improvement in attention span (e.g., detected by CNSrd). Indeed, bench work has indicated that the first measurements of haptic motor reaction time in test subjects were longer than the last measurements. Detailed assessment of peripheral and central nervous system health can be determined with this system. By way of example as shown in FIG. 32 PNSrd can be used to evaluate the amplitude, latency, duration of a given user's peripheral nerves. This data can be analyzed by the system or Haptic Cardiovascular Brain Interface as to detect impaired motor skills and peripheral muscle fatigue. Likewise, CNSrd can identify the overall health of a given user based on analysis of the morphology and spatiotemporal aspects of measured central signals (e.g., EEG) and peripheral neurometrics providing a means for evaluating general neurologic well-being. From a procedural standpoint this is advantageous as some interventions can take several hours and more than one operator often works in unison as a team. Identifying when a user has a sensory, motor, or cognitive deficit (e.g., attention deficit due to saturation of attentional resources, fatigue, etc.) can prompt changes in operational procedures, such as having a different clinician to take over a procedure.

Figure 33:
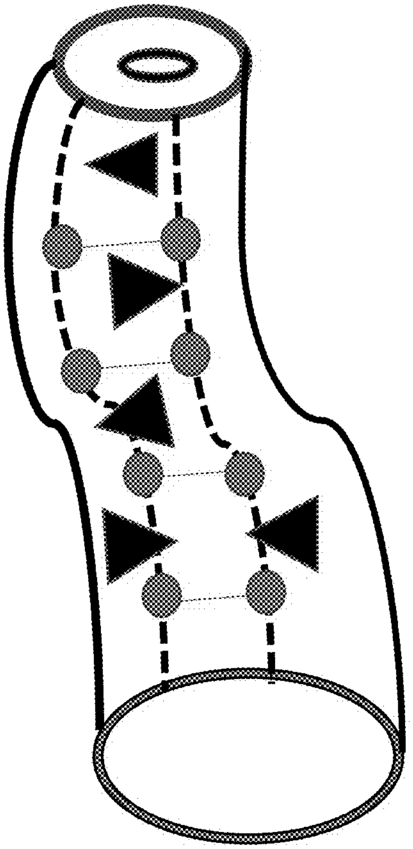
FIG. 33 show a schematic representation of an embodiment of a haptic sleeve system having peripheral electrodes for sensing neuromuscular action potentials embedded within the haptic sleeve.

In an embodiment of the present disclosure, the sensors for determining peripheral nerve recruitment and motor responses (PNSrd) are incorporated into the design of a wearable haptic device that interfaces with the CNSrd (even in a bidirectional fashion as to direct motor movement centrally rather than peripherally though this would require implanted brain electrodes in the motor cortex as of the time of this writing). As depicted in FIG. 33 triangular icons are representative of peripheral electrodes used to sense neuromuscular action potentials and the like as known by those experienced in the art and are embedded within the haptic sleeve or other haptic delivery system and interspersed between one or more haptic actuators. The location of the electrodes is distant enough from haptic actuators (e.g., 2-5 mm) and embedded as to enable adequate skin contact and not interfere with the functionality of haptic elements, conductors, and are shielded as necessary from ambient electromagnetic interference. The design and construct of the haptic enabled PNSrd is such that it can be either disposable, or reusable and sterilizable. In an embodiment, the PNSrd are situated to sense the most peripheral nerve innervation and more proximal locations that can extend up the arm using a sleeve design and be used to measure peripheral nerve (sensory and or motor) conduction times. The design illustrated is simplistic and in no means meant to limit the scope and spirit of the construct nor orientation/location/type of such sensors. Thus, the Haptic Cardiovascular Brain Interface provides integration of central nervous system and peripheral sensorimotor haptic monitoring with a wearable haptic interface that incorporates one or more PNSrd along one or more extremities and an EEG or other CNSrd that are all used for monitoring purposes.

Figure 34:
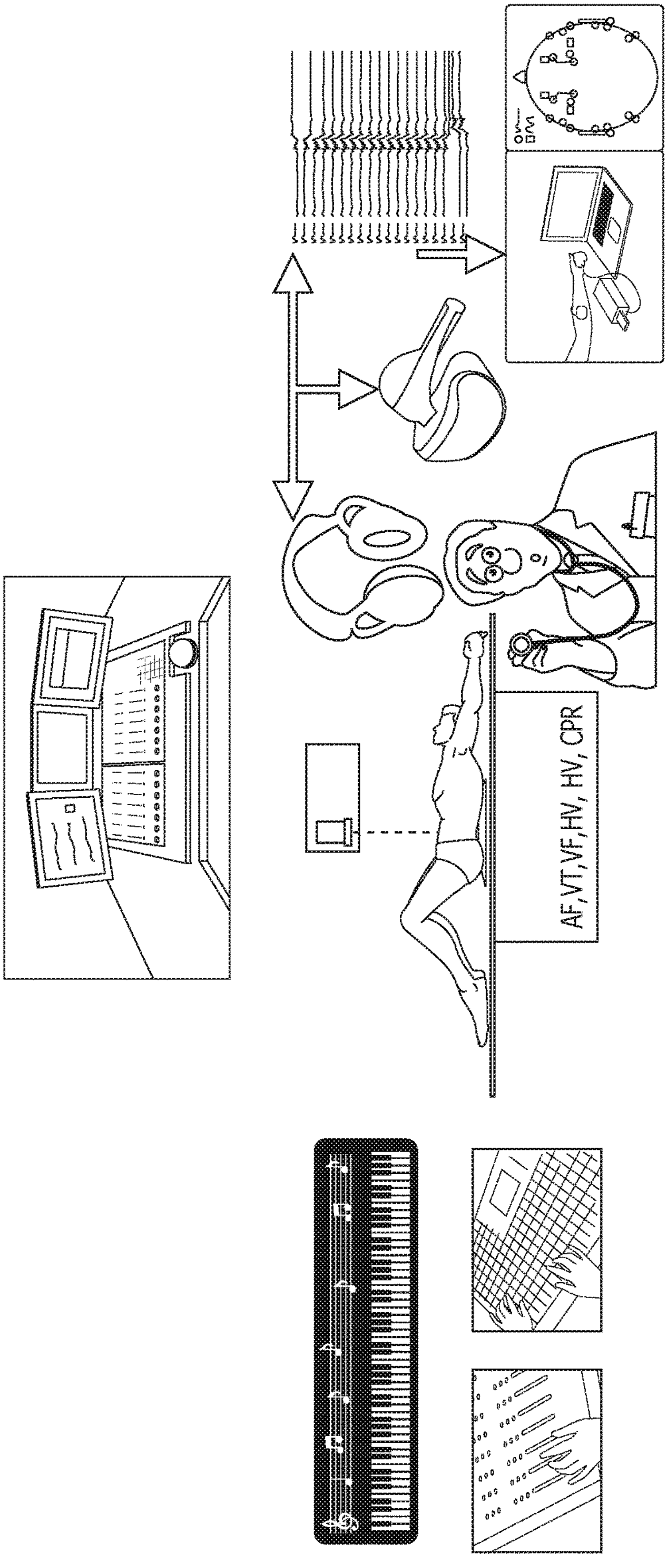
FIG. 34 show a schematic representation of an embodiment of an overall haptic brain interface system.

Interventional cardiovascular procedures including catheter ablation of arrhythmia and in particular atrial fibrillation ablation suffer from suboptimal success rates due to improper catheter manipulation (e.g., insufficient tissue contact) and result in excessive risk of complications when procedures are performed by less experienced operators. This limits the widespread utilization and precludes optimal health care cost savings from being realized. The Haptic Cardiovascular Brain Interface (1000) as shown in FIG. 34 serves to monitor and optimize the performance of interventional cardiologists and electrophysiologists by assessing user sensory and motor skills, levels of attention, cognition, and mental acuity and improves procedural technique and ergonomics. Because sense of touch is particularly advantageous in situations where visual channels are heavily loaded and notably absent during interventional cardiovascular procedures the current invention is geared to improve outcome and mitigate risk. Such optimization can be achieved by monitoring timing of biophysical, physiologic cardiovascular events and catheter based events relative to operator performance, and evaluate cases on a patient-by-patient basis as to alert clinicians to any performance impairments, device related concerns while accounting for procedural complexity. FIG. 34 depicts how Haptic Counter 600, complexity counter 700, non-procedural related sensors monitoring an operator's actions 700, CNSrd 800, PNSrd 900 function in toto as a Haptic Cardiovascular Brain Interface that monitors, teaches, and alerts interventionalists to suboptimal performance/conditions as to improve patient outcome, reduce need for additional procedures (whether therapeutic or to reduce adverse sequalae from complications), and ultimately to minimize health care costs.

In an embodiment, the Haptic Cardiovascular Brain Interface analyzes data from CNSrd and PNSrd and learns with AI/ML what recorded/monitored signals are associated with optimal procedural efficiency and outcome both in general and for specific actions. By way of example, 1000 will identify specific EEG signals/patterns associated with high level of attentiveness coupled by short latency haptic to motor reaction times detected by PNSrd with favorable procedural outcome. Through AI CNSrd can specifically detect CNS activity that can be implemented for robotic assisted procedures and shorten time between motor intention and motor output and improve the accuracy and dexterity of motor responses with robotic arms/instrumentation or motor assisted actions driven in part by an operator's hands and fingers that may be partly constrained by a prosthesis or imposed mechanical limitations on the ability of a user to manipulate inserted instrumentation (e.g., restricted range of motion). Ideally monitoring and connectivity for all the applications taught herein is wireless (e.g., Bluetooth).

Examples

The following examples are also intended as illustrative and in no manner limiting as to the scope and breadth of the foregoing description and the accompanying drawings to those of skill in the art.

I. a Haptic Feedback Computing System Comprising:

a. a cardiac device and one or more dissimilar sensors incorporated with the cardiac device, a plurality of dissimilar sensors configured to sense one or more input signals based on clinical characteristics of a patient, wherein the plurality of dissimilar sensors generate one or more output signals based on the sensed input signals;

b. a processor configured to receive and process the one or more output signals and performs haptic transduction based on the one or more output signals, wherein haptic transduction generates one or more haptic feedback signals associated with one or more neuroanatomical sites of an operator of the cardiac device having one or more haptic actuators configured to be activated for haptic feedback effect in response to the one or more haptic feedback signals;

c. a wearable haptic interface that fits along one or more anatomic sites of a user's extremity, extends from aspects of the fingers and hand to more proximal location about the arm, and is structured, programmed, and designed as to prevent slippage, user fatigue to repeated haptic sensations, limit exposure to body fluids, and is re-usable and/or disposable, providing the user with unencumbered and full dexterous control of the extremity, arm, hand, and digits with haptic effects generated by one or more haptic actuators positioned in varying geometric arrangements as to provide tactile and/or force feedback proportionate in amplitude to sensed signal amplitude by activating an increasing number of actuators and/or modifying the frequency response, quantitative, and qualitative haptic effect of one or more actuators; and d. an analytic system that evaluates temporal relationships between one or more clinician's central and peripheral nervous system's sensing and associated motor responses used to control, manipulate, position, or actuate an inserted or implanted cardiac device relative to measured biophysical and physiologic cardiovascular signals while performing diagnostic and therapeutic interventions on the heart and surrounding anatomic structures.

II. The haptic feedback computing system of example I, wherein The haptic feedback computing system is associated with a reciprocating wearable, wherein the reciprocating wearable configured to interact with the one or more neuroanatomical sites as to obtain measurements from and/or provide effects to the one or more neuroanatomical sties.

III. The haptic feedback computing system of example II, wherein the one or more neuroanatomical sites comprise one or more peripheral and central neuroanatomical sites; and a, wherein the reciprocating wearable includes at least one of kinesthetic, proprioceptive, temperature, tactile, and pressure receptors incorporated among the reciprocating wearable.

IV. The haptic feedback computing system of example II, wherein the reciprocating wearable includes one or more of a glove, a ring, a wristband, and a sleeve.

V. The haptic feedback computing system of example I, wherein the haptic feedback effect incorporates a polymeric material with a Young's elastic modulus approximating human connective tissue.

VI. The haptic feedback computing system of example I, wherein the processor is configured to analyze the one or more input signals and detect inaccurate signals prior to haptic transduction and/or the one or more haptic feedback signals being transmitted.

VII. The haptic feedback computing system of example 1 wherein the input signals based on the clinical characteristic of the patient comprise one or more of a static signal, a quasistatic signal, and a dynamic signal and the nature of the generated haptic signal is one or more of static, quasistatic, dynamic signal, wherein the nature of the sensed and generated signals may be the same or different.

VIII. The haptic feedback system computing system of example VII, wherein the input signals based on the clinical characteristic of the patient are sensed from one or more of tissue motion, blood flow, and tissue contact and include but are not limited to biophysical and physiologic signals arising from a catheter crossing biological tissue planes, transeptal puncture, epicardial puncture, intracardiac pressure, intra-aortic pressure, intra-pericardial pressure, intracardiac or intra-aortic blood flow, tissue motion, identifiers of tissue necrosis of myocardium exposed to radiofrequency ablation, thermal or cryoablation, electroporation from an internally located catheter or externally applied pulse field ablation system, catheter-tissue contact force, intra-cardiac and extra-cardiac electrical activity.

IX. The haptic feedback computing system of example VII, wherein the one or more static signals relate to a position, an orientation, a deformation of a bodily tissue, a temperature, a rendering of texture, or a biophysical signal of the patient.

X. The haptic feedback computing system of example VII, wherein the one or more quasistatic signals relate to one or more characteristic measurement(s) of the patient based on at least one of an impedance, a resistance, a capacitance, a voltage, reflected light, acoustic signal/ultrasound, or a current representative of a status of bodily tissue subjected to an external force and a degree of contact of one or more sensors sensing from within or exterior to the patient.

XI. The haptic feedback computing system of example I, wherein the input signals based on the clinical characteristic of the patient relate to one or more characteristic measurement(s) of the patient, including one or more characteristic measurement(s) based on a measurable index of tissue necrosis.

XII. The haptic feedback computing system of example I, wherein the cardiac device comprises one or more of a left atrial appendage occlusion device, a valvular repair/replacement hardware, a diagnostic cardiac system and a therapeutic cardiac system.

XIII. The haptic feedback computing system of example I, wherein the one or more input signals are selected from a set consisting of: anatomic signals, biophysical signals, or physiological signals.

XIV. The haptic feedback computing system of example I, wherein the one or more haptic actuators comprise at least one of a piezoelectric haptic unit selected from the set consisting of a deformable piezo actuator, a linear motor, a rotary motor, smart material(s), and a haptic speaker.

XV. The haptic feedback computing system of example I, wherein the haptic system is configured to store the one or more sensed input signals and the haptic feedback output to be used with respect to future haptic effect delivery.

XVI. The haptic feedback computing system of example I, wherein the one or more sensed input signals are sensed and stored in real time during use of the cardiac device.

XVII. The haptic feedback computing system of example I, wherein said system measures the temporal relationships between one or more of; time of a catheter crossing a biological tissue plane, sensor detection of intracardiac pressure, intra-aortic pressure, intra-pericardial pressure, intracardiac or intra-aortic blood flow, tissue motion, identifiers of tissue necrosis, time and degree of catheter-tissue contact, delivery of ablative energy to cardiac tissue, achievement of stable catheter-tissue contact force, modification in intra-cardiac or extra-cardiac electrical activity, changes in cardiac structure and function, intra-cardiac and extra-cardiac hemodynamics and blood flow patterns, insertion or implantation of therapeutic cardiac devices and any associated equipment used for said device insertion or implantation, or sensed signals dependent on and representative of the function or malfunction of inserted or implanted cardiac device.

XVIII. The haptic feedback computing system of example XVII wherein said temporal relationships analyzed relative to central and peripheral nervous system sensing are stored and evaluated as an assessment of a clinician's procedural and motor skills and the efficacy of different procedural techniques or procedural equipment.

XIX. The haptic feedback computing system of example XVII wherein said temporal relationships are analyzed relative to central and peripheral nervous system sensing are stored and evaluated as an assessment of functionality of a given haptic feedback system.

XX. The haptic feedback computing system of example XIX wherein said functionality of the haptic feedback system evaluates the robustness of signal sensing, signal processing, time delays related to one or more haptic actuators, connectivity of the haptic system.

XXI. A haptic feedback computing system that evaluates temporal relationships between one or more clinician's central and peripheral nervous system's sensing and associated motor responses relative to sensed/measured biophysical and physiologic cardiovascular signals while performing diagnostic and therapeutic interventions on the heart and surrounding anatomic structures and implements sensors for determining peripheral nerve recruitment and relevant motor responses.

XXII. The haptic feedback computing system of example XXI wherein peripheral nervous system sensing is accomplished by one or more non-invasive sensors incorporated into the design of a wearable haptic device that interfaces with a central nervous system recording device.

XXIII. The haptic feedback computing system of example XXI wherein said sensors are located on the skin of a user, associated medical instrument, integrated within a wearable haptic device, or part of a catheter, catheter handle, or robotic system, being controlled by the user to complete a diagnostic or therapeutic task on a patient's cardiovascular system.

XXIV. The haptic feedback computing system of example XXI wherein said sensing is accomplished by one or more of EEG, EMG, magnetoencephalography, quantum field analysis.

XXV. The haptic feedback computing system of example XXI wherein said analytic system is utilized as part of a brain computer interface.

XXVI. The haptic feedback computing system of example XXV, where analysis of said temporal relationships and central nervous system responses are analyzed as to identify when a given operator should have another team member take over due to detected sensory or motor impairment including an attention deficit due to saturation of attentional resources, fatigue, delays in haptic motor reaction time, delays in central nervous system processing, abnormalities in peripheral nerve health.

XXVII. The haptic feedback computing system of example XXV wherein artificial intelligence is used to identify recorded/monitored signals associated with optimal procedural efficiency and outcome both in general and for specific motor actions and educate operators as to improve their procedural technique.

XXVIII. The haptic feedback computing system of example XXV wherein connectivity is wireless.

XXIX. The haptic feedback computing system of example XXV wherein artificial intelligence is used to program the system to assist an operator's motor activity and control of procedural technique.

XXX. The haptic feedback computing system of example XXV wherein the peripheral nervous system recording device is therapeutic and not only receives afferent peripheral nerve signals for processing but also delivers efferent electrical stimulation to motor assist interventionalists during procedures by delivering impulses to specific motor groups in an extremity, control robotic arms/hands, or constrain degrees of freedom and limit an operator's ability to manipulate instrumentation in a deleterious fashion.

XXXI. The haptic feedback computing system of example XXV wherein haptic presentation is altered in real time by changing haptic signal features including but not limited to amplitude, frequency, quality, location of haptic feedback based on one or more of;

a. a default programming change that modifies the characteristics of haptic signal(s) based on duration of use as to prevent fatigue of attentional resources from repetitive afferent signals that lead to saturation receptors and uptake of neurotransmitters in the peripheral and/or central nervous systems
b. sensing algorithms in the haptic device that detect increases in an operator's haptic motor reaction time
c. an operator's personal preferences XXXII. The haptic feedback computing system of example XXV wherein said haptic response is generated by a. a haptic speaker or other haptic actuator wherein said haptic force effects of said speaker or actuator are generated at a programmed multiple of sensed signal proportionate to the cardiac cycle.
b. generated in locations as to optimize somatosensory recognition of biophysical and physiologic events.

XXXIII. The haptic feedback computing system of example XXV comprised of internally and/or externally deployed sensors including but not limited to accelerometers, piezosensors located in or on the haptic interface that sense timing of an operator's simple and complex handle/hand/finger motion and catheter manipulations relative to fiducial events (e.g., transeptal puncture, time between change in sensed signal representative of;

i. effective ablation, change in impedance, differential voltage, other sensing indicator of tissue necrosis, fluctuation in catheter: tissue contact force) and time of removal of applied ablation energy (e.g., delivery of PFA, cryo or thermal energy, radiofrequency energy) where said timing intervals are stored and available for review and comparison to previous haptic motor reaction times from the operator and other interventionalists.

XXXIV. The haptic feedback computing system of example XXV wherein further implementing a reciprocating haptic sensory glove/rings/wristband/sleeve/apparatus that incorporates a polymeric material blend capable of sensing an operator's actions and delivering haptic feedback where said polymeric blend is in part of whole composed of material with a Young's elastic modulus comparable to human skin, ligament, tendon, or connective tissue.

XXXV. A method for haptic feedback delivery comprising:

a. sensing, by a plurality of dissimilar sensors, one or more input signals based on clinical characteristics of a patient, wherein the plurality of dissimilar sensors are associated with a cardiac device utilized with the patient;
b. performing haptic transduction to generate one or more haptic feedback signals based on the one or more input signals;
c. transmitting the one or more haptic feedback signals to a reciprocating wearable;
d. designating one or more neuroanatomical sites on a user, incorporated with the reciprocating wearable, based on the one or more haptic feedback signals, wherein the one or more neuroanatomical sites of the reciprocating wearable include one or more haptic actuators;
e. activating the one or more haptic actuators, to deliver one or more haptic feedback effects to the user associated with the reciprocating wearable, based on the one or more haptic feedback signals;
f. where said haptic effect is generated by one or more haptic actuators positioned in varying geometric arrangements as to provide tactile and/or force feedback proportionate in amplitude to sensed signal amplitude by activating a increasing number of actuators and/or modifying the frequency response and qualitative haptic effect of one or more actuators.

XXXVI. The method for haptic feedback delivery of example XXXV, further comprising:

a. analyzing the sensed one or more input signals;
b. detecting inaccurate signals prior to haptic transduction and/or the one or more haptic feedback signals being transmitted; and
c. correcting the detected inaccurate signals.

XXXVII. The method for haptic feedback delivery of example XVII, further comprising:

a. storing the one or more sensed input signals and the haptic feedback output enabling future haptic effect delivery.

XXXVIII. The method for haptic feedback delivery of example XXXV, further comprising:

a. sensing and storing the one or more sensed input signals in real time during use of the cardiac device.

XXXIX. A haptic system that processes signals detected by contact and/or non-contact sensors as to provide an operator with holographic somatosensory tactile and force feedback information along an extremity or body part stimulating afferent neurologic impulses to various regions of brain creating a real time haptic representational map of the heart or haptic homunculus.

XL. The haptic system of example XXXVII wherein said regions of the brain include the parietal lobe in the cerebral cortex.

XLI. The haptic system of example XXXVII wherein said regions of the brain are contiguous and assigned to receive different haptic signals from different contiguous anatomic portions of a given extremity.

XLII. The haptic system of example XXXVII wherein said tactile and/or force feedback is presented in a holographic format preserving the depth, parallax and other properties of the actual tissue generating physiologic signals in real time.

XLIII. The haptic system of example XXXVII wherein specific haptic signals are delivered to portions of the user's body parts that have more numerous sensory innervation/connections (e.g., fingertips) and other haptic signals are delivered to anatomic sites with less complex/numerous sensory connections.

XLIV. The haptic system of example XLII wherein said signals of force and or tactile feedback stimulate varying sensory organs having one or more of tactile, kinesthetic, proprioceptive properties.

XLV. The haptic system of example XLIII wherein where said sensory organs include one or more of myelinated mechanoreceptive afferents, rapidly adapting type I (Meissner), rapidly adapting type 2 (Pacinian) receptors, slowly adapting type I (Merkel), slowly adapting type 2 (Ruffini), unmyelinated (e.g., C-tactile), sensory receptors in muscle, muscle spindles, Golgi tendon organs that are sensitive to velocity and stretch for communication of force information, and proprioceptive sensors found in joint spaces, differing sensory cutaneous branches of the median nerve that innervate the hand, wrist, arm, palmar digital cutaneous branches, palmar cutaneous branches that arise in the forearm and extend to the hand innervating lateral, and or medial aspects of the palm and digits.

XLVI. The haptic system of example XXXVII wherein the most distally stimulated body part exposed to force and or tactile signals is actuated using a concave shaped haptic speaker design that conforms to the user's stimulated body part.

XLVII. The haptic system of example XLV wherein where the amplitude of each haptic signal is proportionate to the sensed signal amplitude or at least a proportionality is maintained so that the baseline haptic signal (rather than the multiplicative interpolated signals) appropriately generates relative changes in sensed signal amplitude providing a haptic metric of physiologic information.

XLVIII. The haptic system of example XLVI wherein where the said sensed signal is one or more of heart rate, inotropic state of the heart, intracardiac electrogram amplitude, blood flow velocity, intracardiac pressure, tissue motion characteristics, catheter: tissue contact force or index of catheter tissue contact.

XLIX. The haptic system of example XLIII wherein said haptic signals are delivered based on the location of an inserted catheter's sensors and generates signals that are transduced in real time and delivered along the operator's extremity sequentially in a distal to proximal location based on time and location/space so that previously detected signals and/or more proximally detected signals are transduced in a haptic format more proximally along a finger, hand, wrist, arm or other body part as to provide temporal and spatial information (respectively) to the operator as the catheter is advanced into a more distal intracardiac location over time so that distinct locations of haptic actuation correlate to different peripheral anatomic locations, different time frames, and portrayed in distinct regions of the somatosensory cortex.

L. The haptic system of example XLVIII wherein said haptic signals provide a user with continuous position and time dependent haptic feedback that conveys quantitative information of intracardiac distances relative to the location of one or more aspects of an inserted catheter.

LI. The haptic system of example XLIX wherein said intracardiac distances are one or more of the distance between the interatrial septum and one or more pulmonary veins; the distance between the interatrial septum and left atrial appendage; the distance between a valve plane and other anatomic site; the distance between a catheter tip and any intracardiac or extracardiac anatomic structure.

LII. The haptic system of example L wherein said haptic signals consists of gentle contraction or actuation of segments of a wearable haptic finger or sleeve generated by stimulating piezoactuator filaments/yams at the location of conductive nodes, as that deformable piezoelectric yams focally contract about the operators finger, hand, wrist and the like at progressively more proximal locations, the distance of which is proportionate to the distance between the one or more of different anatomic locations, different segments of an inserted catheter, the relative distance between a given anatomic region and segment of an inserted catheter.

LIII. The haptic system of example LI wherein said gentle contraction or actuation is delivered by haptic transducers as to denote changes in distance over time between anatomic structures where said haptic signal is a previously stored surrogate identifier of a biophysical event acquired prior including but not limited to transeptal puncture and generated using either real-time haptic pulsations coincident with a 1:1 ratio or alternate ratio relative to the cardiac cycle.

LIV. The haptic system of example LI wherein said haptic signal is acquired from previously stored signals including but not limited to a stored loop of left atrial pressure acquired earlier during a procedure prior to the catheter being further advanced or manipulated within the heart or real time signal including but not limited to intracardiac electrogram, intracardiac pulse pressure, temporal denotation of a surface R wave or other index of cardiac systole.

LV. The haptic system of example LIII wherein said alternate ratio haptic effect is a higher frequency than 1:1 where the amplitude of the haptic effect relative to the sensed signal remains consistently proportionate and temporally related to the real time sensed signal in a 1:1 ratio coincident with the relevant sensed signal and gained according to sensed physiologic signal amplitude while the interpolated haptic signals remain fixed at a 1:1 ratio while the haptic effect signal has a lower amplitude as to prevent attenuation/habituation of tactile sensing and optimize operator haptic response times while preserving physiologically relevant temporal and amplitude information in a haptic format.

LVI. The haptic system of example LI wherein said location of a catheter's sensor relative to a given anatomic region is determined by one or more imaging modalities including but not limited to intracardiac echo, fluoroscopic data, electromagnetic, magnetic, impedance based navigational systems.

LVII. The haptic system of example LI wherein said sensed proximally located sensor's sensed physiologic/biophysical signal and generated haptic signal, respectively, is left atrial pressure which fades out in amplitude over time as a catheter approaches another more distal anatomic site and terminates the haptic signal once a specific tissue location is contacted or therapy is delivered and replaces it with a haptic signal based on acquisition of a distally located sensor's sensed physiologic/biophysical signal.

LVIII. The haptic system of example LVI wherein said delivered therapy includes one or more of application of ablation energy for treatment of atrial fibrillation, deployment of a left atrial appendage device to reduce stroke risk, implantation of an apparatus or repair of cardiac structure for treatment of valvular stenosis or regurgitation LIX. The haptic system of example LVII wherein where said proximally located sensed physiologic and generated haptic signals are complemented by more distally located sensed physiologic and generated haptic signals delivered by haptic actuators that are positioned in more proximal and distal locations of a given user's extremity, respectively.

LX. The haptic system of example LVIII wherein where said distal haptic signals are actuated at the distal most actuator and are acquired from an anatomic location including one or more of a pulmonary vein os, left atrial appendage, heart valve, intra- or extra-cardiac focus of arrhythmia.

LXI. The haptic system of example LVI wherein sensed proximally located sensed and palpable haptic signal fades out in amplitude over time and is no longer palpable once a catheter tip has reached its destination/most distally located anatomic site so the user can focus sensory attention on a different haptic signal palpable in a more distal anatomic location of a user's extremity once a specified tissue location is contacted or therapy is delivered.

LXII. The haptic system of example LX wherein said proximally located sensor senses blood flow velocity at a given valve plane or congenital anatomic anomaly and guides a user to manipulate a catheter across the valve plane or anomalous structure.

LXIII. The haptic system of example LXI wherein said sensor is one or more of an ultrasonic Doppler transducer, Doppler flowire, intracardiac or aortic pressure transducer, contact force sensor.

LXIV. The haptic system of example LXI wherein said valve plane is one or more of aortic, mitral, tricuspid, pulmonic valves, supravalvular or subvalvular stenosis.

LXV. The haptic system of example LXI wherein said congenital anomalous structure is one or more of atrial or ventricular septal defect, patent foramen *ovale*, patent ductus arteriosus, coarctation of the aorta.

LXVI. The haptic system of example LX wherein said therapy is induction of rapid ventricular pacing during deployment of a transfemoral aortic valve and sensed signal is one or more of an intracardiac electrogram, pulsed sequence from the pacing device, or surface ECG tracing during ventricular pacing.

LXVII. A haptic system capable of delivering to a user haptic signals that provide tactile and or force feedback in format of a haptic Doppler display with or without aliasing such that a user palpates a haptic signal that is proportionate in amplitude and/or frequency to anatomic distance or amplitude of blood flow velocity, and at pre-specified distances or at peak blood flow velocity, aliases and abruptly increases in haptic frequency and/or amplitude.

LXVIII. The haptic system of example LXVI wherein said haptic Doppler display denotes and haptically displays blood flow direction via the directional flow of haptic response along a user's extremity and/or a higher haptic frequency and/or amplitude when a sensor is moving towards a specific intracardiac sensor/location and lower haptic frequency and/or amplitude when moving away from a specific intracardiac sensor/location.

LXIX. The haptic system of example LXVI wherein said immersive augmented and virtual reality experience is implemented in the metaverse with a skeuomorphic design.

LXX. The haptic system of example LXVI wherein said anatomic distance is representative of intracardiac distance of an inserted catheter, guidewire, or other instrumentation relative the orifice of one or more cardiac valves, congenital heart defects, or pathologic vascular stenotic lesion.

LXXI. The haptic system of example LXIX wherein said haptic representation displays haptic effects that correspond to contiguous cardiovascular anatomic sites upon one or more of right hand, left hand, wrist, forearm, arm or other anatomic location and preserves the two- or three-dimensional anatomic locations and distances from sensed signals in real time.

LXXII. A haptic feedback computing system operatively coupled with a wearable haptic interface and a cardiac device comprised of one or more dissimilar sensors incorporated within or about the cardiac device configured to sense one or more input physiological signals based on clinical characteristics of a patient, wherein the dissimilar sensors generate one or more output signals based on the sensed input physiological signals;

a. configured to sense one or more salient events occurring during a cardiac procedure, wherein a plurality of dissimilar sensors generate one or more output signals based on sensed salient events dependent on the control, manipulation, and positioning of the cardiac device;

b, wherein salient events are determined by one or more of radiographic information, electroanatomic mapping data, navigational system data, acoustic/ultrasound data; data indicative of changes in catheter position, manipulation, orientation, actuation of an inserted catheter or instrument; data indicative of cardiac device insertion or implantation in a pre-specified location and the computing system generates output signals that are time stamped;

c. a processor configured to receive and process the one or more output signals and performs haptic transduction based on the one or more output signals, wherein haptic transduction generates one or more haptic feedback signals using a wearable haptic interface that fits along one or more anatomic sites of a user's extremity, extends from aspects of the fingers and hand to more proximal location about the arm, and is structured, programmed, and designed as to prevent slippage, user fatigue to repeated haptic sensations, and provide the operator with unencumbered and full dexterous control of the extremity, arm, hand, and digits needed to control, insert, or implant a cardiac device, cardiac instrument, or cardiac catheter.

LXXIII. The haptic system of example LXXI wherein said haptic representation displays haptic effects that correspond to contiguous cardiovascular anatomic sites upon one or more of right hand, left hand, wrist, forearm, arm or other anatomic location and preserves the two- or three-dimensional anatomic locations and distances from sensed signals in real time.

LXXIV. The haptic system of example LXXI wherein the sensor determination of time of occurrence of specific salient events is independent of the mechanism for controlling an inserted cardiac device or instrumentation and no changes in the design of said device or instrumentation are necessary.

LXXV. The haptic system of example LXXI wherein the sensor determination of time of occurrence of specific salient events is dependent of the mechanism for controlling an inserted cardiac device or instrumentation and changes in the design of said device or instrumentation are necessary.

LXXVI. The haptic system of example LXXI wherein the sensor determination of time of occurrence of specific physiological and salient events is determined by analysis of a composite of input and output signals generated by dissimilar sensors using artificial intelligence.

LXXVII. The haptic system of example LXXI wherein said time of occurrence of specific salient events and sensed physiological signals are stored and analyzed as to judge operator performance and train operators how to optimize procedural efficacy, safety, and success.

LXXVIII. The haptic system of example LXXI wherein said haptic feedback signals are generated by one or more haptic actuators positioned in varying geometric arrangements as to provide tactile and/or force feedback proportionate in amplitude to sensed signal amplitude by activating an increasing number of actuators and/or modifying the frequency response, quantitative, and qualitative haptic effect of one or more actuators.

LXXIX. The haptic system of example LXXI wherein determines the temporal relationships determined between one or more clinician's central and peripheral nervous system's sensing and associated motor responses used to control, manipulate, position, or actuate an inserted or implanted cardiac device relative to measured biophysical and physiologic cardiovascular signals while performing diagnostic and therapeutic interventions on the heart and surrounding anatomic structures.

LXXX. The haptic system of example LXXI wherein the said wearable device is configured to interact with the one or more neuroanatomical sites as to obtain measurements from and/or provide haptic effects to the one or more neuroanatomical sties inclusive of one or more of peripheral and central neuroanatomical sites; kinesthetic, proprioceptive, temperature, tactile, and pressure receptors.

LXXXI. The haptic system of example LXXI wherein the wearable device includes one or more of a distal most actuator opposed upon a fingertip, glove, ring, wristband, sleeve, polymeric material with a Young's elastic modulus approximating human connective tissue.

LXXXII. The haptic system of example LXXI wherein the processor is configured to analyze the one or more input signals and detect inaccurate signals prior to haptic transduction and/or the one or more haptic feedback signals being transmitted.

LXXXIII. The haptic system of example LXXI wherein the input signals based on the clinical characteristic of the patient comprise one or more of a static signal, quasistatic signal, and dynamic signal and the nature of the generated haptic signal is one or more of a static, quasistatic, dynamic signal, wherein the nature of the sensed and generated signals may be the same or different.

LXXXIV. The haptic system of example LXXI wherein the input signals are based on the clinical characteristic of the patient and are sensed from one or more of tissue motion, blood flow, and tissue contact and include but are not limited to biophysical and physiologic signals arising from a catheter crossing biological tissue planes, transeptal puncture, epicardial puncture, intracardiac pressure, intra-aortic pressure, intra-pericardial pressure, intracardiac or intra-aortic blood flow, tissue motion, identifiers of tissue necrosis of myocardium exposed to radiofrequency ablation, thermal or cryoablation energy, electroporation from an internally located catheter or externally applied pulse field ablation system, degree of catheter-tissue contact, catheter-tissue contact force, intra-cardiac and extra-cardiac electrical activity.

LXXXV. The haptic system of example LXXI wherein the one or more dissimilar sensors sense static signals related to a position, an orientation, a deformation of a bodily tissue or cardiac device, a temperature, a rendering of texture, or a biophysical signal of the patient.

LXXXVI. The haptic system of example LXXI wherein the one or more dissimilar sensors sense quasistatic signals related to one or more characteristic measurement(s) of the patient based including at least one of an impedance, resistance, capacitance, voltage, reflected light, acoustic/ultrasound, or a current representative of a status of bodily tissue subjected to an external force and a degree of contact of one or more sensors sensing from within or exterior to the patient.

LXXXVII. The haptic system of example LXXI wherein the one or more dissimilar sensors sense input signals based on the clinical characteristic of the patient relate to one or more characteristic measurement(s) of the patient, including one or more characteristic measurement(s) based on a measurable index of tissue necrosis; implantation of one or more of a left atrial appendage occlusion device, valvular repair/replacement hardware, a diagnostic cardiac system, and a therapeutic cardiac system.

LXXXVIII. The haptic system of example LXXI wherein said one or more haptic feedback signals is generated by at least one of a piezoelectric haptic unit, deformable piezoactuators, non-deformable piezoactuator, a linear motor, a rotary motor, a vibratory motor, smart material(s), and a haptic speaker.

LXXXIX. The haptic system of example LXXXVII wherein said haptic feedback signals are generated by one or more haptic actuators positioned in varying geometric arrangements as to provide tactile and/or force feedback proportionate in amplitude to sensed signal amplitude by activating an increasing number of actuators and/or modifying the frequency response and/or qualitative haptic effect of one or more actuators.

XC. The haptic system of example LXXI wherein said system measures the temporal relationships between one or more of; time of a catheter crossing a biological tissue plane, sensor detection of intracardiac pressure, intra-aortic pressure, intra-pericardial pressure, intracardiac or intra-aortic blood flow, tissue motion, identifiers of tissue necrosis, time and degree of catheter-tissue contact, delivery of ablative energy to cardiac tissue, achievement of stable catheter-tissue contact force, modification in intra-cardiac or extra-cardiac electrical activity, changes in cardiac structure and function, intra-cardiac and extra-cardiac hemodynamics and blood flow patterns, insertion or implantation of therapeutic cardiac devices and any associated equipment used for said device insertion or implantation, or sensed signals dependent on and representative of the function or malfunction of inserted or implanted cardiac device.

XCI. The haptic system of example LXXI wherein functions as a Haptic Cardiovascular Brain Interface that where said time stamp represents the temporal relationships between one or more clinician's central and peripheral nervous system's sensing and associated motor responses relative to sensed/measured biophysical and physiologic cardiovascular signals while performing diagnostic and therapeutic interventions on the heart and surrounding anatomic structures and implements sensors for determining peripheral nerve recruitment and relevant motor responses using one or more non-invasive sensors incorporated into the design of a wearable haptic device that interfaces with a central nervous system recording device, sensors located on the skin of a user, sensors associated with medical instrument, sensors integrated within a wearable haptic device, or part of a catheter, catheter handle, or robotic system being controlled by the user to complete a diagnostic or therapeutic task on a patient's cardiovascular system.

XCII. The haptic system of example XC wherein said sensing is accomplished by one or more of EEG, EMG, magnetoencephalography, quantum field analysis and is utilized as part of a brain computer interface.

XCIII. The haptic system of example XC further comprised of internally and/or externally deployed sensors including but not limited to accelerometers, piezosensors, gyroscopic sensors, located in or on the haptic interface that sense timing of an operator's simple and complex handle/hand/finger motion and catheter manipulations relative to fiducial events including but not limited to transeptal puncture, time intervals between varying sensed signals representative of one or more of:

i. effective ablation, change in impedance, differential voltage, other sensing indicator of tissue necrosis, fluctuation in catheter: tissue contact or contact force, time of removal of applied ablation energy; delivery of PFA, radiofrequency, cryo or thermal energy, where said timing intervals are stored and available for review and comparison to previous haptic motor reaction times from the operator and other interventionalists. XCIV. The haptic system of example XC wherein said sensed signals detected by contact and/or non-contact sensors are transduced to provide an operator with holographic somatosensory tactile and force feedback information along an extremity or body part stimulating afferent neurologic impulses to various regions of brain thereby creating a real time representational map of the heart, a haptic homunculus, in the parietal lobe of the cerebral cortex where contiguous regions of the brain receive different haptic signals from contiguous anatomic portions of a given extremity providing the user with haptic feedback in a holographic format that preserves the depth, parallax, and other properties of the actual cardiac device and cardiovascular tissue generating physiologic and salient signals in real time.

The examples and technologies taught herein are meant to be exemplary and by no means limit the scope and spirit of the invention nor limit the application to only cardiology interventions. Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations, and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112 (f) are not to be invoked unless the specific terms "means for" or "step for" are recited in a claim.

The invention claimed is:

1. A wearable haptic sensory feedback system for interventional cardiology procedures that is adapted to receive a first set of physiological signals representing a plurality of physiological parameters sensed by an interventional cardiology device and a second set of event signals representing at least one transduced procedural event associated with an interventional cardiology procedure performed by an operator, the system comprising:

at least two wearable surface elements, each wearable surface element configured to interface with a different region of an upper limb of the operator, wherein:

at least one of the wearable surface elements includes a first configuration of at least three haptic actuators configured to be positioned in a spaced apart relation to each other along a first section that corresponds to a linear portion of the upper limb of the operator having afferent nerves; and at least another of the wearable surface elements includes a second configuration of at least one haptic actuator configured to be positioned to correspond to a second section of the upper limb of the operator physically separated from first section;

a processor system operably coupled to the at least two wearable surface elements and to an electrical power source, the processor system adapted to receive the first set of physiological signals and the second set of event signals and configured to provide the operator with somatosensory tactile and force feedback along the first section as a set of real time spatial haptic sensations related to the first set of physiological signals and to provide the operator with somatosensory tactile and force feedback along the second section as a set of event haptic sensations related to the second set of event signals, and an operator sensor system configured to sense information related to peripheral nerve recruitment and motor responses of the operator during the interventional cardiology procedure, wherein the sense information from the operator sensor system is utilized by a processor system to evaluate attention and reaction of the operator during the procedure and to generate indications of changes in either attention or reaction of the operator during the interventional cardiology procedure.

2. The wearable haptic sensory feedback system of claim 1 wherein at least one wearable surface element is formed of a portion of a fabric sleeve with at least one haptic actuator having one or more haptic elements including at least one of piezo actuators, linear motors, rotary motors, smart materials, haptic speakers, piezo yarn, piezoelectric fibers, and flexible piezoelectric membranes.

3. The wearable haptic sensory feedback system of claim 1 wherein the interventional cardiology device is a catheter and the first set of physiological signals is generated in response to a set of sensors configured to detect physiological phenomena that vary as a distal portion of the catheter is inserted into a patient, and wherein the processor is configured to process and generate the set of real time spatial haptic sensations as a distal to proximal sequence of activations of the first configuration of at least three haptic actuators that the operator can correlate to different depths as the distal portion as the catheter is inserted into the patient.

4. The wearable haptic sensory feedback system of claim 1 wherein the processor system is configured to store the first set of physiological signals, the second set of event signals, the set of real time spatial haptic sensations related to the first set of physiological signals, and the set of event haptic sensations related to the second set of event signals for the interventional cardiology procedure for use in future training or assessment of the wearable haptic sensory feedback system or the operator.

5. The wearable haptic sensory feedback system of claim 4 wherein the processor system is configured to store a set of time stamps related to at least some of the first set of physiological signals and the second set of event signals for use in assessment of time periods between changes in physiological data of the first set of physiological signals or between events of the second set of event signals during the interventional cardiology procedure.

6. The wearable haptic sensory feedback system of claim 4 wherein the first set of physiological signals are representative of changes in distance over time between anatomic structures associated with the first set of physiological signals, and the set of real time spatial haptic sensations are generated using real-time haptic pulsations at a ratio relative to a sensed cardiac cycle of the patient during the interventional cardiology procedure.

7. A wearable haptic sensory feedback system for interventional cardiology procedures that is adapted to receive a first set of physiological signals representing a plurality of physiological parameters sensed by an interventional cardiology device and a second set of event signals representing at least one transduced procedural event associated with an interventional cardiology procedure performed by an operator, the system comprising:

at least two wearable surface elements, each wearable surface element configured to interface with a different region of an upper limb of the operator, wherein:

at least one of the surface elements includes a first configuration of at least three haptic actuators configured to be positioned in a spaced apart relation to each other along a first section that corresponds to a linear portion of the upper limb of the operator having afferent nerves; and at least another of the wearable surface elements includes a second configuration of at least one haptic actuator configured to be positioned to correspond to a second section of the upper limb of the operator physically separated from first section; and a processor system operably coupled to the at least two wearable surface elements and to an electrical power source, the processor system adapted to receive the first set of physiological signals and the second set of event signals and configured to provide the operator with somatosensory tactile and force feedback along the first section as a set of real time spatial haptic sensations related to the first set of physiological signals and to provide the operator with somatosensory tactile and force feedback along the second section as a set of event haptic sensations related to the second set of event signals, wherein the processor system is configured to provide the operator with somatosensory tactile and force feedback with the set of real time spatial haptic sensations related to the first set of physiological signals configured to stimulate afferent neurologic impulses to a first region of the brain of the operator, and the set of event haptic sensations related to the second set of event signals configured to stimulate afferent neurologic impulses to a different second region of the brain of the operator, whereby an increased ability of the operator to form a real time haptic representational map of a heart of the patient during the interventional cardiology procedure is increased.

* * * * *